US010604580B2

(12) United States Patent
Lokhorst et al.

(10) Patent No.: US 10,604,580 B2
(45) Date of Patent: Mar. 31, 2020

(54) COMBINATION THERAPIES WITH ANTI-CD38 ANTIBODIES

(71) Applicant: Janssen Biotech, Inc., Horsham, PA (US)

(72) Inventors: Henk M. Lokhorst, De Boelelaan (NL); Tuna Mutis, Zoeterwoude (NL); Inger S Nijhof, Utrecht (NL); Niels Van de Donk, Amsterdam (NL)

(73) Assignee: JANSSEN BIOTECH, INC., Horsham, PA (US)

( * ) Notice: Subject to any disclaimer, the term of this patent is extended or adjusted under 35 U.S.C. 154(b) by 0 days.

(21) Appl. No.: 15/386,391

(22) Filed: Dec. 21, 2016

(65) Prior Publication Data

US 2017/0107295 A1    Apr. 20, 2017

Related U.S. Application Data

(63) Continuation of application No. 14/847,428, filed on Sep. 8, 2015, now abandoned.

(60) Provisional application No. 62/087,287, filed on Dec. 4, 2014, provisional application No. 62/047,877, filed on Sep. 9, 2014.

(51) Int. Cl.
*A61K 39/395* (2006.01)
*C07K 16/28* (2006.01)
*A61K 31/203* (2006.01)
*A61P 35/00* (2006.01)
*A61K 39/00* (2006.01)

(52) U.S. Cl.
CPC ........ *C07K 16/2896* (2013.01); *A61K 31/203* (2013.01); *A61K 39/39558* (2013.01); *A61P 35/00* (2018.01); *A61K 2039/505* (2013.01); *C07K 2317/34* (2013.01); *C07K 2317/51* (2013.01); *C07K 2317/56* (2013.01); *C07K 2317/565* (2013.01); *C07K 2317/732* (2013.01); *C07K 2317/734* (2013.01); *C07K 2317/92* (2013.01)

(58) Field of Classification Search
CPC ................................... C07K 16/2896
See application file for complete search history.

(56) References Cited

U.S. PATENT DOCUMENTS

| | | | |
|---|---|---|---|
| 6,737,056 B1 | 5/2004 | Presta | |
| 7,183,387 B1 | 2/2007 | Presta | |
| 7,223,397 B1* | 5/2007 | Rosenblum | A61K 39/395 424/178.1 |
| 7,829,673 B2* | 11/2010 | De Weers | G01N 33/566 530/387.1 |
| 7,829,693 B2 | 11/2010 | Kreutzer et al. | |
| 8,088,896 B2 | 1/2012 | Tesar et al. | |
| 8,153,765 B2 | 4/2012 | Park et al. | |
| 9,040,050 B2 | 5/2015 | Van De Winkel | |
| 9,603,927 B2 | 3/2017 | Doshi | |
| 9,732,154 B2 | 8/2017 | Doshi | |
| 10,385,135 B2 | 8/2019 | Jansson et al. | |
| 2004/0141982 A1 | 7/2004 | Lust et al. | |
| 2004/0268425 A1 | 12/2004 | Bookbinder et al. | |
| 2006/0257397 A1 | 11/2006 | Throsby | |
| 2007/0148178 A1 | 6/2007 | Fyfe et al. | |
| 2008/0063642 A1 | 3/2008 | Adelman et al. | |
| 2008/0166344 A1 | 7/2008 | Nakahara et al. | |
| 2009/0076249 A1* | 3/2009 | De Weers | C07K 16/2896 530/387.3 |
| 2009/0148449 A1 | 6/2009 | De Weers | |
| 2009/0304687 A1 | 12/2009 | Drachman | |
| 2009/0304710 A1 | 12/2009 | Park et al. | |
| 2010/0068136 A1 | 3/2010 | Hansen | |
| 2010/0092489 A1 | 4/2010 | Van De Winkel et al. | |
| 2010/0285004 A1 | 11/2010 | Tesar et al. | |
| 2011/0044997 A1 | 2/2011 | Adler et al. | |
| 2011/0066111 A1 | 3/2011 | Teschner et al. | |
| 2011/0099647 A1 | 4/2011 | De Weers et al. | |
| 2011/0293606 A1 | 12/2011 | Lejeune | |
| 2011/0300157 A1 | 12/2011 | Devy et al. | |
| 2012/0201827 A1 | 8/2012 | Elias | |
| 2012/0219551 A1 | 8/2012 | Johnson et al. | |
| 2012/0231008 A1 | 9/2012 | Guo et al. | |
| 2012/0244110 A1 | 9/2012 | Chen et al. | |
| 2012/0258081 A1 | 10/2012 | Corringham et al. | |
| 2012/0259095 A1 | 10/2012 | Beliard et al. | |
| 2012/0295864 A1 | 11/2012 | Taube et al. | |
| 2013/0109593 A1 | 5/2013 | Hartmann et al. | |
| 2013/0137134 A1 | 5/2013 | Mordechai et al. | |
| 2013/0209355 A1* | 8/2013 | De Weers | C07K 16/2896 424/1.49 |
| 2013/0309250 A1 | 11/2013 | Cogswell et al. | |
| 2013/0323247 A1 | 12/2013 | Zugmaier et al. | |

(Continued)

FOREIGN PATENT DOCUMENTS

AU    2013203186 A1    5/2013
CL    2013001944 A1    9/2014

(Continued)

OTHER PUBLICATIONS

;Brown et al J. Immunol. May 1996; 156(9):3285-3291 (Year: 1996).*
Vajdos et al (J. Mol. Biol. Jul. 5, 2002;320(2); 415-428) (Year: 2002).*
George et al. (Circulation. 1998; 97: 900-906) (Year: 1998).*
Strome et al., The Oncologist, 2007; 12:1084-95 (Year: 2007).*
Brand et al., Anticancer Res. 2006; 26:463-70 (Year: 2006).*
"A Prospective Phase II of Daratumumab in Previously Treated Systemic Light Chain (AL) Amyloidosis", published online at (http://cms.cws.net/content/beta.myelomasociety.org/files/2017ash/Roussel,%20Murielle-ASH2017.pdf (2017).

(Continued)

*Primary Examiner* — Sheela J. Huff
(74) *Attorney, Agent, or Firm* — Hamilton, Brook, Smith & Reynolds, P.C.

(57) ABSTRACT

The present invention relates to combination therapies with anti-CD38 antibodies and all-trans retinoic acid.

18 Claims, 33 Drawing Sheets

Specification includes a Sequence Listing.

(56) References Cited

U.S. PATENT DOCUMENTS

| | | |
|---|---|---|
| 2014/0099254 A1 | 4/2014 | Chang et al. |
| 2014/0155584 A1 | 6/2014 | Elias et al. |
| 2014/0248238 A1 | 9/2014 | Wilson et al. |
| 2014/0271644 A1 | 9/2014 | Elias et al. |
| 2014/0356318 A1 | 12/2014 | Barken |
| 2015/0118251 A1 | 4/2015 | Deslandes |
| 2015/0125447 A1 | 5/2015 | Heider |
| 2015/0231235 A1 | 8/2015 | Van De Winkel |
| 2015/0246123 A1 | 9/2015 | Doshi |
| 2015/0246975 A1 | 9/2015 | Doshi |
| 2016/0009683 A1 | 1/2016 | Hansen et al. |
| 2016/0067205 A1 | 3/2016 | Lokhorst |
| 2016/0222106 A1 | 8/2016 | Doshi et al. |
| 2016/0367663 A1 | 12/2016 | Doshi et al. |
| 2016/0376373 A1 | 12/2016 | Ahmadi |
| 2017/0008966 A1 | 1/2017 | Chaulagain |
| 2017/0044265 A1 | 2/2017 | Ahmadi |
| 2017/0121414 A1 | 5/2017 | Jansson et al. |
| 2017/0121417 A1 | 5/2017 | Jansson et al. |
| 2017/0174780 A1 | 6/2017 | Doshi |
| 2017/0320961 A1 | 11/2017 | Doshi |
| 2018/0117150 A1 | 5/2018 | O'Dwyer |
| 2019/0127479 A1 | 5/2019 | Ahmadi et al. |
| 2019/0144557 A1 | 5/2019 | Ahmadi et al. |
| 2019/0233533 A1 | 8/2019 | Otten |

FOREIGN PATENT DOCUMENTS

| | | | | |
|---|---|---|---|---|
| CL | 2016002158 A1 | 7/2017 | | |
| EA | 009383 B1 | 12/2007 | | |
| EA | 015584 B1 | 10/2011 | | |
| EA | 201390993 A1 | 12/2013 | | |
| EP | 2561868 A1 | 2/2013 | | |
| EP | 2567976 A2 | 3/2013 | | |
| JP | 2002-534396 A | 10/2002 | | |
| JP | 2008-533977 A | 8/2008 | | |
| JP | 2009-511033 A | 3/2009 | | |
| JP | 2010-506582 A | 3/2010 | | |
| JP | 2014-509837 A | 4/2014 | | |
| NZ | 576122 | 9/2012 | | |
| WO | WO 89/08114 A1 | 9/1989 | | |
| WO | WO 92/01049 A2 | 1/1992 | | |
| WO | WO 94/17184 A1 | 8/1994 | | |
| WO | WO 96/16990 A1 | 6/1996 | | |
| WO | WO 98/16245 A1 | 4/1998 | | |
| WO | WO 98/16254 A1 | 4/1998 | | |
| WO | WO 98/50435 A1 | 11/1998 | | |
| WO | WO 99/62526 A2 | 12/1999 | | |
| WO | WO 00/06194 A2 | 2/2000 | | |
| WO | WO 00/40265 A1 | 7/2000 | | |
| WO | WO 01/97844 A1 | 12/2001 | | |
| WO | WO 02/06347 A1 | 1/2002 | | |
| WO | WO 02/32288 A2 | 4/2002 | | |
| WO | 2003/106498 A2 | 12/2003 | | |
| WO | WO 2004/058288 A1 | 7/2004 | | |
| WO | WO 2005/042019 A1 | 5/2005 | | |
| WO | WO 2005/044855 A2 | 5/2005 | | |
| WO | WO 2005/063819 A2 | 7/2005 | | |
| WO | WO 2005/103083 A2 | 11/2005 | | |
| WO | WO 2006/088951 A2 | 8/2006 | | |
| WO | WO 2006/099875 A1 | 9/2006 | | |
| WO | WO 2006/125640 A2 | 11/2006 | | |
| WO | WO 2007/042309 A2 | 4/2007 | | |
| WO | WO 2008/037257 A2 | 4/2008 | | |
| WO | WO 2008/047242 A2 | 4/2008 | | |
| WO | WO-2008037257 A2 * | 4/2008 | ....... | A61K 39/39558 |
| WO | WO 2008/073160 A2 | 6/2008 | | |
| WO | WO 2008/150530 A2 | 12/2008 | | |
| WO | WO 2009/062054 A1 | 5/2009 | | |
| WO | WO 2009/118142 A1 | 10/2009 | | |
| WO | WO 2009/128917 A2 | 10/2009 | | |
| WO | WO 2010/052014 A1 | 5/2010 | | |
| WO | 2010/061357 A1 | 6/2010 | | |
| WO | 2010/061358 A1 | 6/2010 | | |
| WO | 2010/061359 A1 | 6/2010 | | |
| WO | 2010-061360 A1 | 6/2010 | | |
| WO | WO 2011/154453 A1 | 12/2011 | | |
| WO | WO 2012/041800 A1 | 4/2012 | | |
| WO | WO-2012041800 A1 * | 4/2012 | ........... | A61K 31/454 |
| WO | WO 2012/076663 A1 | 6/2012 | | |
| WO | WO 2012/092612 A1 | 7/2012 | | |
| WO | WO 2013/059885 A2 | 5/2013 | | |
| WO | WO 2014/048921 A1 | 4/2014 | | |
| WO | WO 2014/068114 A1 | 5/2014 | | |
| WO | WO 2014/142220 A1 | 9/2014 | | |
| WO | WO 2014/178820 A1 | 11/2014 | | |
| WO | 2015/009726 A2 | 1/2015 | | |
| WO | WO 2015/066450 A1 | 5/2015 | | |
| WO | WO 2015/130728 A1 | 9/2015 | | |
| WO | WO 2015/130732 A2 | 9/2015 | | |
| WO | WO 2015/195555 A1 | 12/2015 | | |
| WO | WO 2015/195556 A1 | 12/2015 | | |
| WO | WO 2016/040294 A2 | 3/2016 | | |
| WO | WO 2016/089960 A1 | 6/2016 | | |
| WO | WO 2016/187546 A1 | 11/2016 | | |
| WO | WO 2016/209921 A1 | 12/2016 | | |
| WO | WO 2016/210223 A1 | 12/2016 | | |
| WO | WO 2017/079150 A1 | 5/2017 | | |
| WO | WO 2018/002181 A1 | 1/2018 | | |
| WO | WO 2019/089832 A1 | 5/2019 | | |

OTHER PUBLICATIONS

Aarhust, et al., "ADP-ribosyl Cyclase and CD38 Catalyze the Synthesis of a Calcium mobilizing Metabolite from NADP+," The Journal of Biological Chemistry, 270(51): 30327-30333 (1995).

Adriouch et al., "Extracellular NAD+: a danger signal hindering regulatory T cells," Microbes and Infection, 14:1284-1292 (2012).

Arican, et al., "Philadelphia chromosome (+) T-cell accute lymphoblastic leukaemia after renal transplantation," Nephrol Dial Transplant, vol. 14, No. 8, pp. 2054-2055, 1999.

Armitage et al., "Long-Term Remission Durability and Functional Status of Patients Treated for Diffuse Histiocytic Lymphoma with the CHOP Regimen," J. Clin. Oncol. 2:898-902, 1984.

Arthur, "Innovations in subcutaneous infusions," J. Infus. Nurs. 38(3); 179-87; Abstract. p. 180, col. 2., Jun. 2015.

Bachireddy, et al., "Haematological Malignancies: at the Forefront of Immunotherapeutic 1-23, 50-58, 65-68, 75-77 Innovation," Nature Reviews Cancer, vol. 15, pp. 201-215, Apr. 1, 2015 (Apr. 1, 2015).

Blankestijn, et al., "Could daratumumab be used to treat severe allergy?," Journal of Allergy and Clinical Immunology, Elsevier, Amsterdam, NL, vol. 139, No. 5, p. 1677, Jan. 19, 2017.

Brown, et al., "Tolerance of single, but not multiple, amino acid replacements in antibody VH CDR 2: a means of minimizing B cell wastage from somatic hypermutation?" The Journal of Immunology, 156: 3285-3291 (1996).

Carter et al., "Identification and validation of cell surface antigens for antibody targeting in oncology," Endocrine-Related Cancer, vol. 11, pp. 659-687, 2004.

Chari et al., "Subcutaneous Delivery of Daratumumab in Patients with Relapsed or Refractory Multiple Myeloma (RRMM): PAVO, an Open-label, Multicenter, Dose Escalation Phase 1b Study," American Society of Hematology, Clinical Trials.gov Identifier NCT02519452, Jun. 15, 2018.

Chari A. et al., "Subcutaneous delivery of daratumumab in patients (pts) with relapsed or refractory multiple myeloma (RRMM): PAVO, an openlabel, multicenter, dose escalation phase 1b study," 2017 ASH Annual Meeting *ANZMAP Multiple Myeloma Highlights, 2017.*

Chen, et al., "Selection and Analysis of an Optimized Anti-VEGF Antibody: Crystal Structure of an Affinity-matured Fab in Complex with Antigen," Journal of Molecular Biology, 293: 865-881 (1999).

Cheson et al., "Revised Response Criteria for Malignant Lymphoma," Journal of Clinical Oncology, vol. 25, No. 5, 579-586 (Feb. 10, 2007).

Chou, et al., "Drug Combination Studies and their Synergy Quantification Using the Chou-Talalay Method," Cancer Research, 70(2): 440-446 (2010).

(56) References Cited

OTHER PUBLICATIONS

Colman, "Effects of amino acid sequence changes on antibody-antigen interactions," A Structural View of Immune Recognition by Antibodies, Biomolecular Research Institute, Res Immunol., 145(1):33-6, Jan. 1994.

Cotner, et al., "Human T Cell Proteins Recognized by Rabbit Heteroantisera and Monoclonal Antibodies," International Journal of Immunopharmaceuticals, 3(3): 255-268 (1981).

Davies, et al., "Affinity improvement of single antibody VH domains: residues in all three hypervariable regions affect antigen binding," Immunotechnology, 2: 169-179 (1996).

Davis, et al., "Transgenic mice as a source of fully human antibodies for the treatment of cancer," Cancer and Metastasis Reviews, 18: 421-425 (1999).

Deckert, et al., "SAR650984, A Novel Humanized CD38-Targeting Antibody, Demonstrates Potent Antitumor Activity in Models of Multiple Myeloma and Other CD38β Hematologic Malignancies," Clinical Cancer Research. Sep. 1, 2014, vol. 20, No. 17, pp. 4574-4583.

Dennis, "Off by a Whisker," Nature, 442 (17): 749-741 (2006).

DePascalis, et al., "Grafting of 'Abbreviated' Complementarity-Determining Regions Containing Specificity-Determining Residues Essential for Ligand Contact to Engineer a Less Immunogenic Humanized Monoclonal Antibody," The Journal of Immunology, 169: 3076-3084 (2002).

De Weers, et al., "Daratumumab, a Novel Therapeutic Human CD38 Monoclonal Antibody, Induces Killing of Multiple Myeloma and Other Hematological Tumors," The Journal of Immunology, 186: 1840-1848 (2011).

De Weers et al., "Daratumumab, a Novel Therapeutic Human CD 38 Monoclonal Antibody, Induces Killing Multiple Myeloma and Other Hematological Tumors," The Journal of Immunology, 186: 1840-1848 (2010).

De Weers, M. et al., "Humax-CD38, a New Human CD38 Monoclonal Antibody, Effectively Mediates Killing of Multiple Myeloma and Plasma Cell Leukemia Cells," abstract, Submitted for the 16th European Congress of Immunology—ECI2006, Paris, France, Sep. 6-9, 2006.

De Weers et al., "HuMax-CD38, a new human CD38 monoclonal antibody, effectively mediates killing of multiple myeloma and plasma cell leukemia cells," The 23rd International Conference on Advances in the Application of Monoclonal Antibodies in Clinical Oncology, Jun. 26-28, 2006, Royal Myconian Resort & Thalasso Spa Center, Mykonos, Greece (Abstract).

Dos Santos, et al., Anti-Leukemic Activity of Daratumumba in Acute Myeloid Leukemia Cells and Patient-Derived Xenografts, Blood, vol. 124, Abstract 2312, 2014.

Doshi, et al., "Daratumumab Treatment in Combination with Chop or R-Chop Results in the Inhibition or Regression of Tumors in Preclinical Models of Non-Hodgkins Lymphoma," Haematologica, The Hematology Journal, 99(1): 138 (2014).

Ellis, et al., "Engineered Anti-CD38 Monoclonal Antibodies for Immunotherapy of Multiple Myeloma," The Journal of Immunology, 155: 925-937 (1995).

Engert, et al., "A Phase-I Study of an Anti-CD25 Ricin A-Chain Immunotoxin (RFT5-SMPT-dgA) in Patients with Refractory Hodgkin's Lymphoma," Blood, 99(2): 403-410 (1997).

Ferrero, et al., "Characterization and phylogenetic epitope mapping of CD38 ADPR cyclase in the cynomolgus macaque," BMC Immunology, 5(21): 1-13 (2004).

Field-Smith, "Bortezomid (Velcade™) in the treatment of multiple myeloma," Therapeutic and Clinical Risk Management, 2(3): 271-279 (2006).

Flavell, et al., "Therapy of human T-cell acute lymphoblastic leukaemia with a combination of anti-CD7 and anti-CD38-SAPORIN immunotoxins is significantly better than therapy with each individual immunotoxin," Br. J. Cancer, vol. 84, No. 4, pp. 571-578, 2001.

Franco, et al., "The transmembrane glycoprotein CD38 is a catalytically active transporter responsible for generation and influx of the second messenger cyclic ADP-ribose across membranes," FASEB Journal, 12: 1507-1520 (1998).

Fujimori, et al., "A Modeling Analysis of Monoclonal Antibody Percolation Though Tumors: A Binding-Site Barrier," Journal of Nucleic Medicine, 31: 119-1198 (1990).

Funaro et al., "CD38 Functions are Regulated Through an Internalization Step," Journal of Immunology, 160: 2238-2247 (1998).

Funaro, et al., "Human CD38: a versatile leukocyte molecule with emerging clinical prospectives," Fundamental and Clinical Immunology, 3(3): 101-113 (1995).

Funaro, et al., "Identification and characterization of an active soluble form of human CD38 in normal and pathological fluids," International Immunology, 8(11): 1643-1650 (1998).

Funaro, et al., "Involvement of the Multilineage CD38 Molecule in a Unique Pathway of Cell Activation and Proliferation," The Journal of Immunology, 145: 2390-2396 (1990).

Gallo, et al., "The human immunoglobulin loci introduced into mice: V(D) and J gene segment usage similar to that of adult humans," European Journal of Immunology, 30: 534-540 (2000).

Genmab "Humanx-CD38 Effective in Preclinical Studies," Genmab A/S, Stock Exchange Release 57/2005.

Genmab "Daratumumab Receives Breakthrough Therapy Designation from US Food and Drug Administration", Copenhagen, Denmark; May 1, 2013—Genmab A/S (OMX: GEN) disponible en: http://files.shareholder.com/downloads/AMDA-KPIBN/0x0x659093/64b187b8-830c-4252-acd6-8019b4199069/18%20Daratumumab%20breakthrough%20status_010513_uk.pdf, May 1, 2013.

George, et al., "Differential Effects of Anti-β2-Glycoprotein I Antibodies on Endothelial Cells and on the Manifestations of Experimental Antiphospholipid Syndrome," Circulation, 97: 900-906 (1998).

Goldmacher, et al., "Anti-CD38-Blocked Ricin: An immunotoxin for the Treatment of Multiple Myeloma," The American Society of Hematology, 84(9): 3017-3025 (1994).

Goodwin, "Subcutaneous Daratumumab Potential Game Changer for Multiple Myeloma," Oncology Times, 2017 American Society of Hematology Annual Meeting, p. 49, (2017).

Gopalakrishnan, et al. "Daratumumab improves the anti-myeloma effect of newly emerging multidrug therapies," Blood and Lymphatic Cancer: Targets and Therapy, 3: 19-24 (2013).

Graeff, et al., "Enzymatic Synthesis and Characterizations of Cyclic GDp-ribose," The Journal of Biological Chemistry, 269(48): 30260-30267 (1994).

Green, "Antibody engineering via genetic engineering of the mouse: XenoMouse strains are a vehicle for the facile generation of therapeutic human monoclonal antibodies," Journal of Immunological Methods, 231: 11-23 (1999).

Green, et al., "Antigen-specific human monoclonal antibodies from mice engineered with hyman Ig heavy and light chain YACs," Nature Genetics, 7: 13-21 (1994).

Guse et al., "Regulation of calcium signaling in T lymphocytes by the second messenger cyclic ADP-ribose," Nature 398:70-73, 1999.

Haart, et al., "Sepantronium bromide (YM155) improves daratumumab-mediated cellular lysis of multiple myeloma cells by abrogation of bone marrow stromal cell-induced resistance," Haematologica, Letters to the Editor, vol. 101, No. 8, pp. 339-342, 2016.

Hara-Yokoyama, "Alteration of enzymatic properties of cell-surface antigen CD38 by agonistic anti-CD38 antibodies that prolong B cell survival and induce activation," International Immunopharmacology, 8: 59-70 (2008).

Hartmann, Radioimmunotherapy of Nude Mice Bearing a Human Interleukin 2 Receptor α-expressing Lymphoma Utilizing the α-emitting Radionuclide-eonjugated Monoclonal Antibody 212Bi-anti-Tac, Cancer Research, 54: 4362-4370 (1994).

Henry, et al., "The use of basiliximab in solid organ transplantation," Expert Opinion Pharmacotherapy, 3(10: 1657-1663 (2002).

Holm, et al., "Functional mapping and single chain construction of the anti-cytokeratin 8 monoclonal antibody TS1," Molecular Immunology, 44: 1075-1084 (2002).

(56) References Cited

OTHER PUBLICATIONS

Hoshino, et al., "Mapping of the Catalylic and Epitopic Sites of Human CD38/NAD+ Glycohydrolase to a Functional Domain in the Carboxyl Terminus1," The Journal of Immunology, 158: 741-747 (1997).
Howard, et al., "Formation and Hydrolysis of Cyclic ADP-Ribose Catalyzed by lymphocyte Antigen CD38," Science, 262(5136): 1056-1059 (1993).
Ikehata, et al., "Autoantibodies against CD38 (ADP-ribosyl Cyclase/Cyclic ADP-ribose Hydrolase) that Impair Glucose-induced Insulin Secretion in Noninsulin-dependent Diabetes Patients," Journal of Clinical Investigations, 102(2): 395-401 (1998).
Jackisch, et al., "Subcutaneous versus intravenous formulation of trastuzumab for HER2-positive early breast cancer: updated results from the phase III HannaH study," Annals of Oncology, vol. 26, pp. 320-325, 2015.
Jackson, et al., "Isolation of a cDNA Encoding the Human CD38 (T10) molecule, A Cell Surface Glycoprotein With an Unusual Discontinuous Pattern of Expression During Lymphocyte Differentiation," The Journal of Immunology, 144(7): 2811-2815 (1990).
Jagannath, et al. "Treatment (tx) journeys in newly diagnosed multiple myeloma (NDMM) patients (pts): Results from the Connect MM Registry." Multiple Myeloma Update from the American Society of Clinical Oncology. (ASCO) 41st Annual meeting, Jun. 4, 2018.
Jakob, et al., "Stage-dependent Expression of CD7, CD45RO, CD45RA and CD25 on CD4-positive Peripheral Blood T-lymphocytes in Cutaneous T-cell Lymphoma," Acta Derm Venerology, 76: 34-36 (1996).
Jakobovits, "The long-awaited magic bullets: therapeutic human monoclonal antibodies from transgenic mice", Expert Opinion on Investigational Drugs, 7(4): 607-614 (1998).
Jang, et al., "The structural basis for DNA binding by an anti-DNA autoantibody," Molecular Immunology, 35: 1207-1217 (1998).
Johnson, et al., "Primary plasma cell leukemia: morphologic, immunophenotypic, and cytogenetic features of 4 cases treated with chemotherapy and stem cell transplantation," Annals of Diagnostic Pathology, 10: 263-268 (2006).
Jones, et al., "Depletion of CD25+ regulatory calls results in suppression of melanoma growth and induction of autoreactivity in mice," Cancer Immunity, 2: 1 (2002). Abstract.
Jones, et al., "Replacing the complementarity-determining regions in a human antibody with those from a mouse," Nature, 321: 522-525 (1986).
Kita et al., "Antitumor effects of YM155, a novel suppressant, against human aggressive non-Hodgkin Lymphoma," Leukemia Research, vol. 35, pp. 787-792, (2011).
Konopleva, et al., "Ligation of Cell Surface CD38 Protein with Agonistic Monoclonal Antibody Induced a Cell Growth Signal in Myeloid Leukemia Cells," The Journal of Immunology, 161: 4702-4708 (1998).
Konopleva, et al., "CD38 in Hematopoietic Malignancies," Chemical Immunol. Basel Karger, 75: 189-206 (2000).
Kreitman, et al., Phase I Trial of Recombinant Immunotoxin Anti-Tac (Fv)-PE38 (LMB-2) in Patients with Hematologic Malignancies, Journal of Clinical Oncology, 18: 1622-1636 (2000).
Kreuger, et al., "Successful in vivo blockade of CD25 (high-affinity interleukin 2 receptor) on T cells by administration of humanized anti-Tac antibody to patients with psoriasis," Journal of American Academy of Dermatology, 41(3): 448-458 (2000).
Kropff, et al., "Bortezomib in combination with dexamethoasone for relapsed multiple myeloma," Leukemia Research, 29: 587-590 (2005).
Kupiec-Weglinski, "CD25-Targeted Therapy Revisited," Transplantation, 69(3): 38-330 (2000).
Lande, et al., "CD38 ligation plays a direct role in the induction of IL-1β, I-6, and IL-10 secretion in resting human monocytes," Cellular Immunology, 220: 30-38 (2002).
Laurie, et al., "The role of CD4+CD25+ immunoregulatory T cells in the induction of autoimmune gastritis," Immunology and Cell Biology, 89: 567-573 (2002).
Lazar, et al., "Transforming Growth Factor α: Mutation of Aspartic Acid 47 and Leucine 48 Results in Different Biological Activities," Molecular and Cellular Biology, 8(3): 1247-1252 (1988).
Leonard, et al., "Molecular cloning and expression of cDNAs for the human interleukin-2 receptor," Nature 311(18): 626-631 (1984).
Leveque "Subcutaneous Administration of Anticancer Agents" Anticancer Research, Departments of Pharmacy, University Hospital, Strasbourg, France, vol. 34, pp. 1579-1586 (2014).
Lin, et al., "Structure-Function Relationships in Glucagon: Properties of Highly Purified Des-His1-, Monoiodi-, and [Des-Asn28, Thr29](homoserine lactone27)-glucagon," Biochemistry, 14(9): 1559-1563 (1975).
Lippincott-Schwartz, "Antibodies as cell Biological Tools," Current Protocols in Cell Biology, 16.0.1-16.0.2, (2002).
Liu et al., "Induction of Chemoresistance by All-Trans Retinoic Acid via a Noncanonical Signaling in Multiple Myeloma Cells," PLOS ONE, vol. 9, No. 1, p. Article No. e85571, Jan. 2014.
Lonberg, et al., "Antigen-specific human antibodies from mice comprising four distinct genetic modifications," Nature: 308: 856-859 (1994).
Lu et al., "Issues Related to Targeted Delivery of Proteins & Peptides," The AAPS Journal, vol. 8, No. 3, Article 55, pp. E466-E478, Jul. 21, 2006.
MacCallum, et al., "Antibody-antigen Interactions: Contact Analysis and Binding Site Topography," Journal of Molecular Biology, 262, 732-745 (1998).
Malavasi, et al., "Human CD38: a glycoprotein in search of a function," Immunology Today, 15(3): 95-97 (1994).
Maloney, et al., "Antibody Therapy for Treatment of Multiple Myeloma," Semin Hematol. 36 (Suppl. 3): 30-33 (1999).
Matas-Cespedes et al., "Daratumumab, a Novel Human Anti-CD38 Monoclonal Antibody for the Treatment of Chronic Lymphocytic Leukemia and B-Cell Non-Hodgkin Lymphoma," Blood, vol. 120, Abstract 3935, 2012 (Abstract Only).
McCarthy, P.L., "Strategies for induction, autologous hematopoietic stem cell transplantation, consolidation, and maintenance for transplantation-eligible multiple myeloma patients", Hematology, vol. 2013, NI. 1, Dec. 1, 2013, pp. 496-503, XP55500358.
McKelvey, et al., "Hydroxyldaunomycian (Adriamycin) Combination Chemotherapy in Malignant Lymphoma," Cancer, vol. 38, No. 4, pp. 1485-1493 (Oct. 1976).
Mills, et al., "Characterization of Monoclonal Antibodies that Inhibit CD38 ADp-ribosyl Cyclase Activity," LSSURP HLB Program, Department of Pharmacology, University of Minnesota, 2007.
Mikhael et al., Blood 119:4391-94 (Year: 2012).
Mohammad et al., "The Addition of Bryostatin 1 to Cyclophosphamide, Doxorubicin, Vincristine, and Prednisone (CHOP) Chemotherapy Improves Response in a CHOP-resistant Human Diffuse Large Cell Lymphoma Xenograft Model," Clinical Cancer Research, vol. 6, 4950-4956 (Dec. 2000).
Morrison, et al., "Chimeric human antibody molecules: Mouse antigen-binding domains with human constant region domains," Proceedings of the National Academy of Science USA, 8 6851-6855 (1984).
Mrowietz, "Treatment of Severe Psoriasis with Anti-CD25 Monoclonal Antibodies," Arch. Dermatology, 136: 675-676 (2000).
Mukherjee, et al., "Production and Characterization of Protective Human Antibodies against Shiga Toxin 1," Infection and Immunity, 70(10): 5896-5899 (2012).
Muyldermans, "Single domain camel antibodies: current status," Reviews in molecular Biotechnology, 74: 277-302 (2001).
Muyldermans, et al., "Recognition of antigens by single-domain antibody fragments: the superfluous luxury of paired domains," Trends in Biochemical Sciences, 26(4): 230-235 (2001).
Najjar et al., "Abstract P227: Accumulation of MDSC Subsets in Renal Cell Carcinoma 14-17, 54 Correlates with Grade and Progression Free Survival, and is Associated with Intratumoral Expression of IL-1β, IL-8 and CXCL5," Journal for Immunotherapy of Cancer, vol. 2, p. 110-112, Nov. 6, 2014 (Nov. 6, 2014).

(56) References Cited

OTHER PUBLICATIONS

Nijhof, et al., "Modulation of CD 38 Expression Levels on Multiple Myeloma Tumor Cells by All-Trans Retinoic Acid Improves the Efficacy of the Anti-CD 38 Monoclonal Antibody Daratumumab," Blood, American Society of Hematology, US, vol. 124, No. 21, p. 2096, Dec. 6, 2014. (Abstract Only).
Nikaido, et al., "Molecular cloning of cDNA encoding human interleukin-2 receptor," Nature, 311: 631-635 (1984).
Offidani et al., "An evidence-based review of ixazomib citrate and its potential in the treatment of newly diagnosed multiple myeloma," OncoTargets and Therapy, vol. 7, pp. 1793-1800, (2014).
Onizuka, et al., "Tumor Rejection by in Vivo Administration of Anti-CD25 (Interleukin-2 Receptor α Monoclonal Antibody," Cancer Research, 59: 328-3133 (1999).
Orlowski, "The Ubiquitin Proteasome pathway from Bench to Bedside," American Society of Hematology, 220-225 (2005).
Ostberg, et al., "Human and humanized monoclonal antibodies: preclinical studies and clinical experience," Biochemical Society Transactions, 23: 1-6 (1995).
Padlan, et al., "Identification of specificity-determining resides in antibodies," FASEB Journal, 9: 135-139 (1995).
Parren, et al., "HuMax-CD38, a new human CD38 monoclonal antibody, effectively mediates killing of multiple myeloma and plasma cell leukemia cells," American Society of Hematology 47th annual meeting, Atlanta, Georgia, USA, Dec. 10-13, 2005 (Abstract).
Parren, et al., HuMax-CD38, Myconos, (Jun. 26, 2006).
Parren, et al., HuMax-CD38, Torino, (Jun. 8-10, 2006).
Pascual, et al., "Anti-interleukin-2 receptor antibodies: basiliximab and daclizumab," Nephrology Dial. Transplant, 16: 1756-1760 (2001).
Paul, M.D., "Fundamental Immunology," Chapter 9, Raven Press, New York, 3rd ed., 29-295 (1993).
Peipp, et al., Fully Human CD38 Antibodies Efficiently Trigger ADCC and CDC of Multiple Myeloma Cell Lines and Primary Tumor Cells (Poster), Blood, vol. 106(11):944A, 47th Annual Meeting of the American Society of Hematology, 2005; published Nov. 16, 2005.
Peipp, et al., Fully Human CD38 Antibodies Efficiently Trigger ADCC and CDC of Multiple Myeloma and Plasma Cell Leukemia Cells (Poster 2) Conference proceedings, poster presentation at the 2005 Annual Meeting of the American Society of Hematology, Dec. 12, 2005.
Peipp, et al., 47th Annual Meeting of the American Society of Hematology, Atlanta, GA, Dec. 10-13 (2005). (Meeting Abstract).
Peng, et al., "Oncolytic measles viruses displaying a single-chain antibody against CD38, a myeloma cell marker," Blood, 101, 2557-2562 (2003).
Richardson, et al., "Daratumumab," Drugs of the Future, 38(8): 545-554 (2013).
Rituxan Hycela Label, "Highlights of prescribing information. Rituxan Hycela™ (rituximab and hyaluronidase human) injection, for subcutaneous use," 32 pages (Jun. 2017).
Salar et al., "Comparison of Subcutaneous Versus Intravenous Administration of Rituximab as Maintenance Treatment for Follicular Lymphoma: Results From a Two-Stage, Phase IB Study," Journal of Clinical Oncology, vol. 32, No. 17, pp. 1782-1791, (Jul. 10, 2014).
Sanchez-Gonzalez et al., "Rituximab subcutaneous in B-Cell non-Hodgkin lymphoma: clinical experience in a single center," Leukemia & Lymphoma, vol. 59, No. 4, pp. 1019-1021 (2018).
Shields, et al., "High Resolution mapping of the binding site on human IgG1 for FcγRi, FcγRII, FcγRIII, and FcRn and design of IgG1 variants with improved binding to the FcγR," J. Biol. Chem., vol. 276, No. 9, pp. 6591-6604, 2001.
Shpilberg, et al., "Subcutaneous administration of rituximab (MabThera) and trastuzumab (Herceptin) using hyaluronidase," British Journal of Cancer, vol. 109, pp. 1556-1561, 2013.
Shubinsky, et al., "The CD38 Lymphocyte Differentiation Marker: New Insight into Its Ectoenzymatic Activity and Its Role as a Signal Transducer," Immunity, 7: 315-324 (1997).
Skeel, Handbook of Cancer Gliemotherapy, 3rd edition, Little, Brown & Co., pp. 343 (1991).
Sonneveld, P. and Annemiek Broijl, "Treatment of Relapsed and Refractory Multiple Myeloma," Review Article, Leaders in Hematology, review series, Haematologica, 101(4):396-406 (2016). Exhibit A.
Tabernero, et al., "Adult precursor B-ALL with BCR/ABL gene rearrangements displays a unique immunophenotype based on the pattern of CD10, CD34, CD13, and CD38 expression," Leukemia, vol. 15, No. 3, pp. 406-414, 2001.
Terhorst, et al., "Biochemical Studies of the Human Thymocyte Cell-Surface Antigens T6, T9 and T10," Cell, 23: 771-780 (1981).
Usmani, et al., "Clinical efficacy of daratumumab monotherapy in patients with heavily pretreated relapsed or refractory multiple myeloma," Blood, vol. 128, No. 1, pp. 37-44, (May 23, 2016).
Vadjos, et al., "Comprehensive Functional Maps of the Antigen-binding Site of an Anti-ErbB2 Antibody Obtained with Shotgun Scanning Mutagenesis," Journal of Molecular Biology, 320: 415-428 (2002).
Van Bueren, et al., "Direct In Vitro Comparison of Daratumumab With Surrogate Analogs of Anti-CD38 Antibodies," New Evidence Apr. 2015 [retrieved on Feb. 3, 2016] Retrieved from the Internet: URL: Http:///www.newevidence.com/oncology/direct-in-vitro-comparison-of-daratumumab-with-surrogate-analogs-of-anti-cd38-antibodies>.
Van de Donk et al., "Monoclonal antibodies targeting CD38 in hematological malignancies and beyond authors' addresses," Immunological Reviews, vol. 270, pp. 95-112, Feb. 10, 2016.
Venner et al., "Cyclophosphamide, bortezomib, and dexamethasone therapy in AL amyloidosis is associated with high clonal response rates and prolonged progression-free survival," Blood, vol. 119, No. 9, pp. 4387-4390, (2012).
Vorre, et al., "Multiple Daratumumab Abstracts to be Presented at EHA," ArrayDiagnostica, Abstract Only (2014).
Wagner, V., et al., "Preclinical Efficacy of Sepantronium Bromide (YM155) in multiple myeloma is conferred by down regulation of Mcl-1," Oncotarget, 5(21): 10237-10250 (2014).
Wagner et al., "Survivin in Multiple Myeloma: Prognostic and Therapeutic Implications," vol. 118, Article 137, 2011 (Abstract Only).
Ye et al, "Abstract P240: Treg Increases HepG2 Cell Growth by RANK-RANKL pathway." 1-23, 50-58, 65-68, 75-77, Journal for Immunotherapy of Cancer, Nov. 6, 2014 (Nov. 6, 2014), vol. 2, pp. 115-117.
WCJ van de Donk, "A Phase 1 and Phase 2 Study of Daratumumab in Combination With All-Trans Retinoic Acid in Relapsed/Refractory Multiple Myeloma," Clinical Trials.gov Identification No. NCT02751255; (Apr. 26, 2016).
Genmab Announces Daratumumab and Ofatumumab Data to Be Presented at American Society of Hematology Annual Meeting (ASH), American Society of Hematology Annual Meeting and Exposition, San Francisco, California, Media Release 06; pp. 1-3 (Dec. 2014).
Johnson & Johnson, Janssen to Demonstrate Breadth of Oncology Portfolio with 42 Clinical Data Presentation at the 2014 American Society of Hematology (ASH) Annual Meeting, San Francisco, California (Dec. 2014).
Daratumumab in Subjects with Relapsed/Refractory Acute Myelogenous Leukemia or High-Risk Myelodysplastic Syndrome, retrieved from the Internet URL: https://clinicaltrials.gov/ct2/show/NCT02751255 (2018).
International Preliminary Report on Patentability dated May 5, 2018 for International Application No. PCT/US2016/59893, entitled "Subcutaneous Formulations of Anti-CD38 Antibodies and Their Uses".
International Search Report and Written Opinion dated Jan. 24, 2017 for International Application No. PCT/US2016/59893, entitled "Subcutaneous Formulations of Anti-CD38 Antibodies and Their Uses".
International Preliminary Report on Patentability dated Dec. 26, 2017 for International Application No. PCT/US2016/038702, entitled "Combination Therapies for Heme Malignancies With Anti-CD38 Antibodies and Survivin Inhibitors".

(56) References Cited

OTHER PUBLICATIONS

International Search Report and Written Opinion dated Nov. 29, 2016 for International Application No. PCT/US2016/038702, entitled "Combination Therapies for Heme Malignancies With Anti-CD38 Antibodies and Survivin Inhibitors".
International Search Report on Patentability dated Mar. 14, 2017 for International Application No. PCT/US2015/048899, entitled "Combination Therapies With Anti-CD38 Antibodies".
International Search Report and Written Opinion dated Apr. 8, 2016 for International Application No. PCT/US2015/048899, entitled "Combination Therapies With Anti-CD38 Antibodies".
International Preliminary Report on Patentability dated Nov. 21, 2017 for International Application No. PCT/US2016/033544, entitled "Anti-CD3 8 Antibodies for Treatment of Light Chain Amyloidosis and Other CD38-Positive Hematological Malignancies".
International Search Report and Written Opinion dated Oct. 24, 2016 for International Application No. PCT/US2016/033544, entitled "Anti-CD38 Antibodies for Treatment of Light Chain Amyloidosis and Other CD38-Positive Hematological Malignancies".
International Preliminary Report on Patentability dated Jun. 6, 2016 for International Application No. PCT/US2015/063371, entitled "Anti-CD38 Antibodies for Treatment of Acute Myeloid Leukemia".
International Search Report and Written Opinion dated Feb. 19, 2016 for International Application No. PCT/US2015/063371, entitled "Anti-CD38 Antibodies for Treatment of Acute Myeloid Leukemia".
International Preliminary Report on Patentability dated Dec. 26, 2017 for International Application No. PCT/US2016/039165, entitled "Immune Modulation and Treatment of Solid Tumors With Antibodies That Specifically Bind CD38".
International Search Report and Written Opinion dated Oct. 14, 2016 for International Application No. PCT/US2016/039165, entitled "Immune Modulation and Treatment of Solid Tumors With Antibodies That Specifically Bind CD38".
International Preliminary Report on Patentability dated Sep. 6, 2016 for International Application No. PCT/US2015/017425, entitled "Anti-CD38 Antibodies for Treatment of Acute Lymphoblastic Leukemia".
International Search Report and Written Opinion dated Sep. 21, 2015 for International Application No. PCT/US2015/017425, entitled "Anti-CD38 Antibodies for Treatment of Acute Lymphoblastic Leukemia".
International Search Report and Written Opinion dated Sep. 25, 2017 for International Application No. PCT/EP2017/066063, entitled "Treatment of IgE-Mediated Diseases With Antibodies That Specifically Bind CD38".
International Preliminary Report on Patentability dated Sep. 6, 2016 for International Application No. PCT/US2015/017420, entitled "Combination Therapies With Anti-CD38 Antibodies".
International Search Report and Written Opinion dated Jul. 8, 2015 for International Application No. PCT/US2015/017420, entitled "Combination Therapies With Anti-CD38 Antibodies".
Intellectual Property Office of Singapore Written Opinion dated Apr. 17, 2018 for Application No. 11201701867S, entitled "Combination Therapies with Anti-CD38 Antibodies".
Supplementary European Search Report dated Feb. 21, 2018 for European Application No. EP 15839752, entitled "Combination Therapies with Anti-CD38 Antibodies".
ClinicalTrials.gov "Study of YM155 in Refractory Diffuse Large B-cell Lymphoma (DLBCL Subjects)," Interventional Studies, U.S. National Library of Medicine, https://clinicaltrials.gov/ct2/show/record/NCT00498914, retrieved on Sep. 10, 2018.
Non Final Office Action for U.S. Appl. No. 15/340,290 dated Nov. 20, 2017.
Final Office Action for U.S. Appl. No. 15/340,290 dated May 16, 2018.
Non Final Office Action for U.S. Appl. No. 15/340,290 dated Oct. 10, 2018.
Non Final Office Action for U.S. Appl. No. 15/366,474 dated Nov. 20, 2017.
Final Office Action for U.S. Appl. No. 15/366,474 dated May 16, 2018.
Applicant Initiated Interview for U.S. Appl. No. 15/366,474 dated Sep. 17, 2018.
Non Final Office Action for U.S. Appl. No. 15/366,474 dated Oct. 11, 2018.
Non Final Office Action for U.S. Appl. No. 15/189,577 dated Oct. 31, 2017.
Final Office Action for U.S. Appl. No. 15/189,577 dated Apr. 13, 2018.
Non Final Office Action for U.S. Appl. No. 15/189,577 dated Sep. 28, 2018.
Non Final Office Action for U.S. Appl. No. 14/847,428 dated Sep. 23, 2016.
Non Final Office Action for U.S. Appl. No. 15/160,476 dated Sep. 15, 2017.
Final Office Action for U.S. Appl. No. 15/160,476 dated Apr. 23, 2018.
Non Final Office Action for U.S. Appl. No. 14/956,890 dated Nov. 25, 2016.
Final Office Action for U.S. Appl. No. 14/956,890 dated Jul. 24, 2018.
Non Final Office Action for U.S. Appl. No. 15/340,214 dated May 16, 2018.
Non Final Office Action for U.S. Appl. No. 14/629,965 dated Dec. 21, 2015.
Final Office Action for U.S. Appl. No. 14/629,965 dated Apr. 29, 2016.
Notice of Allowance for U.S. Appl. No. 14/629,965 dated Apr. 13, 2017.
Non Final Office Action for U.S. Appl. No. 15/445,225 dated Jun. 29, 2018.
Agheli, A. et al., "A Rare Case of Primary Amyloidosis, Presenting with Severe Pulmonary Hypertension and Bilateral Pleural Effusion," Blood, vol. 106: p. 5100 (2005).
Chaulagain, C.P., et al., "How we Treat Systemic Light-Chain Amyloidosis," Clinical Advances in Hematology & Oncology, vol. 13; No. 5; 315-324 (2015).
Chillemi, A. et al., "Anti-CD38 Antibody Therapy: Windows of Opportunity Yielded by the Functional Characteristics of the Target Molecule," Molecular Medicine, vol. 19; 99-108 (2013).
Eldfors, et al., "Landscape of Mutations in Relapsed Acute Myeloid Leukemia," vol. 124: No. 21, p. 2367; (2014).
Hu, Y., et al., "Immunophenotypic analysis of abnormal plasma cell clones in bone marrow of primary systemic light chain amyloidosis patients," Chin Med J., vol. 127; No. 15; 2765-2770; Abstract only (2014).
Hu, Y. et al., "The Significance of Abnormal Plasma Cell Clone in Bone Marrow of Primary Systemic Light Chain Amyloidosis Patients," Blood, vol. 122; p. 5342 (2013).
Kita, A., et al., "Sepantronium Bromide (YM155) Enhances Response of Human B-Cell Non-Hodgkin Lymphoma to Rituximab," The Journal of Pharmacology and Experimental Therapeutics, vol. 343; No. 1; 178-183 (2012).
Kong, S.Y., et al., "Daratumumab Directly Induces Human Multiple Myeloma Cell Death and Acts Synergistically with Conventional and Novel Anti-Myeloma Drugs," Blood, vol. 116; Abstract 3013 (2010).
Kumar, S. et al., "Expression of CD52 on plasma cells in plasma cell proliferative disorders," Blood, vol. 102; No. 3; 1075-1077 (2003).
Laubach, J.P., "Daratumumab granted breakthrough drug status," Expert Opinion Investig. Drugs, vol. 23; No. 4; 445-452 (2014).
Li, et al., "Creation of Patient Derived AML Xenografts Displaying Distinct Phenotypes and Geneotypes," Blood, vol. 122: No. 21, p. 5018 (2013).
Nijhof, I.S. et al., Combination of the anti-CD38 monoclonal antibody daratumumab and all-trans retinoic acid (Abstract in Proceedings of the AACR Special Conference on Hematologic Malignancies: Translating Discoveries to Novel Therapies). Clin Cancer Res, Sep. 20, 2014, vol. 21, No. 17 Suppl, pp. Abstract A12; Abstract.

(56) References Cited

OTHER PUBLICATIONS

Nijhof I.S. et al.: "Upregulation of CD38 expression on multiple myeloma cells by all-trans retinoic acid improves the efficacy of daratumumab", Leukemia, vol. 29, No. 10, ISSN 1476-5551, pp. 2039-2049 (2015).
Phase 1/2 Dose Escalation and Efficacy Study of Anti-CD38 Monoclonal Antibody in Patients With Selected CD38+ Hematological Malignancies, First posted Mar. 10, 2010, ClinicalTrials.gov. identifier No. NCT01084252.
Prosniak, M. et al.: "Development of a Cocktail of Recombinant-Expressed Human RabiesVirus-Neutralizing Monoclonal Antibodies for Postexposure Prophylaxis of Rabies," TheJournal of Infectious Diseases, vol. 187; 53-56 (2003).
Sachchithanantham, S. et al., "Use of Plasma Cell Immunophenotype as Prognostic Markers in Patients with Systemic AL Amyloidosis," Blood, vol. 122; p. 3120 (2013).
Schonland, S., et al., "Detection and Charaterization of Plasma Cell and B Cell Clones in Patients with Systemic Light Chain Amyloidosis Using Flow Cytometry," Blood, vol. 142, p. 2068 (2014).
Topalian, S.L., et al., "Immune Checkpoint Blockade: A Common Denominator Approach to Cancer Therapy," Cancer Cell, vol. 27; 450-461 (2015).
Weisel, K.C. et al., "Efficacy of daratumumab in combination with lenalidomide plus dexamethasone (DRd) or bortezomib plus dexamethasone (RVd) in relapsed or refractory multiple myeloma (RRMM) based on cytogenetic risk status," Journal of Clinical Oncology, vol. 35; No. 15; 8006; Abstract (2017).
Usmani, S.Z. et al., "Efficacy of Daratumumab, Lenalidomide, and Dexamethasone Versus Lenalidomide and Dexamethasone in Relapsed or Refractory Multiple Myeloma Patients with 1 to 3 Prior Lines of Therapy: Updated Analysis of Pollux," Blood, vol. 128; No. 22; 1151; 10 pages (2016).
Spencer, A. et al., "Daratumumab plus bortezomib and dexamethasone versus bortezomib and dexamethasone in relapsed or refractory multiple myeloma: updated analysis of CASTOR," Haematologica, vol. 103; No. 12; 2079-2087 (2018).
San-Miguel, J., "New approaches to myeloma treatment in 2017," EHA Learning Center; Abstract; 4 pages (2017).
Bahlis, N.J. et al., "Daratumumab, lenalidomide, and dexamethasone (DRd) vs lenalidomide and dexamethasone (Rd) in relapsed or refractory multiple myeloma (RRMM): Efficacy and safety updated (POLLUX)," Journal of Clinical Oncology, vol. 35; No. 15; 8025; Abstract (2017).
Dimopoulos, M.A. et al., "Daratumumab, Lenalidomide, and Dexamethasone for Multiple Myeloma," The New England Journal of Medicine, vol. 375; No. 14; 1319-1331 (2016).
Dimopoulos, M.A. et al., "Daratumumab plus lenalidomide and dexamethasone versus lenalidomide and dexamethasone in relapsed or refractory multiple myeloma: updated analysis of POLLUX," Haematologica, vol. 103; No. 12; 2088-2096 (2018).
Lakshman, A. et al., "Efficacy of daratumumab-based therapies in patients with relapsed, refractory multiple myeloma treated outside of clinical trials," Am J. Hematol., vol. 92; 1146-1155 (2017).
Palumbo, A. et al., "Daratumumab, Bortezomib, and Dexamethasone for Multiple Myeloma," The New England Journal of Medicine, vol. 375; No. 8; 754-766 (2016).
San-Miguel, J. et al., "Efficacy by cytogenetic risk status for daratumumab in combination with lenalidomide and dexamethasone or bortezomib and dexamethasone in relapsed or refractory multiple myeloma," EHA22; EHA Learning Center; Abstract; 4 pages (2017).
International Search Report and Written Opinion dated Feb. 12, 2019 for International Application No. PCT/US2018/058561, entitled "Methods of Treating High Risk Multiple Myeloma".
Non Final Office Action for U.S. Appl. No. 15/160,476 dated Nov. 5, 2018.
Final Office Action for U.S. Appl. No. 15/445,225 dated Dec. 17, 2018.
Non Final Office Action for U.S. Appl. No. 15/651,333 dated Sep. 27, 2018.
Final Office Action for U.S. Appl. No. 14/956,890 dated Jan. 14, 2019.
Notice of Allowance for U.S. Appl. No. 15/651,333 dated Feb. 21, 2019.
Krejcik, J. et al., "Daratumumab depletes CD38+ immune regulatory cells, promotes T-cell expansion, and skews T-cell repetoire in multiple myeloma," Blood, vol. 128; No. 3; 384-394 (2016).
Krejcik, J. et al., Immunomodulatory Effects and Adaptive Immune Response to Daratumumab in Multiple Myeloma,; Blood, vol. 126; 3037, 7 pages (2015).
Mauri, C. and Menon, M., "The expanding family of regulatory B cells," International Immunology, vol. 27; No. 10; 479-486 (2015).
Nijhof, I.S. et al., Preclinical Evidence for the Therapeutic Potential of CD38-Targeted. Immuno-Chemotherapy in Multiple Myeloma Patients Refractory to Lenalidomide and Bortezomib. Clin Cancer Res., vol. 21, No. 12, pp. 2802-2810 (2014).
Patton, D.T. et al., "The P13K p110δ Regulates Expression of CD38 on Regulatory T Cells," PLOS one, vol. 6; No. 3; e17359; 8 pages (2011).
Sher, T. et al., "First report of safety and efficacy of daratumumab in 2 cases of advanced immunoglobulin light chain amyloidosis," Blood, vol. 128; No. 15; 1987-1989 (2016).
Talmadge, J.E. and Gabrilovich, D.I, "History of myeloid-derived suppressor cells," Nature Reviews, vol. 13; 739-752 (2013).
Notice of Allowance for U.S. Appl. No. 15/189,577 dated Mar. 5, 2019.
Final Office Action for U.S. Appl. No. 15/340,290 dated Mar. 11, 2019.
Notice of Allowance for U.S. Appl. No. 15/340,290 dated May 22, 2019.
Notice of Allowance for U.S. Appl. No. 15/651,333 dated May 31, 2019.
Final Office Action for U.S. Appl. No. 15/160,476 dated Jun. 14, 2019.
Abdi, J. et al., "Drug resistance in multiple myeloma: latest findings and new concepts on molecular mechanisms," Oncotarget, vol. 4; No. 12; 2186-2207 (2013).
Chaulagain, C.P. and Comenzo, R.L., "New Insights and Modern Treatment of AL Amyloidosis," Curr Hematol Malig Rep, vol. 8; 291-298 (2013).
Chiarugi, A. et al., "The NAD metabolome—a key determinant of cancel cell biology," Nature Reviews, vol. 12; 741-752 (2012).
Comenzo, R.L. et al., "Consensus guidelines for the conduct and reporting of clinical trials in systemic light-chain amyloidosis," Leukemia, vol. 26; 2317-2325 (2012).
Ettinger, R. et al., "Pathogenic mechanisms of IgE-mediated inflammation in self-destructive autoimmune responses," Autoimmunity, vol. 50; No. 1; 25-36 (2017).
Gupta, R. et al., "The Economic Impact of Childhood Food Allergy in the United States," JAMA Pediatrics, vol. 167; No. 11; 1026-1031 (2013).
Holgate, S.T., "New strategies with anti-IgE in allergic diseases," World Allergy Organization Journal, vol. 7; No. 17; 6 pages (2014).
Inaba, H. et al., "Acute lymphoblastic leukaemia," Lancet, vol. 381; 27 pages (2013).
Lepenies, B. and Jacobs, T., "The Role of Negative Costimulators During Parasitic Infections," Endocrine, Metabolic & Immune Disorders—Drug Targets, vol. 8; 279-288 (2008).
Manier, S. et al., "Bone Marrow Microenvironment in Multiple Myeloma Progession," Journal of Biomedicine and Biotechnology, vol. 2012; 5 pages (2012).
Merlini, G. and Bellotti, V., "Molecular Mechanisms of Amyloidosis," The New England Journal of Medicine, vol. 349; No. 6; 583-596 (2003).
Mills, E.N.C. et al., "The prevalence, cost and basis of food allergy across Europe," Allergy, vol. 62; 717-722 (2007).
Patel, J.P., "Prognostic Relevance of Integrated Genetic Profiling in Acute Myeloid Leukemia," The New England Journal of Medicine, vol. 366; No. 12; 1079-1089 (2012).
Sicherer, S.H. and Sampson, H.A., "Food allergy: Epidemiology, pathogenesis, diagnosis, and treatment," J. Allergy Clin Inmmunol, vol. 133; 291-307 (2014).

(56) References Cited

OTHER PUBLICATIONS

Swaika, A. et al., "Current state of anti-PD-L1 and anti-PD-1 agents in cancer therapy," Molecular Immunology, vol. 67; 4-17 (2015).
The Cancer Genome Atlas Research Network et al., "Genomic and Epigenomic Landscapes of Adult De Novo Acute Myeloid Leukemia," N. Engl. J. Med, vol. 368; No. 22; 2059-2074 (2013).
Wang, L. et al., "VISTA, a novel mouse Ig superfamily ligand that negatively regulates T cell responses," J. Exp. Med., vol. 208; No. 3; 577-592 (2011).
Wei, W. et al., "Roles and mechanisms of the CD38/cyclic adenosine diphosphate ribose/Ca2+ signaling pathway," World Journal of Biological Chemistry, vol. 5; No. 1; 58-67 (2014).
Notice of Allowance for U.S. Appl. No. 15/445,225 dated Jul. 29, 2019.
Non-Final Office Action for U.S. Appl. No. 14/956,890 dated Jul. 30, 2019.
Notice of Allowance for U.S. Appl. No. 15/189,577 dated Sep. 12, 2019.
Notice of Allowance for U.S. Appl. No. 15/651,333 dated Oct. 9, 2019.

* cited by examiner

COMBINATION THERAPIES WITH ANTI-CD38 ANTIBODIES

CROSS-REFERENCE TO RELATED APPLICATIONS

This application is a continuation of U.S. application Ser. No. 14/847,428, filed 8 Sep. 2015, currently pending, which claims the benefit of U.S. Provisional Application Ser. No. 62/087,287 filed 4 Dec. 2014 and U.S. Provisional Application Ser. No. 62/047,877, filed 9 Sep. 2014, the entire contents of which are incorporated herein by reference.

FIELD OF THE INVENTION

The present invention relates to combination therapies with anti-CD38 antibodies and all-trans retinoic acid.

BACKGROUND OF THE INVENTION

B-cell malignancies include B-cell chronic lymphocytic leukemia, mantle cell lymphoma, Burkitt lymphoma, follicular lymphoma, diffuse large B-cell lymphoma, multiple myeloma, Hodgkin's lymphoma, hairy cell leukemia, primary effusion lymphoma and AIDS-related Non-Hodgkin's Lymphoma. B-cell malignancies comprise more than 85% of diagnosed lymphomas.

Multiple myeloma (MM) is a B cell malignancy characterized by the latent accumulation of secretory plasma cells in bone marrow with a low proliferative index and an extended life span. The disease ultimately attacks bones and bone marrow, resulting in multiple tumors and lesions throughout the skeletal system. Approximately 1% of all cancers, and slightly more than 10% of all hematologic malignancies, can be attributed to MM. Incidence of MM increases in the aging population, with the median age at time of diagnosis being about 61 years.

CD38 is a type II membrane protein having function in receptor-mediated adhesion and signaling as well as mediating calcium mobilization via its ecto-enzymatic activity, catalyzing formation of cyclic ADP-ribose (cADPR) from $NAD^+$ and also hydrolyzing cADPR into ADP-ribose (ADPR). CD38 mediates cytokine secretion and activation and proliferation of lymphocytes (Funaro et al., J Immunology 145:2390-6, 1990; Terhorst et al., Cell 771-80, 1981; Guse et al., Nature 398:70-3, 1999), and via its NAD glycohydrolase activity regulates extracellular $NAD^+$ levels which have been implicated in modulating the regulatory T-cell compartment (Adriouch et al., 14:1284-92, 2012; Chiarugi et al., Nature Reviews 12:741-52, 2012).

CD38 is expressed on MM malignant plasma cells, and is implicated in various hematological malignancies.

Currently available therapies for MM include chemotherapy, stem cell transplantation, Thalomid® (thalidomide), Revlimid® (lenalidomide), Velcade® (bortezomib), Aredia® (pamidronate), and Zometa® (zoledronic acid). Current treatment protocols, which include a combination of chemotherapeutic agents such as vincristine, BCNU, melphalan, cyclophosphamide, adriamycin, and prednisone or dexamethasone, yield a complete remission rate of only about 5%. Median survival is approximately 36-48 months from the time of diagnosis. Recent advances using high dose chemotherapy followed by autologous bone marrow or peripheral blood mononuclear cell transplantation have increased the complete remission rate and remission duration, yet overall survival has only been slightly prolonged, and no evidence for a cure has been obtained. Ultimately, all MM patients relapse, even under maintenance therapy with interferon-alpha (IFN-α) alone or in combination with steroids. Thus, there is a need for additional therapies for the treatment of multiple myeloma and other B-cell malignancies.

SUMMARY OF THE INVENTION

One embodiment of the invention is a method of treating a subject having a CD38-positive hematological malignancy, comprising administering to a patient in need thereof an anti-CD38 antibody in combination with all-trans retinoic acid (ATRA), wherein the anti-CD38 antibody induces killing of CD38-expressing cells in vitro by antibody-dependent cell-mediated cytotoxicity (ADCC) or complement dependent cytotoxicity (CDC).

DETAILED DESCRIPTION OF THE INVENTION

Figure 1A:
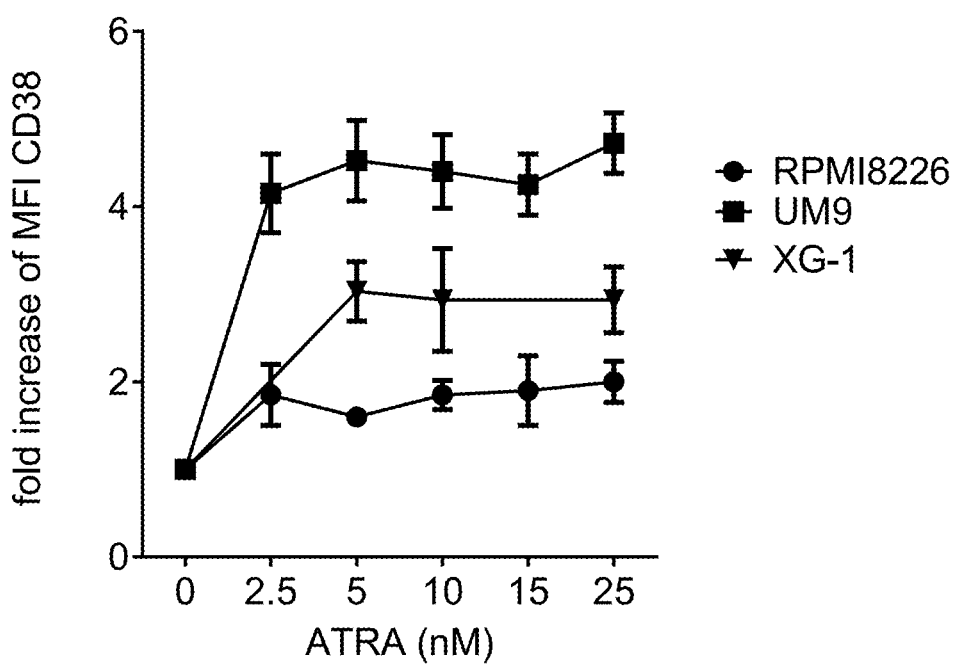
FIG. 1A shows that all-trans retinoic acid (ATRA) enhances CD38 expression on multiple myeloma (MM) cell lines in a dose dependent manner MM cell lines RPMI8226, UM9 and XG1 were incubated with RPMI-1640 medium alone or with 0-25 nM ATRA for 48 hours and then harvested to determine CD38 expression by flow cytometry. The graph shows results of one representative experiment. The Y axis shows the fold increase of mean fluorescent intensity (MFI) of CD38 surface expression.

"CD38" refers to the human CD38 protein (synonyms: ADP-ribosyl cyclase 1, cADPr hydrolase 1, Cyclic ADP-ribose hydrolase 1). Human CD38 has the amino acid sequence shown in SEQ ID NO: 1

"Antibodies" as used herein is meant in a broad sense and includes immunoglobulin molecules including, monoclonal antibodies including murine, human, human-adapted, humanized and chimeric monoclonal antibodies, antibody fragments, bispecific or multispecific antibodies, dimeric, tetrameric or multimeric antibodies, and single chain antibodies.

Immunoglobulins can be assigned to five major classes, namely IgA, IgD, IgE, IgG and IgM, depending on the heavy chain constant domain amino acid sequence. IgA and IgG are further sub-classified as the isotypes $IgA_1$, $IgA_2$, $IgG_1$, $IgG_2$, $IgG_3$ and $IgG_4$. Antibody light chains of any vertebrate species can be assigned to one of two clearly distinct types, namely kappa (κ) and lambda (λ), based on the amino acid sequences of their constant domains.

"Antibody fragments" as used herein refers to a portion of an immunoglobulin molecule that retains the heavy chain and/or the light chain antigen binding site, such as heavy chain complementarity determining regions (HCDR) 1, 2 and 3, light chain complementarity determining regions (LCDR) 1, 2 and 3, a heavy chain variable region (VH), or a light chain variable region (VL). Antibody fragments include a Fab fragment, a monovalent fragment consisting of the VL, VH, CL and CH1 domains, a F(ab)₂ fragment, a bivalent fragment comprising two Fab fragments linked by a disulfide bridge at the hinge region, a Fd fragment consisting of the VH and CH1 domains; a Fv fragment consisting of the VL and VH domains of a single arm of an antibody, a domain antibody (dAb) (Ward et al., Nature 341:544-546, 1989), which consists of a VH domain. VH and VL domains can be engineered and linked together via a synthetic linker to form various types of single chain antibody designs where the VH/VL domains pair intramolecularly, or intermolecularly in those cases when the VH and VL domains are expressed by separate single chain antibody constructs, to form a monovalent antigen binding site, such as single chain Fv (scFv) or diabody; described for example in Intl. Pat. Publ. Nos. WO1998/44001, WO1988/01649, WO1994/13804, and WO1992/01047. These antibody fragments are obtained using well known techniques known to those of skill in the art, and the fragments are screened for utility in the same manner as are full length antibodies.

"Isolated antibody" as used herein refers to an antibody or antibody fragment that is substantially free of other antibodies having different antigenic specificities (e.g., an antibody that specifically binds CD38). An isolated antibody that specifically binds CD38, however, may have cross-reactivity to other antigens, such as orthologs of human CD38 such as *Macaca fascicularis* (cynomolgus) CD38. Moreover, an isolated antibody may be substantially free of other cellular material and/or chemicals.

An antibody variable region consists of a "framework" region interrupted by three "antigen binding sites". The antigen binding sites are defined using various terms: Complementarity Determining Regions (CDRs), three in the VH (HCDR1, HCDR2, HCDR3), and three in the VL (LCDR1, LCDR2, LCDR3) are based on sequence variability (Wu and Kabat J Exp Med 132:211-50, 1970; Kabat et al Sequences of Proteins of Immunological Interest, 5th Ed. Public Health Service, National Institutes of Health, Bethesda, Md., 1991); "Hypervariable regions", "HVR", or "HV", three in the VH (H1, H2, H3) and three in the VL (L1, L2, L3) refer to the regions of an antibody variable domains which are hypervariable in structure as defined by Chothia and Lesk (Chothia and Lesk Mol Biol 196:901-17, 1987). Other terms include "IMGT-CDRs" (Lefranc et al., Dev Comparat Immunol 27:55-77, 2003) and "Specificity Determining Residue Usage" (SDRU) (Almagro, Mol Recognit 17:132-43, 2004). The International ImMunoGeneTics (IMGT) database (http://www_imgt_org) provides a standardized numbering and definition of antigen-binding sites. The correspondence between CDRs, HVs and IMGT delineations is described in Lefranc et al., Dev Comparat Immunol 27:55-77, 2003.

"Chothia residues" as used herein are the antibody VL and VH residues numbered according to Al-Lazikani (Al-Lazikani et al., J Mol Biol 273:927-48, 1997).

"Framework" or "framework sequences" are the remaining sequences of a variable region other than those defined to be antigen binding sites.

"Humanized antibody" refers to an antibody in which the antigen binding sites are derived from non-human species and the variable region frameworks are derived from human immunoglobulin sequences. Humanized antibodies may include substitutions in the framework so that the framework may not be an exact copy of expressed human immunoglobulin or germline gene sequences.

"Human-adapted" antibodies or "human framework adapted (HFA)" antibodies refers to humanized antibodies adapted according to methods described in U.S. Pat. Publ. No. US2009/0118127. Human-adapted antibodies are humanized by selecting the acceptor human frameworks based on the maximum CDR and FR similarities, length compatibilities and sequence similarities of CDR1 and CDR2 loops and a portion of light chain CDR3 loops.

"Human antibody" refers to an antibody having heavy and light chain variable regions in which both the framework and the antigen binding sites are derived from sequences of human origin. If the antibody contains a constant region, the constant region also is derived from sequences of human origin.

A human antibody comprises heavy or light chain variable regions that are "derived from" sequences of human origin where the variable regions of the antibody are obtained from a system that uses human germline immunoglobulin or rearranged immunoglobulin genes. Such systems include human immunoglobulin gene libraries displayed on phage, and transgenic non-human animals such as mice carrying human immunoglobulin loci as described herein. A human antibody may contain amino acid differences when compared to the human germline or rearranged immunoglobulin sequences due to for example naturally occurring somatic mutations or intentional introduction of substitutions in the framework or antigen binding sites. Typically, a human antibody is at least about 80%, 81%, 82%, 83%, 84%, 85%, 86%, 87%, 88%, 89%, 90%, 91%, 92%, 93%, 94%, 95%, 96%, 97%, 98%, 99% or 100% identical in amino acid sequence to an amino acid sequence encoded by a human germline or rearranged immunoglobulin gene. In some cases, a human antibody may contain consensus framework sequences derived from human framework sequence analyses, for example as described in Knappik et al., J Mol Biol 296:57-86, 2000), or synthetic HCDR3 incorporated into human immunoglobulin gene libraries displayed on phage, for example as described in Shi et al., J Mol Biol 397:385-96, 2010 and Intl. Pat. Publ. No. WO2009/085462). Antibodies in which antigen binding sites are derived from a non-human species are not included in the definition of human antibody.

Isolated humanized antibodies may be synthetic. Human antibodies may be generated using systems such as phage display incorporating synthetic CDRs and/or synthetic frameworks, or can be subjected to in vitro mutagenesis to improve antibody properties.

"Recombinant antibody" as used herein includes all antibodies that are prepared, expressed, created or isolated by recombinant means, such as antibodies isolated from an animal (e.g., a mouse or a rat) that is transgenic or transchromosomal for human immunoglobulin genes or a hybridoma prepared therefrom (described further below), antibodies isolated from a host cell transformed to express the antibody, antibodies isolated from a recombinant combinatorial antibody library, and antibodies prepared, expressed, created or isolated by any other means that involve splicing of human immunoglobulin gene sequences to other DNA sequences, or antibodies that are generated in vitro using Fab arm exchange such as bispecific antibodies.

"Monoclonal antibody" as used herein refers to a preparation of antibody molecules of single molecular composition. A monoclonal antibody composition displays a single binding specificity via its VH, VL and/or VH/VL pair and affinity for a particular epitope, or in a case of a bispecific monoclonal antibody, a dual binding specificity to two distinct epitopes.

"Epitope" as used herein means a portion of an antigen to which an antibody specifically binds. Epitopes usually consist of chemically active (such as polar, non-polar or hydrophobic) surface groupings of moieties such as amino acids or polysaccharide side chains and can have specific three-dimensional structural characteristics, as well as specific charge characteristics. An epitope may be composed of contiguous and/or noncontiguous amino acids that form a conformational spatial unit. For a noncontiguous epitope, amino acids from differing portions of the linear sequence of the antigen come in close proximity in 3-dimensional space through the folding of the protein molecule.

"Variant" as used herein refers to a polypeptide or a polynucleotide that differs from a reference polypeptide or a reference polynucleotide by one or more modifications for example, substitution, insertion or deletion.

"Synergy", "synergism" or "synergistic" mean more than the expected additive effect of a combination.

"In combination with" as used herein means that two or more therapeutics maybe administered to a subject together in a mixture, concurrently as single agents or sequentially as single agents in any order.

The terms "treat" or "treatment" refer to therapeutic treatment wherein the object is to slow down (lessen) an undesired physiological change or disease, or provide a beneficial or desired clinical outcome during treatment, such as the development, growth or spread of tumor or tumor cells. Beneficial or desired clinical outcomes include alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if a subject was not receiving treatment. Those in need of treatment include those subjects already with the undesired physiological change or diseaseas well as those subjects prone to have the physiological change or disease.

"Inhibits growth" (e.g., referring to cells, such as tumor cells) refers to a measurable decrease in the cell growth in vitro or in vivo when contacted with a therapeutic or a combination of therapeutics or drugs when compared to the growth of the same cells grown in appropriate control conditions well known to the skilled in the art. Inhibition of growth of a cell in vitro or in vivo may be at least about 10%, 20%, 30%, 40%, 50%, 60%, 70%, 80%, 90%, 99%, or 100% Inhibition of cell growth may occur by a variety of mechanisms, for example by antibody-dependent cell-mediated toxicity (ADCC), antibody dependent cellular phagocytosis (ADCP), complement dependent cytotoxicity (CDC), apoptosis, necrosis, or inhibition of cell proliferation.

A "therapeutically effective amount" refers to an amount effective, at dosages and for periods of time necessary, to achieve a desired therapeutic result. A therapeutically effective amount may vary according to factors such as the disease state, age, sex, and weight of the individual, and the ability of a therapeutic or a combination of therapeutics to elicit a desired response in the individual. Exemplary indicators of an effective therapeutic or combination of therapeutics that include, for example, improved well-being of the patient, reduction of a tumor burden, arrested or slowed growth of a tumor, and/or absence of metastasis of cancer cells to other locations in the body.

The invention provides methods for treating patients having CD38-positive hematological malignancy with the combination of a CD38 antibody and all-trans retinoic acid (ATRA). The invention is based, at least in part, on the discovery that ATRA augments anti-CD38 antibody daratumumab-mediated lysis by ADCC and/or CDC of primary MM cells expressing low, intermediate or high levels of CD38 by enhancing CD38 expression on MM cells. ATRA is also able to induce daratumumab-mediated ADCC and/or CDC in primary MM samples which were resistant to daratumumab-mediated CDC and/or ADCC in vitro or were obtained from heavily pretreated multiple myeloma patients having double-refractory (lenalidomide- and bortezomib-refractory) disease. ATRA augmented daratumumab-mediated CDC to a higher extent than ADCC, which may be explained by the findings that ATRA also down-regulates complement-inhibitory proteins CD55 and CD59.

ATRA (CAS 302-79-4) has a well-known molecular structure.

One embodiment of the invention disclosed herein, including in the numbered embodiments listed below, is a method of treating a subject having a CD38-positive hematological malignancy, comprising administering to the subject in need thereof an anti-CD38 antibody in combination with all-trans retinoic acid (ATRA).

One embodiment of the invention disclosed herein, including in the numbered embodiments listed below, is a method of treating a subject having a CD38-positive hematological malignancy, comprising administering to the subject in need thereof an anti-CD38 antibody in combination with all-trans retinoic acid (ATRA), wherein the anti-CD38 antibody induces killing of CD38-expressing cells in vitro by antibody-dependent cell-mediated cytotoxicity (ADCC) or complement dependent cytotoxicity (CDC).

The methods of the invention may be used to treat an animal subject belonging to any classification. Examples of such animals include mammals such as humans, rodents, dogs, cats and farm animals.

In some embodiments of the invention disclosed herein, including in the numbered embodiments listed below, the anti-CD38 antibody induces killing of the CD38-expressing cells by CDC in vitro.

"CD38-positive hematological malignancy" refers to a hematological malignancy characterized by the presence of tumor cells expressing CD38 including leukemias, lymphomas and myeloma. Examples of such CD38-positive hematological malignancies are precursor B-cell lymphoblastic leukemia/lymphoma and B-cell non-Hodgkin's lymphoma, acute promyelocytic leukemia, acute lymphoblastic leukemia and mature B-cell neoplasms, such as B-cell chronic lymphocytic leukemia (CLL)/small lymphocytic lymphoma (SLL), B-cell acute lymphocytic leukemia, B-cell prolymphocytic leukemia, lymphoplasmacytic lymphoma, mantle cell lymphoma (MCL), follicular lymphoma (FL), including low-grade, intermediate-grade and high-grade FL, cutaneous follicle center lymphoma, marginal zone B-cell lymphoma (MALT type, nodal and splenic type), hairy cell leukemia, diffuse large B-cell lymphoma (DLBCL), Burkitt's lymphoma (BL), plasmacytoma, multiple myeloma (MM), plasma cell leukemia, post-transplant lymphoproliferative disorder, Waldenstrom's macroglobulinemia, plasma cell leukemias and anaplastic large-cell lymphoma (ALCL).

CD38 is expressed in a variety of malignant hematological diseases, including multiple myeloma, leukemias and lymphomas, such as B-cell chronic lymphocytic leukemia, T- and B-cell acute lymphocytic leukemia, Waldenstrom macroglobulinemia, primary systemic amyloidosis, mantle-cell lymphoma, pro-lymphocytic/myelocytic leukemia, acute myeloid leukemia, chronic myeloid leukemia, follicular lymphoma, Burkitt's lymphoma, large granular lymphocytic (LGL) leukemia, NK-cell leukemia and plasma-cell leukemia. Expression of CD38 has been described on epithelial/endothelial cells of different origin, including glandular epithelium in prostate, islet cells in pancreas, ductal epithelium in glands, including parotid gland, bronchial epithelial cells, cells in testis and ovary and tumor epithelium in colorectal adenocarcinoma. Other diseases, where CD38 expression could be involved, include, e.g., bronchoepithelial carcinomas of the lung, breast cancer (evolving from malignant proliferation of epithelial lining in ducts and lobules of the breast), pancreatic tumors, evolving from the β-cells (insulinomas), tumors evolving from epithelium in the gut (e.g. adenocarcinoma and squamous cell carcinoma), carcinoma in the prostate gland, and seminomas in testis and ovarian cancers. In the central nervous system, neuroblastomas express CD38.

In one embodiment of the invention disclosed herein, including in the numbered embodiments listed below, the CD38-positive hematological malignancy is multiple myeloma.

In one embodiment of the invention disclosed herein, including in the numbered embodiments listed below, the CD38-positive hematological malignancy is diffuse large B-cell lymphoma (DLBCL).

In one embodiment of the invention disclosed herein, including in the numbered embodiments listed below, the CD38-positive hematological malignancy is non-Hodgkin's lymphoma.

In one embodiment of the invention disclosed herein, including in the numbered embodiments listed below, the CD38-positive hematological malignancy is acute lymphoblastic leukemia (ALL).

In one embodiment of the invention disclosed herein, including in the numbered embodiments listed below, the CD38-positive hematological malignancy is follicular lymphoma (FL).

In one embodiment of the invention disclosed herein, including in the numbered embodiments listed below, the CD38-positive hematological malignancy is Burkitt's lymphoma (BL).

In one embodiment of the invention disclosed herein, including in the numbered embodiments listed below, the CD38-positive hematological malignancy is mantle cell lymphoma (MCL).

In one embodiment of the invention disclosed herein, including in the numbered embodiments listed below, the CD38-positive hematological malignancy is multiple myeloma, acute lymphoblastic leukemia (ALL), non-Hodgkin's lymphoma, diffuse large B-cell lymphoma (DLBCL), Burkitt's lymphoma (BL), follicular lymphoma (FL) or mantle-cell lymphoma (MCL).

Examples of B-cell non-Hodgkin's lymphomas are lymphomatoid granulomatosis, primary effusion lymphoma, intravascular large B-cell lymphoma, mediastinal large B-cell lymphoma, heavy chain diseases (including γ, μ, and a disease), lymphomas induced by therapy with immunosuppressive agents, such as cyclosporine-induced lymphoma, and methotrexate-induced lymphoma.

In one embodiment of the present invention, including in the numbered embodiments listed below the disorder involving cells expressing CD38 is Hodgkin's lymphoma.

Other examples of disorders involving cells expressing CD38 include malignancies derived from T and NK cells including mature T cell and NK cell neoplasms including T-cell prolymphocytic leukemia, T-cell large granular lymphocytic leukemia, aggressive NK cell leukemia, adult T-cell leukemia/lymphoma, extranodal NK/T cell lymphoma, nasal type, enteropathy-type T-cell lymphoma, hepatosplenic T-cell lymphoma, subcutaneous panniculitis-like T-cell lymphoma, blastic NK cell lymphoma, Mycosis Fungoides/Sezary Syndrome, primary cutaneous CD30 positive T-cell lymphoproliferative disorders (primary cutaneous anaplastic large cell lymphoma C-ALCL, lymphomatoid papulosis, borderline lesions), angioimmunoblastic T-cell lymphoma, peripheral T-cell lymphoma unspecified, and anaplastic large cell lymphoma.

Examples of malignancies derived from myeloid cells include acute myeloid leukemia, including acute promyelocytic leukemia, and chronic myeloproliferative diseases, including chronic myeloid leukemia.

Any anti-CD38 antibody may be used in the methods of the invention as disclosed herein, including in the numbered embodiments listed below.

In some embodiments, the anti-CD38 antibody induces in vitro killing of CD38-expressing cells by antibody-dependent cell-mediated cytotoxicity (ADCC) and/or complement dependent cytotoxicity (CDC).

The variable regions of the anti-CD38 antibodies may be obtained from existing anti-CD38 antibodies, and cloned as full length antibodies or into various antibody formats and fragments using standard methods. Exemplary variable regions binding CD38 that may be used are described in Intl. Pat. Publ. Nos. WO05/103083, WO06/125640, WO07/042309, WO08/047242, WO12/092612, WO06/099875 and WO11/154453A1.

An exemplary anti-CD38 antibody that may be used is daratumumab. Daratumumab comprises the heavy chain variable region (VH) and the light chain variable region (VL) amino acid sequences shown in SEQ ID NO: 4 and 5, respectively, heavy chain CDRs HCDR1, HCDR2 and HCDR3 of SEQ ID NOs: 6, 7 and 8, respectively, and light chain CDRs LCDR1, LCDR2 and LCDR3 of SEQ ID NOs: 9, 10 and 11, respectively, and is of IgG1/κ subtype and described in U.S. Pat. No. 7,829,693. Daratumumab heavy chain amino acid sequence is shown in SEQ ID NO: 12 and light chain amino acid sequence shown in SEQ ID NO: 13.

```
                                              SEQ ID NO: 1
MANCEFSPVSGDKPCCRLSRRAQLCLGVSILVLILVVVLAVVVPRWRQQW
SGPGTTKRFPETVLARCVKYTEIHPEMRHVDCQSVWDAFKGAFISKHPCN
ITEEDYQPLMKLGTQTVPCNKILLWSRIKDLAHQFTQVQRDMFTLEDTLL
GYLADDLTWCGEFNTSKINYQSCPDWRKDCSNNPVSVFWKTVSRRFAEAA
CDVVHVMLNGSRSKIFDKNSTFGSVEVHNLQPEKVQTLEAWVIHGGREDS
RDLCQDPTIKELESIISKRNIQFSCKNIYRPDKFLQCVKNPEDSSCTSEI

SEQ ID NO: 2
SKRNIQFSCKNIYR

SEQ ID NO: 3
EKVQTLEAWVIHGG

SEQ ID NO: 4
EVQLLESGGGLVQPGGSLRLSCAVSGFTFNSFAMSWVRQAPGKGLEWVSA
ISGSGGGTYYADSVKGRFTISRDNSKNTLYLQMNSLRAEDTAVYFCAKDK
ILWFGEPVFDYWGQGTLVTVSS

SEQ ID NO: 5
EIVLTQSPATLSLSPGERATLSCRASQSVSSYLAWYQQKPGQAPRLLIYD
ASNRATGIPARFSGSGSGTDFTLTISSLEPEDFAVYYCQQRSNWPPTFGQ
GTKVEIK

SEQ ID NO: 6
SFAMS

SEQ ID NO: 7
AISGSGGGTYYADSVKG

SEQ ID NO: 8
DKILWFGEPVFDY

SEQ ID NO: 9
RASQSVSSYLA

SEQ ID NO: 10
DASNRAT

SEQ ID NO: 11
QQRSNWPPTF

SEQ ID NO: 12
EVQLLESGGGLVQPGGSLRLSCAVSGFTFNSFAMSWVRQAPGKGLEWVSA
ISGSGGGTYYADSVKGRFTISRDNSKNTLYLQMNSLRAEDTAVYFCAKDK
ILWFGEPVFDYWGQGTLVTVSSASTKGPSVFPLAPSSKSTSGGTAALGCL
VKDYFPEPVTVSWNSGALTSGVHTFPAVLQSSGLYSLSSVVTVPSSSLGT
QTYICNVNHKPSNTKVDKRVEPKSCDKTHTCPPCPAPELLGGPSVFLFPP
KPKDTLMISRTPEVTCVVVDVSHEDPEVKFNWYVDGVEVHNAKTKPREEQ
YNSTYRVVSVLTVLHQDWLNGKEYKCKVSNKALPAPIEKTISKAKGQPRE
PQVYTLPPSREEMTKNQVSLTCLVKGFYPSDIAVEWESNGQPENNYKTTP
PVLDSDGSFFLYSKLTVDKSRWQQGNVFSCSVMHEALHNHYTQKSLSLSP
GK

SEQ ID NO: 13
EIVLTQSPATLSLSPGERATLSCRASQSVSSYLAWYQQKPGQAPRLLIYD
ASNRATGIPARFSGSGSGTDFTLTISSLEPEDFAVYYCQQRSNWPPTFGQ
GTKVEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQG
LSSPVTKSFNRGEC
```

Another exemplary anti-CD38 antibody that may be used is mAb003 comprising the VH and VL sequences of SEQ ID NOs: 14 and 15, respectively and described in U.S. Pat. No. 7,829,693. The VH and the VL of mAb003 may be expressed as IgG1/κ.

```
                                              SEQ ID NO: 14
QVQLVQSGAEVKKPGSSVKVSCKASGGTFSSYAFSWVRQAPGQGLEWMGR
VIPFLGIANSAQKFQGRVTITADKSTSTAYMDLSSLRSEDTAVYYCARDD
IAALGPFDYWGQGTLVTVSSAS

SEQ ID NO: 15
DIQMTQSPSSLSASVGDRVTITCRASQGISSWLAWYQQKPEKAPKSLIYA
ASSLQSGVPSRFSGSGSGTDFTLTISSLQPEDFATYYCQQYNSYPRTFGQ
GTKVEIK
```

Another exemplary anti-CD38 antibody that may be used is mAb024 comprising the VH and VL sequences of SEQ ID NOs: 16 and 17, respectively, described in U.S. Pat. No. 7,829,693. The VH and the VL of mAb024 may be expressed as IgG1/κ.

```
                                              SEQ ID NO: 16
EVQLVQSGAEVKKPGESLKISCKGSGYSFSNYWIGWVRQMPGKGLEWMG
HYPHDSDARYSPSFQGQVTFSADKSISTAYLQWSSLKASDTAMYYCARH
VGWGSRYWYFDLWGRGTLVTVSS

SEQ ID NO: 17
EIVLTQSPATLSLSPGERATLSCRASQSVSSYLAWYQQKPGQAPRLLIY
DASNRATGIPARFSGSGSGTDFTLTISSLEPEDFAVYYCQQRSNWPPTF
GQGTKVEIK
```

Another exemplary anti-CD38 antibody that may be used is MOR-202 (MOR-03087) comprising the VH and VL sequences of SEQ ID NOs: 18 and 19, respectively, described in U.S. Pat. No. 8,088,896. The VH and the VL of MOR-202 may be expressed as IgG1/κ.

SEQ ID NO: 18
QVQLVESGGGLVQPGGSLRLSCAASGFTFSSYYMNWVRQAPGKGLEWV
SGISGDPSNTYYADSVKGRFTISRDNSKNTLYLQMNSLRAEDTAVYYC
ARDLPLVYTGFAYWGQGTLVTVSS

SEQ ID NO: 19
DIELTQPPSVSVAPGQTARISCSGDNLRHYVVYWYQQKPGQAPVLVIY
GDSKRPSGIPERFSGSNSGNTATLTISGTQAEDEADYYCQTYTGGASL
VFGGGTKLTVLGQ

Another exemplary anti-CD38 antibody that may be used is Isatuximab comprising the VH and VL sequences of SEQ ID NOs: 20 and 21, respectively, described in U.S. Pat. No. 8,153,765. The VH and the VL of Isatuximab may be expressed as IgG1/κ.

SEQ ID NO 20:
QVQLVQSGAEVAKPGTSVKLSCKASGYTFTDYWMQWVKQRPGQGLEWIGT
IYPGDGDTGYAQKFQGKATLTADKSSKTVYMHLSSLASEDSAVYYCARGD
YYGSNSLDYWGQGTSVTVSS

SEQ ID NO: 21:
DIVMTQSHLSMSTSLGDPVSITCKASQDVSTVVAWYQQKPGQSPRRLIYS
ASYRYIGVPDRFTGSGAGTDFTFTISSVQAEDLAVYYCQQHYSPPYTFGG
GTKLEIK

Other exemplary anti-CD38 antibodies that may be used in the methods of the invention include those described in Int. Pat. Publ. No. WO05/103083, Intl. Pat. Publ. No. WO06/125640, Intl. Pat. Publ. No. WO07/042309, Intl. Pat. Publ. No. WO08/047242 or Intl. Pat. Publ. No. WO14/178820.

Anti-CD38 antibodies used in the methods of the invention disclosed herein, including in the numbered embodiments listed below, may also be selected de novo from a phage display library, where the phage is engineered to express human immunoglobulins or portions thereof such as Fabs, single chain antibodies (scFv), or unpaired or paired antibody variable regions (Knappik et al., J Mol Biol 296:57-86, 2000; Krebs et al., J Immunol Meth 254:67-84, 2001; Vaughan et al., Nature Biotechnology 14:309-314, 1996; Sheets et al., PITAS (USA) 95:6157-6162, 1998; Hoogenboom and Winter, J Mol Biol 227:381, 1991; Marks et al., J Mol Biol 222:581, 1991). CD38 binding variable domains may be isolated from for example phage display libraries expressing antibody heavy and light chain variable regions as fusion proteins with bacteriophage pIX coat protein as described in Shi et al., J. Mol. Biol. 397:385-96, 2010 and PCT Intl. Publ. No. WO09/085462). The antibody libraries may be screened for binding to human CD38 extracellular domain, obtained positive clones further characterized, Fabs isolated from the clone lysates, and subsequently cloned as full length antibodies. Such phage display methods for isolating human antibodies are established in the art. See for example: U.S. Pat. Nos. 5,223,409; 5,403,484; and 5,571,698, 5,427,908, 5,580,717, 5,969,108, 6,172,197, 5,885,793; 6,521,404; 6,544,731; 6,555,313; 6,582,915; and 6,593,081.

The Fc portion of the antibody may mediate antibody effector functions such as antibody-dependent cell-mediated cytotoxicity (ADCC), antibody-dependent cellular phagocytosis (ADCP) or complement dependent cytotoxicity (CDC). Such functions may be mediated by binding of an Fc effector domain(s) to an Fc receptor on an immune cell with phagocytic or lytic activity or by binding of an Fc effector domain(s) to components of the complement system. Typically, the effect(s) mediated by the Fc-binding cells or complement components result in inhibition and/or depletion of target cells, e.g., CD38-expressing cells. Human IgG isotypes IgG1, IgG2, IgG3 and IgG4 exhibit differential capacity for effector functions. ADCC may be mediated by IgG1 and IgG3, ADCP may be mediated by IgG1, IgG2, IgG3 and IgG4, and CDC may be mediated by IgG1 and IgG3.

In the methods described herein, and in some embodiments of each and every one of the numbered embodiments listed below, the anti-CD38 antibody is of IgG1, IgG2, IgG3 or IgG4 isotype.

In the methods described herein, and in some embodiments of each and every one of the numbered embodiments listed below, the anti-CD38 antibody is of IgG1 or IgG3 isotype.

In the methods described herein, and in some embodiments of each and every one of the numbered embodiments listed below, the anti-CD38 antibody induces in vitro killing of CD38-expressing cells by ADCC.

In the methods described herein, and in some embodiments of each and every one of the numbered embodiments listed below, the anti-CD38 antibody induces in vitro killing of CD38-expressing cells by CDC.

In the methods described herein, and in some embodiments of each and every one of the numbered embodiments listed below, the anti-CD38 antibody induces killing of CD38-expressing cells by ADCC and CDC in vitro.

"Antibody-dependent cellular cytotoxicity," or "antibody-dependent cell-mediated cytotoxicity" or "ADCC" is a mechanism for inducing cell death that depends upon the interaction of antibody-coated target cells with effector cells possessing lytic activity, such as natural killer cells, monocytes, macrophages and neutrophils via Fc gamma receptors (FcγR) expressed on effector cells. For example, NK cells express FcγRIIIa, whereas monocytes express FcγRI, FcγRII and FcγRIIIa. Death of the antibody-coated target cell, such as CD38-expressing cells, occurs as a result of effector cell activity through the secretion of membrane pore-forming proteins and proteases. To assess ADCC activity of an anti-CD38 antibody in vitro, the antibody may be added to CD38-expressing cells in combination with immune effector cells, which may be activated by the antigen antibody complexes resulting in cytolysis of the target cell. Cytolysis is generally detected by the release of label (e.g., radioactive substrates, fluorescent dyes or natural intracellular proteins) from the lysed cells. For example, primary BM-MNC cells isolated from a patient with a B-cell malignancy such as MM may be used for the assay. In an exemplary assay, BM-MNCs may be treated with an anti-CD38 antibody for 1 hour at a concentration of 0.3-10 µg/ml, and the survival of primary CD138$^+$ MM cells may be determined by flow cytometry using techniques described in van der Veer et al., Haematologica 96:284-290, 2001 or in van der Veer et al., Blood Cancer J 1(10):e41, 2011. The percentage of MM cell lysis may be determined relative to an isotype control as described herein. Anti-CD38 antibodies used in the methods of the invention may induce ADCC by about 20%, 25%, 30%, 35%, 40%, 45%, 50%, 55%, 60%, 65%, 70%, 75%, 80%, 85%, 90%, 95% or 100% of control.

"Complement-dependent cytotoxicity", or "CDC", refers to a mechanism for inducing cell death in which an Fc effector domain of a target-bound antibody binds and activates complement component C1q which in turn activates the complement cascade leading to target cell death. Activation of complement may also result in deposition of complement components on the target cell surface that facilitate ADCC by binding complement receptors (e.g., CR3) on leukocytes. In an exemplary assay, primary BM-MNC cells isolated from a patient with a B-cell malignancy may be treated with an anti-CD38 antibody and complement derived from 10% pooled human serum for 1 hour at a concentration of 0.3-10 µg/ml, and the survival of primary CD138+ MM cells may be determined by flow cytometry using techniques described in van der Veer et al., Haematologica 96:284-290, 2011; van der Veer et al., Blood Cancer J 1(10):e41, 2011. The percentage of MM cell lysis may be determined relative to an isotype control as described herein. Anti-CD38 antibodies used in the methods of the invention may induce CDC by about 20%, 25%, 30%, 35%, 40%, 45%, 50%, 55%, 60%, 65%, 70%, 75%, 80%, 85%, 90%, 95% or 100%

The ability of monoclonal antibodies to induce ADCC may be enhanced by engineering their oligosaccharide component. Human IgG1 or IgG3 are N-glycosylated at Asn297 with the majority of the glycans in the well-known biantennary G0, G0F, G1, G1F, G2 or G2F forms. Antibodies produced by non-engineered CHO cells typically have a glycan fucose content of about at least 85%. The removal of the core fucose from the biantennary complex-type oligosaccharides attached to the Fc regions enhances the ADCC of antibodies via improved FcγRIIIa binding without altering antigen binding or CDC activity. Such antibodies may be achieved using different methods reported to lead to the expression of relatively high defucosylated antibodies bearing the biantennary complex-type of Fc oligosaccharides such as control of culture osmolality (Konno et al., Cytotechnology 64:249-65, 2012), application of a variant CHO line Lec13 as the host cell line (Shields et al., J Biol Chem 277:26733-40, 2002), application of a variant CHO line EB66 as the host cell line (Olivier et al., MAbs; 2(4), 2010; Epub ahead of print; PMID:20562582), application of a rat hybridoma cell line YB2/0 as the host cell line (Shinkawa et al., J Biol Chem 278:3466-3473, 2003), introduction of small interfering RNA specifically against the α 1,6-fucosyltrasferase (FUT8) gene (Mori et al., Biotechnol Bioeng 88:901-908, 2004), or co-expression of β-1,4-N-acetylglucosaminyltransferase III and Golgi α-mannosidase II or a potent alpha-mannosidase I inhibitor, kifunensine (Ferrara et al., J Biol Chem 281:5032-5036, 2006, Ferrara et al., Biotechnol Bioeng 93:851-861, 2006; Xhou et al., Biotechnol Bioeng 99:652-65, 2008). ADCC elicited by anti-CD38 antibodies used in the methods of the invention, and in some embodiments of each and every one of the numbered embodiments listed below, may also be enhanced by certain substitutions in the antibody Fc. Exemplary substitutions are, for example, substitutions at amino acid positions 256, 290, 298, 312, 356, 330, 333, 334, 360, 378 or 430 (residue numbering according to the EU index) as described in U.S. Pat. No. 6,737,056. CDC elicited by anti-CD38 antibodies used in the methods of the invention, and in some embodiments of each and every one of the numbered embodiments listed below, may also be enhanced by certain substitutions in the antibody Fc. Exemplary substitutions are, for example, substitutions at amino acid positions 423, 268, 267 and/or 113 (residue numbering according to the EU index) as described in Moore et al., Mabs 2:181-189, 2010.

In some methods described herein, and in some embodiments of each and every one of the numbered embodiments listed below, the anti-CD38 antibodies comprise a substitution in the antibody Fc.

In some methods described herein, and in some embodiments of each and every one of the numbered embodiments listed below, the anti-CD38 antibodies comprise a substitution in the antibody Fc at amino acid positions 256, 290, 298, 312, 356, 330, 333, 334, 360, 378 and/or 430 (residue numbering according to the EU index).

In some methods described herein, and in some embodiments of each and every one of the numbered embodiments listed below, the anti-CD38 antibodies comprise a substitution in the antibody Fc at amino acid position 113, 267, 268 and/or 423 (residue numbering according to the EU index).

Another embodiment of the invention, including in the numbered embodiments listed below, is a method of treating a subject having a CD38-positive hematological malignancy, comprising administering to the subject in need thereof an anti-CD38 antibody in combination with all-trans retinoic acid (ATRA), wherein the anti-CD38 antibody competes for binding to CD38 with an antibody comprising a heavy chain variable region (VH) of SEQ ID NO: 4 and a light chain variable region (VL) of SEQ ID NO: 5 (daratumumab).

Another embodiment of the invention, including in the numbered embodiments listed below, is a method of treating a subject having a CD38-positive hematological malignancy, comprising administering to the subject in need thereof an anti-CD38 antibody in combination with all-trans retinoic acid (ATRA), wherein the anti-CD38 antibody induces killing of CD38-expressing cells in vitro by antibody-dependent cell-mediated cytotoxicity (ADCC) or complement dependent cytotoxicity (CDC), wherein the anti-CD38 antibody competes for binding to CD38 with an antibody comprising a heavy chain variable region (VH) of SEQ ID NO: 4 and a light chain variable region (VL) of SEQ ID NO: 5 (daratumumab).

Antibodies may be evaluated for their competition with daratumumab having the VH of SEQ ID NO: 4 and the VL of SEQ ID NO: 5 for binding to CD38 using well known in vitro methods. In an exemplary method, CHO cells recombinantly expressing CD38 may be incubated with unlabeled daratumumab for 15 min at 4° C., followed by incubation with an excess of fluorescently labeled test antibody for 45 min at 4° C. After washing in PBS/BSA, fluorescence may be measured by flow cytometry using standard methods. In another exemplary method, extracellular portion of human CD38 may be coated on the surface of an ELISA plate. Excess of unlabeled daratumumab may be added for about 15 minutes and subsequently biotinylated test antibodies may be added. After washes in PBS/Tween, binding of the test biotinylated antibodies may be detected using horseradish peroxidase (HRP)-conjugated streptavidine and the signal detected using standard methods. It is readily apparent that in the competition assays, daratumumab may be labelled and the test antibody unlabeled. The test antibody competes with daratumumab when daratumumab inhibits binding of the test antibody, or the test antibody inhibits binding of daratumumab by 80%, 85%, 90%, 95% or 100%. The epitope of the test antibody can further be defined, for example, by peptide mapping or hydrogen/deuterium protection assays using known methods.

Another embodiment of the invention disclosed herein, including in the numbered embodiments listed below, is a method of treating a subject having a CD38-positive hematological malignancy, comprising administering to the subject in need thereof an anti-CD38 antibody that binds to the region SKRNIQFSCKNIYR (SEQ ID NO: 2) and the region EKVQTLEAWVIHGG (SEQ ID NO: 3) of human CD38 (SEQ ID NO: 1) in combination with all-trans retinoic acid (ATRA).

Another embodiment of the invention disclosed herein, including in the numbered embodiments listed below, is a method of treating a subject having a CD38-positive hematological malignancy, comprising administering to the subject in need thereof an anti-CD38 antibody that binds to the region SKRNIQFSCKNIYR (SEQ ID NO: 2) and the region EKVQTLEAWVIHGG (SEQ ID NO: 3) of human CD38 (SEQ ID NO: 1) in combination with all-trans retinoic acid (ATRA), wherein the anti-CD38 antibody induces killing of CD38-expressing cells in vitro by antibody-dependent cell-mediated cytotoxicity (ADCC) or complement dependent cytotoxicity (CDC). The antibody "binds to the region SKRNIQFSCKNIYR (SEQ ID NO: 2) and the region EKVQTLEAWVIHGG (SEQ ID NO: 3)" when the antibody binds at least one amino acid residue within each region. The antibody may bind for example 1, 2, 3, 4, 5, 6, 7, 8, 9, 10, 11, 12, 13 or 14 amino acid residues within each region of SEQ ID NO:2 and SEQ ID NO: 3. The antibody may also optionally bind one or more residues outside of the regions of SEQ ID NO: 2 and SEQ ID NO: 3. Binding may be assessed by known methods such as mutagenesis studies or by resolving the crystal structure of CD38 in complex with the antibody. In some embodiments disclosed herein, including in the numbered embodiments listed below, the antibody epitope comprises at least one amino acid in the region SKRNIQFSCKNIYR (SEQ ID NO: 2) and at least one amino acid in the region EKVQTLEAWVIHGG (SEQ ID NO: 3) of human CD38 (SEQ ID NO: 1). In some embodiments disclosed herein, including in the numbered embodiments listed below, the antibody epitope comprises at least two amino acids in the region SKRNIQFSCKNIYR (SEQ ID NO: 2) and at least two amino acids in the region EKVQTLEAWVIHGG (SEQ ID NO: 3) of human CD38 (SEQ ID NO: 1). In some embodiments disclosed herein, including in the numbered embodiments listed below, the antibody epitope comprises at least three amino acids in the region SKRNIQFSCKNIYR (SEQ ID NO: 2) and at least three amino acids in the region EKVQTLEAWVIHGG (SEQ ID NO: 3) of human CD38 (SEQ ID NO: 1). In some embodiments disclosed herein, including in the numbered embodiments listed below, the anti-CD38 antibody binds to an epitope comprising at least KRN in the region SKRNIQFSCKNIYR (SEQ ID NO: 2) and comprising at least VQLT (SEQ ID NO: 22) in the region EKVQTLEAWVIHGG (SEQ ID NO: 3) of human CD38 (SEQ ID NO: 1).

In some embodiments of the invention described herein, and in some embodiments of each and every one of the numbered embodiments listed below, the anti-CD38 antibody binds to an epitope comprising at least KRN in the region SKRNIQFSCKNIYR (SEQ ID NO: 2) and comprising at least VQLT (SEQ ID NO: 22) in the region EKVQTLEAWVIHGG (SEQ ID NO: 3) of human CD38 (SEQ ID NO: 1).

An exemplary antibody that binds to the region SKRNIQFSCKNIYR (SEQ ID NO: 2) and the region EKVQTLEAWVIHGG (SEQ ID NO: 3) of human CD38 (SEQ ID NO: 1) or minimally to residues KRN and VQLT (SEQ ID NO: 22) as shown above is daratumumab having certain VH, VL and CDR sequences as described above. Antibodies that bind to the region SKRNIQFSCKNIYR (SEQ ID NO: 2) and the region EKVQTLEAWVIHGG (SEQ ID NO: 3) of human CD38 (SEQ ID NO: 1) may be generated, for example, by immunizing mice with peptides having the amino acid sequences shown in SEQ ID NOs: 2 and 3 using standard methods and as described herein. Antibodies may be further evaluated, for example, by assaying competition between daratumumab and a test antibody for binding to CD38 as described above.

In the methods described herein, and in some embodiments of each and every one of the numbered embodiments listed below, the anti-CD38 antibody may bind human CD38 with a range of affinities ($K_D$). In one embodiment according to the invention, and in some embodiments of each and every one of the numbered embodiments listed below, the anti-CD38 antibody binds to CD38 with high affinity, for example, with a $K_D$ equal to or less than about $10^{-7}$ M, such as about 1, 2, 3, 4, 5, 6, 7, 8, or $9 \times 10^{-8}$ M, $1 \times 10^{-9}$ M, about $1 \times 10^{-10}$ M, about $1 \times 10^{-11}$ M, about $1 \times 10^{-12}$ M, about $1 \times 10^{-13}$ M, about $1 \times 10^{-14}$ M, about $1 \times 10^{-15}$ M or any range or value therein, as determined by surface plasmon resonance or the Kinexa method, as practiced by those of skill in the art. One exemplary affinity is equal to or less than $1 \times 10^{-8}$ M. Another exemplary affinity is equal to or less than $1 \times 10^{-9}$ M.

In some methods described herein, and in some embodiments of each and every one of the numbered embodiments listed below, the anti-CD38 antibody has a biantennary glycan structure with fucose content of about between 0% to about 15%, for example 15%, 14%, 13%, 12%, 11% 10%, 9%, 8%, 7%, 6%, 5%, 4%, 3%, 2%, 1% or 0%.

In some methods described herein, and in some embodiments of each and every one of the numbered embodiments listed below, the anti-CD38 antibody has a biantennary glycan structure with fucose content of about 50%, 40%, 45%, 40%, 35%, 30%, 25%, 20%, 15%, 14%, 13%, 12%, 11% 10%, 9%, 8%, 7%, 6%, 5%, 4%, 3%, 2%, 1% or 0%

Substitutions in the Fc and reduced fucose content may enhance the ADCC activity of the anti-CD38 antibody.

"Fucose content" refers to the amount of the fucose monosaccharide within the sugar chain at Asn297. The relative amount of fucose is the percentage of fucose-containing structures related to all glycostructures. Glycostructures may be characterized and quantified by multiple methods, for example 1) using MALDI-TOF of N-glycosidase F treated sample (e.g. complex, hybrid and oligo- and high-mannose structures) as described in Int. Pat. Publ. No. WO2008/077546; 2) by enzymatic release of the Asn297 glycans with subsequent derivatization and detection/quantitation by HPLC (UPLC) with fluorescence detection and/or HPLC-MS (UPLC-MS); 3) intact protein analysis of the native or reduced mAb, with or without treatment of the Asn297 glycans with Endo S or other enzyme that cleaves between the first and the second GlcNAc monosaccharides, leaving the fucose attached to the first GlcNAc; 4) digestion of the mAb to constituent peptides by enzymatic digestion (e.g., trypsin or endopeptidase Lys-C), and subsequent separation, detection and quantitation by HPLC-MS (UPLC-MS); or 5) separation of the mAb oligosaccharides from the mAb protein by specific enzymatic deglycosylation with PNGase F at Asn 297. The oligosaccharides released may be labeled with a fluorophore, separated and identified by various complementary techniques which allow fine characterization of the glycan structures by matrix-assisted laser desorption ionization (MALDI) mass spectrometry by comparison of the experimental masses with the theoretical masses, determination of the degree of sialylation by ion exchange HPLC (GlycoSep C), separation and quantification of the oligosacharride forms according to hydrophilicity criteria by normal-phase HPLC (GlycoSep N), and separation and quantification of the oligosaccharides by high performance capillary electrophoresis-laser induced fluorescence (HPCE-LIF).

"Low fucose" or "low fucose content" as used in the application refers to antibodies with fucose content of about 0%-15%.

"Normal fucose" or "normal fucose content" as used herein refers to antibodies with fucose content of about over 50%, typically about over 60%, 70%, 80% or over 85%.

In some methods of the invention described herein, and in some embodiments of each and every one of the numbered embodiments listed below, the anti-CD38 antibody comprises the heavy chain complementarity determining regions (HCDR) 1 (HCDR1), 2 (HCDR2) and 3 (HCDR3) sequences of SEQ ID NOs: 6, 7 and 8, respectively.

In some methods of the invention described herein, and in some embodiments of each and every one of the numbered embodiments listed below, the anti-CD38 antibody comprises the light chain complementarity determining regions (LCDR) 1 (LCDR1), 2 (LCDR2) and 3 (LCDR3) sequences of SEQ ID NOs: 9, 10 and 11, respectively.

In some methods of the invention described herein, and in some embodiments of each and every one of the numbered embodiments listed below, the anti-CD38 antibody comprises the heavy chain complementarity determining regions (HCDR) 1 (HCDR1), 2 (HCDR2) and 3 (HCDR3) sequences of SEQ ID NOs: 6, 7 and 8, respectively and the light chain complementarity determining regions (LCDR) 1 (LCDR1), 2 (LCDR2) and 3 (LCDR3) sequences of SEQ ID NOs: 9, 10 and 11, respectively.

In some methods of the invention described herein, and in some embodiments of each and every one of the numbered embodiments listed below, the anti-CD38 antibody comprises the heavy chain variable region (VH) of SEQ ID NO: 4 and the light chain variable region (VL) of SEQ ID NO: 5.

In some methods of the invention described herein, and in some embodiments of each and every one of the numbered embodiments listed below, the anti-CD38 antibody comprises the heavy chain of SEQ ID NO: 12 and the light chain of SEQ ID NO: 13.

In some methods of the invention described herein, and in some embodiments of each and every one of the numbered embodiments listed below, the anti-CD38 antibody comprises the heavy chain variable region (VH) of SEQ ID NO: 14 and the light chain variable region (VL) of SEQ ID NO: 15.

In some methods of the invention described herein, and in some embodiments of each and every one of the numbered embodiments listed below, the anti-CD38 antibody comprises the heavy chain variable region (VH) of SEQ ID NO: 16 and the light chain variable region (VL) of SEQ ID NO: 17.

In some methods of the invention described herein, and in some embodiments of each and every one of the numbered embodiments listed below, the anti-CD38 antibody comprises the heavy chain variable region (VH) of SEQ ID NO: 18 and the light chain variable region (VL) of SEQ ID NO: 19.

In some methods of the invention described herein, and in some embodiments of each and every one of the numbered embodiments listed below, the anti-CD38 antibody comprises the heavy chain variable region (VH) of SEQ ID NO: 20 and the light chain variable region (VL) of SEQ ID NO: 21.

In some methods of the invention described herein, and in some embodiments of each and every one of the numbered embodiments listed below, the anti-CD38 antibody comprises a heavy chain comprising an amino acid sequence that is 95%, 96%, 97%, 98% or 99% identical to that of SEQ ID NO: 12 and a light chain comprising an amino acid sequence that is 95%, 96%, 97%, 98% or 99% identical to that of SEQ ID NO: 13.

Antibodies that are substantially identical to the antibody comprising the heavy chain of SEQ ID NO: 12 and the light chain of SEQ ID NO: 13 may be used in the methods of the invention, and in some embodiments of each and every one of the numbered embodiments listed below. The term "substantially identical" as used herein means that the two antibody heavy chain or light chain amino acid sequences being compared are identical or have "insubstantial differences." Insubstantial differences are substitutions of 1, 2, 3, 4, 5, 6, 7, 8, 9, 10, 11, 12, 13, 14, or 15 amino acids in an antibody heavy chain or light chain that do not adversely affect antibody properties. Percent identity can be determined for example by pairwise alignment using the default settings of the AlignX module of Vector NTI v.9.0.0 (Invitrogen, Carlsbad, Calif.). The protein sequences of the present invention can be used as a query sequence to perform a search against public or patent databases to, for example, identify related sequences. Exemplary programs used to perform such searches are the XBLAST or BLASTP programs (http_//www_ncbi_nlm/nih_gov), or the GenomeQuest™ (GenomeQuest, Westborough, Mass.) suite using the default settings. Exemplary substitutions that can be made to the anti-CD38 antibodies used in the methods of the invention are for example conservative substitutions with an amino acid having similar charge, hydrophobic, or stereochemical characteristics. Conservative substitutions may also be made to improve antibody properties, for example stability or affinity, or to improve antibody effector functions. 1, 2, 3, 4, 5, 6, 7, 8, 9, 10, 11, 12, 13, 14, or 15 amino acid substitutions may be made for example to the heavy or the light chain of the anti-CD38 antibody. Furthermore, any native residue in the heavy or light chain may also be substituted with alanine, as has been previously described for alanine scanning mutagenesis (MacLennan et al., Acta Physiol Scand Suppl 643:55-67, 1998; Sasaki et al., Adv Biophys 35:1-24, 1998). Desired amino acid substitutions may be determined by those skilled in the art at the time such substitutions are desired Amino acid substitutions may be done for example by PCR mutagenesis (U.S. Pat. No. 4,683,195). Libraries of variants may be generated using well known methods, for example using random (NNK) or non-random codons, for example DVK codons, which encode 11 amino acids (Ala, Cys, Asp, Glu, Gly, Lys, Asn, Arg, Ser, Tyr, Trp) and screening the libraries for variants with desired properties. The generated variants may be tested for their binding to CD38, their ability to induce ADCC, ADCP or apoptosis in vitro using methods described herein.

In some embodiments, and in some embodiments of each and every one of the numbered embodiments listed below, the anti-CD38 antibody is a bispecific antibody. The VL and/or the VH regions of the existing anti-CD38 antibodies or the VL and VH regions identified de novo as described above may be engineered into bispecific full length antibodies. Such bispecific antibodies may be made by modulating the CH3 interactions between the two monospecific antibody heavy chains to form bispecific antibodies using technologies such as those described in U.S. Pat. No. 7,695,936; Int. Pat. Publ. No. WO04/111233; U.S. Pat. Publ. No. US2010/0015133; U.S. Pat. Publ. No. US2007/0287170; Int. Pat. Publ. No. WO2008/119353; U.S. Pat. Publ. No. US2009/0182127; U.S. Pat. Publ. No. US2010/0286374; U.S. Pat. Publ. No. US2011/0123532; Int. Pat. Publ. No. WO2011/131746; Int. Pat. Publ. No. WO2011/143545; or U.S. Pat. Publ. No. US2012/0149876. Additional bispecific structures into which the VL and/or the VH regions of the antibodies of the invention can be incorporated are for example Dual Variable Domain Immunoglobulins (Int. Pat. Publ. No. WO2009/134776), or structures that include various dimerization domains to connect the two antibody arms with different specificity, such as leucine zipper or collagen dimerization domains (Int. Pat. Publ. No. WO2012/022811, U.S. Pat. No. 5,932,448; U.S. Pat. No. 6,833,441).

Another embodiment of the invention is a method of treating a subject having a CD38-positive hematological malignancy, comprising administering to the subject in need thereof an anti-CD38 antibody in combination with all-trans retinoic acid (ATRA), wherein the CD38-positive hematological malignancy is multiple myeloma (MM), acute lymphoblastic leukemia (ALL), non-Hodgkin's lymphoma, diffuse large B-cell lymphoma (DLBCL), Burkitt's lymphoma (BL), follicular lymphoma (FL) or mantle-cell lymphoma (MCL).

Another embodiment of the invention is a method of treating a subject having a CD38-positive hematological malignancy, comprising administering to the subject in need thereof an anti-CD38 antibody in combination with all-trans retinoic acid (ATRA), wherein the anti-CD38 antibody induces killing of CD38-expressing cells in vitro by antibody-dependent cell-mediated cytotoxicity (ADCC) or complement dependent cytotoxicity (CDC), wherein the CD38-positive hematological malignancy is multiple myeloma (MM), acute lymphoblastic leukemia (ALL), non-Hodgkin's lymphoma, diffuse large B-cell lymphoma (DLBCL), Burkitt's lymphoma (BL), follicular lymphoma (FL) or mantle-cell lymphoma (MCL).

Another embodiment of the invention is a method of treating a subject having a CD38-positive hematological malignancy, comprising administering to the subject in need thereof an anti-CD38 antibody in combination with all-trans retinoic acid (ATRA), wherein the CD38-positive hematological malignancy is multiple myeloma (MM).

Another embodiment of the invention is a method of treating a subject having a CD38-positive hematological malignancy, comprising administering to the subject in need thereof an anti-CD38 antibody in combination with all-trans retinoic acid (ATRA), wherein the anti-CD38 antibody induces killing of CD38-expressing cells in vitro by antibody-dependent cell-mediated cytotoxicity (ADCC) or complement dependent cytotoxicity (CDC), wherein the CD38-positive hematological malignancy is multiple myeloma (MM).

The invention also provides for a method of treating a subject having a CD38-positive hematological malignancy, comprising administering to the subject in need thereof an anti-CD38 in combination with all-trans retinoic acid (ATRA), wherein the subject is resistant to or has acquired resistance to treatment with the anti-CD38 antibody.

The invention also provides for a method of treating a subject having a CD38-positive hematological malignancy, comprising administering to the subject in need thereof an anti-CD38 in combination with all-trans retinoic acid (ATRA), wherein the anti-CD38 antibody induces killing of CD38-expressing cells in vitro by antibody-dependent cell-mediated cytotoxicity (ADCC) or complement dependent cytotoxicity (CDC), wherein the subject is resistant to or has acquired resistance to treatment with the anti-CD38 antibody.

The invention also provides for a method of treating a subject having a CD38-positive hematological malignancy, comprising administering to the subject in need thereof an anti-CD38 in combination with all-trans retinoic acid (ATRA), wherein the subject is resistant to or has acquired resistance to treatment with at least one chemotherapeutic agent.

The invention also provides for a method of treating a subject having a CD38-positive hematological malignancy, comprising administering to the subject in need thereof an anti-CD38 in combination with all-trans retinoic acid (ATRA), wherein the anti-CD38 antibody induces killing of CD38-expressing cells in vitro by antibody-dependent cell-mediated cytotoxicity (ADCC) or complement dependent cytotoxicity (CDC), wherein the subject is resistant to or has acquired resistance to treatment with at least one chemotherapeutic agent.

The invention also provides for a method of treating a subject having multiple myeloma, comprising administering to the subject in need thereof an anti-CD38 in combination with all-trans retinoic acid (ATRA), wherein the subject is resistant to or has acquired resistance to treatment with at least one chemotherapeutic agent.

The invention also provides for a method of treating a subject having multiple myeloma, comprising administering to the subject in need thereof an anti-CD38 in combination with all-trans retinoic acid (ATRA), wherein the anti-CD38 antibody induces killing of CD38-expressing cells in vitro by antibody-dependent cell-mediated cytotoxicity (ADCC) or complement dependent cytotoxicity (CDC), wherein the subject is resistant to or has acquired resistance to treatment with at least one chemotherapeutic agent.

In some embodiments of the invention described herein, and in some embodiments of each and every one of the numbered embodiments listed below, the subject is resistant to or has acquired resistance to treatment with at least one chemotherapeutic agent, wherein the at least one chemotherapeutic agent is lenalidomide, bortezomib, melphalan, dexamethasone or thalidomide.

In some embodiments of the invention described herein, and in some embodiments of each and every one of the numbered embodiments listed below, the subject is resistant to or has acquired resistance to treatment with at least one chemotherapeutic agent, wherein the at least one chemotherapeutic agent is lenalidomide, bortezomib, melphalan, dexamethasone, thalidomide, cyclophosphamide, hydroxydaunorubicin (doxorubicin), vincristine or prednisone.

In some embodiments of the invention described herein, and in some embodiments of each and every one of the numbered embodiments listed below, the subject is resistant to or has acquired resistance to treatment with at least one chemotherapeutic agent, wherein the at least one chemotherapeutic agent is lenalidomide and/or bortezomib.

Various qualitative and/or quantitative methods may be used to determine if a subject is resistant, has developed or is susceptible to developing a resistance to treatment with an anti-CD38 antibody or other therapeutic agent. Symptoms that may be associated with resistance include, for example, a decline or plateau of the well-being of the patient, an increase in the size of a tumor, increase in the number of cancer cells, arrested or slowed decline in growth of a tumor or tumor cells, and/or the spread of cancerous cells in the body from one location to other organs, tissues or cells. Re-establishment or worsening of various symptoms associated with tumor may also be an indication that a subject has developed or is susceptible to developing resistance to an anti-CD38 antibody or other therapeutic agent. The symptoms associated with cancer may vary according to the type of cancer. For example, symptoms associated with B-cell malignancies may include swollen lymph nodes in neck, groin or armpits, fever, night sweats, coughing, chest pain, unexplained weight loss, abdominal swelling or pain, or a feeling of fullness. Remission in malignant lymphomas is standardized using the Cheson criteria (Cheson et al., J Clin Oncology 25:579-586, 2007), which guidelines can be used to determine if a subject has developed a resistance to an anti-CD38 antibody or other therapeutic agent.

In some embodiments of the invention described herein, and in some embodiments of each and every one of the numbered embodiments listed below, the subject having a CD38-positive hematological malignancy is homozygous for phenylalanine at position 158 of CD16 (FcγRIIIa-158F/F genotype) or heterozygous for valine and pheynylalanine at position 158 of CD16 (FcγRIIIa-158F/V genotype). CD16 is also known as the Fc gamma receptor IIIa (FcγRIIIa) or the low affinity immunoglobulin gamma Fc region receptor III-A isoform. Valine/phenylalanine (V/F) polymorphism at FcγRIIIa protein residue position 158 has been shown to affect FcγRIIIa affinity to human IgG. Receptor with FcγRIIIa-158F/F or FcγRIIIa-158F/V polymorphisms demonstrates reduced Fc engagement and therefore reduced ADCC when compared to the FcγRIIIa-158V/V. The lack of or low amount of fucose on human N-linked oligosaccharides improves the ability of the antibodies to induce ADCC due to improved binding of the antibodies to human FcγRIIIa (CD16) (Shields et al., J Biol Chem 277:26733-40, 2002). Patients can be analyzed for their FcγRIIIa polymorphism using routine methods.

The invention also provides for the method of treating a subject having a CD38-positive hematological malignancy, comprising administering to the subject in need thereof an anti-CD38 in combination with all-trans retinoic acid (ATRA), wherein the subject is homozygous for phenylalanine at position 158 of CD16 or heterozygous for valine and pheynylalanine at position 158 of CD16.

The invention also provides for the method of treating a subject having a CD38-positive hematological malignancy, comprising administering to the subject in need thereof an anti-CD38 in combination with all-trans retinoic acid (ATRA), wherein the anti-CD38 antibody induces killing of CD38-expressing cells in vitro by antibody-dependent cell-mediated cytotoxicity (ADCC) or complement dependent cytotoxicity (CDC), wherein the subject is homozygous for phenylalanine at position 158 of CD16 or heterozygous for valine and pheynylalanine at position 158 of CD16.

Administration/Pharmaceutical Compositions

In the methods of the invention, and in some embodiments of each and every one of the numbered embodiments listed below, the anti-CD38 antibodies may be provided in suitable pharmaceutical compositions comprising the anti-CD38 antibody and a pharmaceutically acceptable carrier. The carrier may be diluent, adjuvant, excipient, or vehicle with which the anti-CD38 antibody is administered. Such vehicles may be liquids, such as water and oils, including those of petroleum, animal, vegetable or synthetic origin, such as peanut oil, soybean oil, mineral oil, sesame oil and the like. For example, 0.4% saline and 0.3% glycine may be used. These solutions are sterile and generally free of particulate matter. They may be sterilized by conventional, well-known sterilization techniques (e.g., filtration). The compositions may contain pharmaceutically acceptable auxiliary substances as required to approximate physiological conditions such as pH adjusting and buffering agents, stabilizing, thickening, lubricating and coloring agents, etc. The concentration of the molecules or antibodies of the invention in such pharmaceutical formulation may vary widely, i.e., from less than about 0.5%, usually to at least about 1% to as much as 15 or 20% by weight and will be selected primarily based on required dose, fluid volumes, viscosities, etc., according to the particular mode of administration selected. Suitable vehicles and formulations, inclusive of other human proteins, e.g., human serum albumin, are described, for example, in e.g. Remington: The Science and Practice of Pharmacy, 21$^{st}$ Edition, Troy, D. B. ed., Lipincott Williams and Wilkins, Philadelphia, Pa. 2006, Part 5, Pharmaceutical Manufacturing pp 691-1092, see especially pp. 958-989.

The mode of administration of the anti-CD38 antibody in the methods of the invention may be any suitable route such as parenteral administration, e.g., intradermal, intramuscular, intraperitoneal, intravenous or subcutaneous, pulmonary, transmucosal (oral, intranasal, intravaginal, rectal) or other means appreciated by the skilled artisan, as well known in the art.

The anti-CD38 antibody in the methods of the invention, and in some embodiments of each and every one of the numbered embodiments listed below, may be administered to a patient by any suitable route, for example parentally by intravenous (i.v.) infusion or bolus injection, intramuscularly or subcutaneously or intraperitoneally. i.v. infusion may be given over for, example, 15, 30, 60, 90, 120, 180, or 240 minutes, or from 1, 2, 3, 4, 5, 6, 7, 8, 9, 10, 11 or 12 hours.

The dose given to a patient having a CD38-positive hematological malignancy is sufficient to alleviate or at least partially arrest the disease being treated ("therapeutically effective amount") and may be sometimes 0.005 mg/kg to about 100 mg/kg, e.g. about 0.05 mg/kg to about 30 mg/kg or about 5 mg to about 25 mg/kg, or about 4 mg/kg, about 8 mg/kg, about 16 mg/kg or about 24 mg/kg, or, e.g., about 1, 2, 3, 4, 5, 6, 7, 8, 9 or 10 mg/kg, but may even higher, for example about 15, 16, 17, 18, 19, 20, 21, 22, 23, 24, 25, 30, 40, 50, 60, 70, 80, 90 or 100 mg/kg.

A fixed unit dose may also be given, for example, 50, 100, 200, 500 or 1000 mg, or the dose may be based on the patient's surface area, e.g., 500, 400, 300, 250, 200, or 100 mg/m$^2$. Usually between 1 and 8 doses, (e.g., 1, 2, 3, 4, 5, 6, 7 or 8) may be administered to treat a CD38-positive B-cell malignancy, but 9, 10, 11, 12, 13, 14, 15, 16, 17, 18, 19, 20 or more doses may be given.

The administration of the anti-CD38 antibody in the methods of the invention and in some embodiments of each and every one of the numbered embodiments listed below, may be repeated after one day, two days, three days, four days, five days, six days, one week, two weeks, three weeks, one month, five weeks, six weeks, seven weeks, two months, three months, four months, five months, six months or longer. Repeated courses of treatment are also possible, as is chronic administration. The repeated administration may be at the same dose or at a different dose. For example, the anti-CD38 antibody in the methods of the invention may be administered at 8 mg/kg or at 16 mg/kg at weekly interval for 8 weeks, followed by administration at 8 mg/kg or at 16 mg/kg every two weeks for an additional 16 weeks, followed by administration at 8 mg/kg or at 16 mg/kg every four weeks by intravenous infusion.

The anti-CD38 antibodies may be administered in the methods of the invention and in some embodiments of each and every one of the numbered embodiments listed below, by maintenance therapy, such as, e.g., once a week for a period of 6 months or more.

For example, anti-CD38 antibodies in the methods of the invention and in some embodiments of each and every one of the numbered embodiments listed below, may be provided as a daily dosage in an amount of about 0.1-100 mg/kg, such as 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively, at least one of week 1, 2, 3, 4, 5, 6, 7, 8, 9, 10, 11, 12, 13, 14, 15, 16, 17, 18, 19 or 20 after initiation of treatment, or any combination thereof, using single or divided doses of every 24, 12, 8, 6, 4, or 2 hours, or any combination thereof.

Anti-CD38 antibodies in the methods of the invention and in some embodiments of each and every one of the numbered embodiments listed below, may also be administered prophylactically in order to reduce the risk of developing cancer, delay the onset of the occurrence of an event in cancer progression, and/or reduce the risk of recurrence when a cancer is in remission. This may be especially useful in patients wherein it is difficult to locate a tumor that is known to be present due to other biological factors.

The anti-CD38 antibody in the methods of the invention and in some embodiments of each and every one of the numbered embodiments listed below, may be lyophilized for storage and reconstituted in a suitable carrier prior to use. This technique has been shown to be effective with conventional protein preparations and well known lyophilization and reconstitution techniques can be employed.

The anti-CD38 antibody in the methods of the invention and in some embodiments of each and every one of the numbered embodiments listed below may be administered in combination with all-trans retinoic acid (ATRA).

ATRA may be provided as a dosage of 45 mg/m$^2$/day PO or 25 mg/m$^2$/day PO.

The anti-CD38 antibody in the methods of the invention and in some embodiments of each and every one of the numbered embodiments listed below may be administered in combination with all-trans retinoic acid (ATRA) and a third therapeutic agent.

In the methods of the invention, and in some embodiments of each and every one of the numbered embodiments listed below, the third therapeutic agent may be melphalan, mechlorethamine, thioepa, chlorambucil, carmustine (BSNU), lomustine (CCNU), cyclophosphamide, busulfan, dibromomannitol, streptozotocin, dacarbazine (DTIC), procarbazine, mitomycin C, cisplatin and other platinum derivatives, such as carboplatin, thalidomide or a thalidomide analog, lenalidomide or CC4047, a proteasome inhibitor, such as bortezomib or *vinca* alkaloid, such as vincristine or an anthracycline, such as doxorubicin.

While having described the invention in general terms, the embodiments of the invention will be further disclosed in the following examples that should not be construed as limiting the scope of the claims.

Further Embodiments of the Invention

Set out below are certain further embodiments of the invention according to the disclosures elsewhere herein. Features from embodiments of the invention set out above described as relating to the invention disclosed herein also relate to each and every one of these further numbered embodiments.

1. An anti-CD38 antibody for use in treating a subject having a CD38-positive hematological malignancy, in combination with all-trans retinoic acid (ATRA).
2. ATRA for use in treating a subject having a CD38-positive hematological malignancy, in combination with an anti-CD38 antibody.
3. The combination of an anti-CD38 antibody) and ATRA for use in treating a subject having a CD38-positive hematological malignancy.
4. The anti-CD38 antibody for use according to embodiment 1, ATRA for use according to embodiment 2, or the combination for use according to embodiment 3, wherein the anti-CD38 antibody induces killing of the CD38-expressing cells by
   a. antibody-dependent cell-mediated cytotoxicity (ADCC);
   b. complement dependent cytotoxicity (CDC); or
   c. both ADCC and CDC in vitro.
5. The anti-CD38 antibody for use according to embodiment 1, ATRA for use according to embodiment 2, or the combination for use according to embodiment 3, wherein the anti-CD38 antibody induces killing of the CD38-expressing cells by ADCC in vitro.
6. The anti-CD38 antibody for use according to embodiment 1, 4 or 5, ATRA for use according to embodiment 2, 4 or 5, or the combination for use according to embodiment 3-5, wherein the CD38-positive hematological malignancy is multiple myeloma (MM), acute lymphoblastic leukemia (ALL), non-Hodgkin's lymphoma (NHL), diffuse large B-cell lymphoma (DLBCL), Burkitt's lymphoma (BL), follicular lymphoma (FL) or mantle-cell lymphoma (MCL).
7. The anti-CD38 antibody for use according to embodiment 1, 4-6, ATRA for use according to embodiment 2, 4-6, or the combination for use according to embodiment 3-6, wherein the CD38-positive hematological malignancy is MM.
8. The anti-CD38 antibody for use according to embodiment 1, 4-7, ATRA for use according to embodiment 2, 4-7, or the combination for use according to embodiment 3-7, wherein the subject is resistant to or has acquired resistance to treatment with at least one chemotherapeutic agent, and anti-CD38 antibody, or a combination of at least one chemotherapeutic agent and an anti-CD38 antibody.
9. The anti-CD38 antibody for use according to embodiment 1, 4-8, ATRA for use according to embodiment 2, 4-8, or the combination for use according to embodiment 3-8, wherein the at least one chemotherapeutic agent is lenalidomide, bortezomib, melphalan, dexamethasone or thalidomide.
10. The anti-CD38 antibody for use according to embodiment 1, 4-9, ATRA for use according to embodiment 2, 4-9, or the combination for use according to embodiment 3-9, wherein the at least one chemotherapeutic agent is lenalidomide or bortezomib.
11. The anti-CD38 antibody for use according to embodiment 1, 4-10, ATRA for use according to embodiment 2, 4-10, or the combination for use according to embodiment 3-10, wherein
    a. the anti-CD38 antibody is of IgG1, IgG2, IgG3 or IgG4 isotype;
    b. the anti-CD38 antibody competes for binding to CD38 with an antibody comprising a heavy chain variable region (VH) of SEQ ID NO: 4 and a light chain variable region (VL) of SEQ ID NO: 5;
    c. the anti-CD38 antibody binds to the region SKRNIQFSCKNIYR (SEQ ID NO: 2) and the region EKVQTLEAWVIHGG (SEQ ID NO: 3) of human CD38 (SEQ ID NO: 1);
    d. the anti-CD38 antibody comprises the heavy chain complementarity determining regions (HCDR) 1 (HCDR1), 2 (HCDR2) and 3 (HCDR3) sequences of SEQ ID NOs: 6, 7 and 8, respectively;
    e. the anti-CD38 antibody comprises the light chain complementarity determining regions (LCDR) 1 (LCDR1), 2 (LCDR2) and 3 (LCDR3) sequences of SEQ ID NOs: 9, 10 and 11, respectively;

f. the anti-CD38 antibody comprises the heavy chain variable region (VH) of SEQ ID NO: 4 and the light chain variable region (VL) of SEQ ID NO: 5;
g. the anti-CD38 antibody comprises a heavy chain comprising an amino acid sequence that is 95%, 96%, 97%, 98% or 99% identical to that of SEQ ID NO: 12 and a light chain comprising an amino acid sequence that is 95%, 96%, 97%, 98% or 99% identical to that of SEQ ID NO: 13;
h. the anti-CD38 antibody comprises the heavy chain of SEQ ID NO: 12 and the light chain of SEQ ID NO: 13
i. the anti-CD38 antibody comprises th VH of SEQ ID NO: 14 and the VL of SEQ ID NO: 15;
j. the anti-CD38 antibody comprises th VH of SEQ ID NO: 16 and the VL of SEQ ID NO: 17;
k. the anti-CD38 antibody comprises th VH of SEQ ID NO: 18 and the VL of SEQ ID NO: 19; or
l. the anti-CD38 antibody comprises th VH of SEQ ID NO: 20 and the VL of SEQ ID NO: 21.
m.

EXAMPLE 1

General Methods

Antibodies and Reagents

A human mAb against an innocuous antigen (HIV-1 gp120) was used as an isotype control as described previously (van der Veers et al., Haematologica 96:284-290, 2011; van der Veers et al., Blood Cancer J 1:e41, 2011). All-trans retinoic acid (ATRA) was purchased from Sigma-Aldrich and diluted in DMSO.

Bioluminescence Imaging (BLI)-based ADCC Assays Using Luciferase (LUC)-transduced MM Cell Lines LUC-transduced MM cell lines were co-cultured with effector cells (freshly isolated PBMCs from healthy donors) at an effector to target ratio of 1:25 in white opaque 96-well flat bottom plates (Costar) in the presence of daratumumab (0.001, 0.01, 0.1, and 1.0 µg/mL) for four hours. The survival of LUC$^+$-MM cells was then determined by BLI, 10 minutes after addition of the substrate luciferin (125 µg/mL; Promega). Lysis of MM cells was determined using the following formula: % lysis=1−(mean BLI signal in the presence of effector cells and daratumumab/mean BLI signal in the presence of effector cells and control antibody)×100%.

BLI-based CDC Assays Using LUC-transduced MM Cell Lines

Daratumumab (0, 0.03, 0.1, 0.3, 1.0 and 3.0 µg/mL) was added to MM cell lines in medium supplemented with pooled human serum (10%; Sanquin) or heat-inactivated human serum. After a 1-hour incubation at 37° C., cell lysis was determined by BLI, 10 minutes after addition of luciferin (125 µg/ml), and calculated using the following formula: % lysis=1−(mean BLI signal in the presence of native human serum/mean BLI signal in the presence of heat-inactivated serum)×100%.

Flow Cytometry-based Ex Vivo ADCC and CDC Assays in BM-MNC

Freshly isolated BM-MNCs, containing 2-57% malignant plasma cells as determined by flow cytometry, were immediately used in ex vivo experiments. For ADCC experiments, BM-MNCs, containing the malignant plasma cells, as well as the patient's own effector cells, were incubated in RPMI+10% fetal bovine serum with daratumumab (0.01-10 µg/mL) in 96-well flat-bottom plates in fully humidified incubators at 37° C., 5% $CO_2$-air mixture for 48 h. Sample viability at incubation was more than 98%, as assessed by using ToPro-3 (Invitrogen/Molecular Probes). For CDC assays, BM-MNCs were treated with daratumumab (0.3-10 µg/mL) and complement for 1 hour prior to flow cytometric analysis. Pooled human serum (10%) was used as a source of complement. The survival of primary CD138$^+$ MM cells in the BM-MNCs was determined by flow-cytometry as previously described (van der Veers et al., Haematologica 96:284-290, 2011; van der Veers et al., Blood Cancer J 1:e41, 2011). Surviving MM cells were enumerated by single platform flow-cytometric analysis of CD138$^+$ cells (with CD138-PE (Beckman Coulter, Miami, Fla., USA)) in the presence of Flow-Count Fluorospheres (Beckman Coulter) to determine absolute numbers of cells. The percentage of MM cell lysis in the different treated conditions was determined relative to MM survival of wells treated with the control antibody (IgG1-b12 as IgG1 control antibody for daratumumab) using the following formula: % lysis cells=1−(absolute number of surviving CD138$^+$ cells in treated wells/absolute number of surviving CD138$^+$ cells in control wells)×100%.

Immunophenotyping by Flow Cytometry

Expression of several cell surface proteins was determined by flow cytometric analysis using FITC-, PE-, PerCP-, or APC-conjugated monoclonal antibodies. Anti-CD38, anti-CD138, and anti-CD56 were purchased from Beckman Coulter; anti-CD3, anti-CD16, anti-CD55, anti-CD59 from BD Biosciences; and anti-CD46 from Biolegend. Flow cytometry was done using a FACS-Calibur device (Becton Dickinson); the data were analyzed using the CellQuest software.

Statistics

Statistical analyses were performed using Prism software (Graphpad Software Inc, version 5). Comparisons between variables were performed using two-tailed paired Student's t test. Correlations between variables were made using the Spearman's rank correlation coefficient. p-values below 0.05 were considered significant.

EXAMPLE 2

ATRA Increases CD38 Expression on MM Cell Lines and in Primary MM Cells

An increase in CD38 expression levels may enhance the efficacy of daratumumab to kill MM cells via ADCC or CDC. Interaction of ATRA with nuclear retinoic acid receptors results in altered expression of target genes including induction of CD38 expression (Malavasi F. J Leukoc Biol 90:217-219, 2011; Drach et al., Cancer Res 54:1746-1752, 1994). Therefore, effect of ATRA on MM cell lines RPMI8226, UM9, and XG1 was studied. MM cells were incubated with RPMI-1640 medium alone or with ATRA ranging from 0-25 nM for 48 hours (FIG. 1A) or were incubated with 10 nM ATRA for 24, 48, 72 or 96 hours (FIG. 1B) and then harvested to determine CD38 expression by flow cytometry using a FACS-Calibur device (Becton Dickinson) and anti-CD38 antibody (Beckman Coulter). The data were analyzed using the CellQuest software.

Figure 1B:
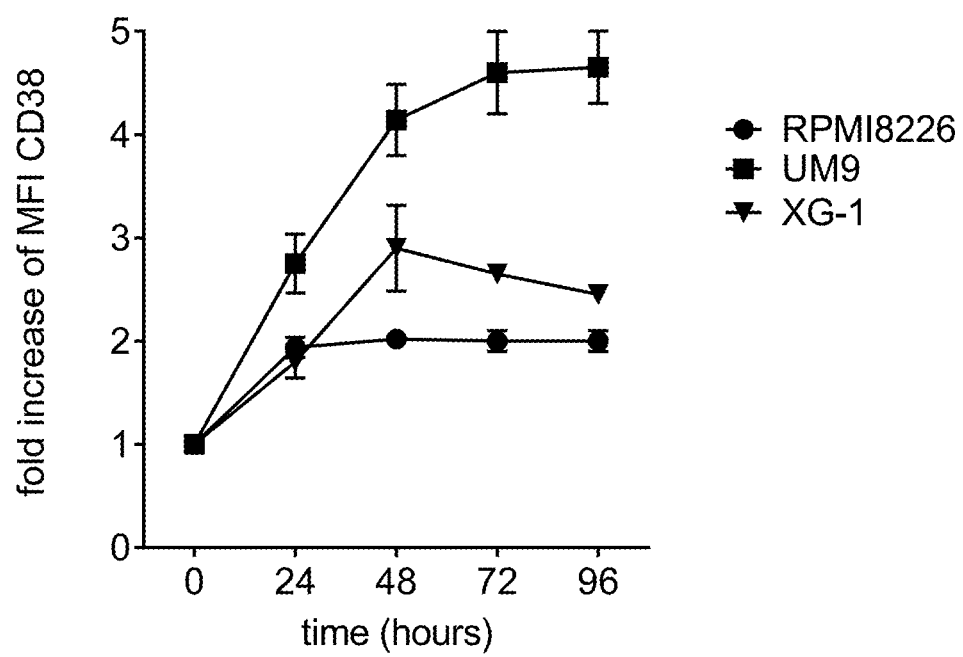
FIG. 1B shows that ATRA enhances CD38 expression on MM cell lines in a time dependent manner. MM cell lines RPMI8226, UM9 and XG1 were incubated with RPMI-1640 medium alone or with 10 nM ATRA for 24, 48, 72 or 96 hours and then harvested to determine CD38 expression by flow cytometry. The graph shows results of one representative experiment. The Y axis shows the fold increase of mean fluorescent intensity (MFI) of CD38 surface expression.

Minimum of 10 nM ATRA was sufficient to induce a 1.9-4.4-fold increase in CD38 expression on the MM cell lines RPMI8226, UM9, and XG1. Higher doses of ATRA did not further enhance CD38 expression (FIG. 1A). Maximum enhancement of CD38 expression occurred at 48 hours (FIG. 1B). Therefore 10 nM ATRA for 48 hours was used in all subsequent experiments.

Ex vivo ATRA exposure (10 nM, 48 hours) of primary MM cells from 26 patients was also studied. In these experiments, BM-MNCs from 26 MM patients were incubated with RPMI-1640 medium alone or with 10 nM ATRA for 48 hours, incubated at 4° C. for 20 min with FITC-conjugated CD38 antibody (Beckman Coulter) and then harvested to determine CD38 expression by flow cytometry. Flow cytometric analyses were performed using a FACS-Calibur device (Becton Dickinson); the data were analyzed using the CellQuest software.

Figure 2:
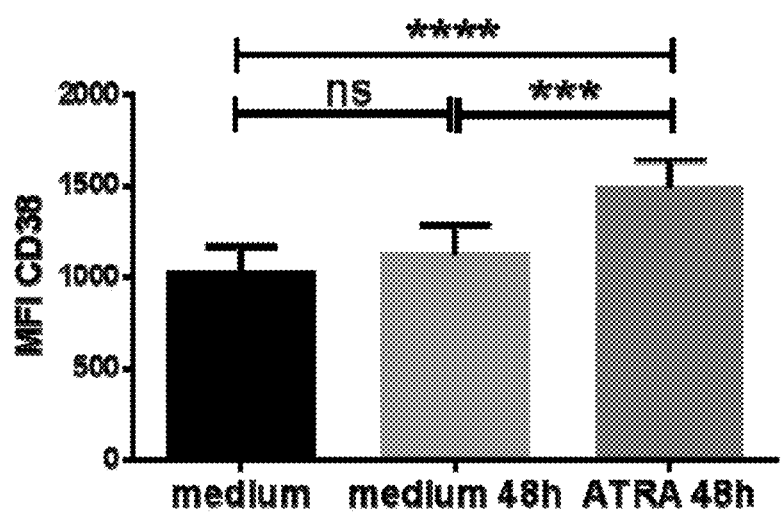
FIG. 2 shows that ATRA enhances CD38 expression on bone marrow mononuclear cells (BM-MNCs) from MM patients ex vivo. BM-MNCs from 26 MM patients were incubated with RPMI-1640 medium alone or with 10 nM ATRA for 48 hours and then harvested to determine CD38 expression by flow cytometry. The Y axis shows the MFI of CD38 surface expression. Medium: medium at 0 hours. ns: not significant.*$p<0.001$; **$p<0.0001$.

ATRA induced CD38 expression (median increase 1.7-fold, range 1.0-26.5-fold) (FIG. 2). There was also a significant upregulation of CD138 expression levels (median increase: 2.0-fold), which is characteristic of MM cell differentiation. In contrast, no significant changes in the expression of other plasma cell antigens, such as HLA A/B/C or CD56 were observed in response to ATRA.

EXAMPLE 3

ATRA-mediated Upregulation of CD38 Enhances Both Daratumumab-mediated ADCC and CDC Against MM Cells Possible effect of ATRA-induced upregulation of CD38 expression on daratumumab-induced ADCC and CDC was tested in MM cell lines XG-1, RPMI8226 and UM9 and in primary MM cells.

For MM cell lines, CDC and ADCC were assessed using bioluminescence imaging (BLI) based ADCC and CDC assays as described above. For primary MM cells, CDC and ADCC were assessed using Flow cytometry-based ex vivo ADCC and CDC assays in BM-MNC as described above. In the assays, cells were pre-treated with 10 nM ATRA or solvent control for 48 hours, followed by incubation with or without daratumumab in the presence of PBMCs as effector cells for assessment of ADCC or in the presence of human serum as complement source for analysis of CDC. Isotype control was added at 10 µg/ml, and 10% heat-inactivated serum was used as control for CDC.

Figure 3A:
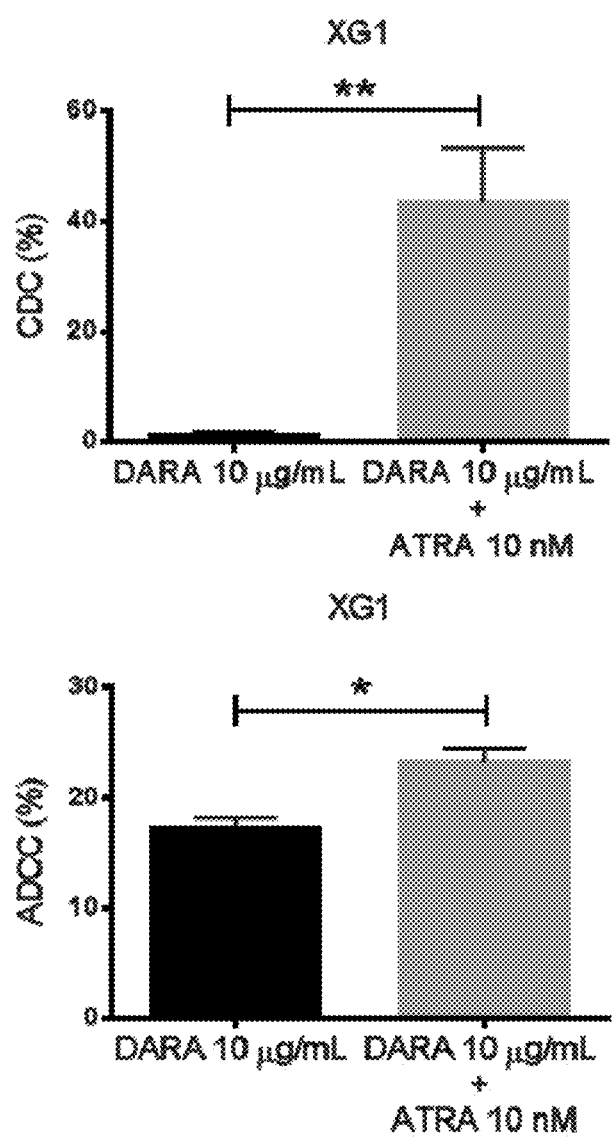
FIG. 3A shows daratumumab-induced complement-dependent cytotoxicity (CDC) (top panel) and antibody-dependent cell mediated cytotoxicity (ADCC) (bottom panel) in MM XG1 cell line pretreated with or without 10 nM ATRA for 48 hours prior to performing CDC or ADCC in the presence of 10 µg/ml daratumumab. The Y axis shows the percent (%) CDC or ADCC. Data show the mean and SEM of at least three experiments. p-values between the indicated groups were calculated using a paired student's t test. Dara: daratumumab; * $p<0.05$; ** $p<0.01$.
Figure 3B:
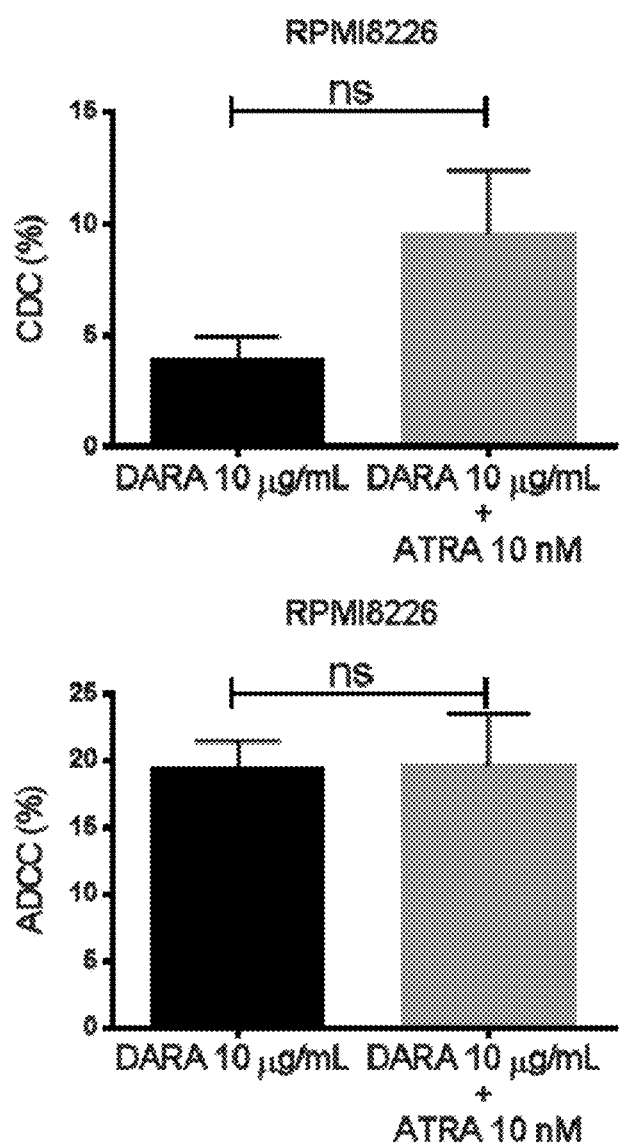
FIG. 3B shows daratumumab-induced CDC (top panel) and ADCC (bottom panel) in MM RPMI8226 cell line pretreated with or without 10 nM ATRA for 48 hours prior to performing CDC or ADCC in the presence of 10 µg/ml daratumumab. The Y axis shows the percent (%) CDC or ADCC. Data show the mean and SEM of at least three experiments. P-values between the indicated groups were calculated using a paired student's t test. Dara: daratumumab; ns: not significant.
Figure 3C:
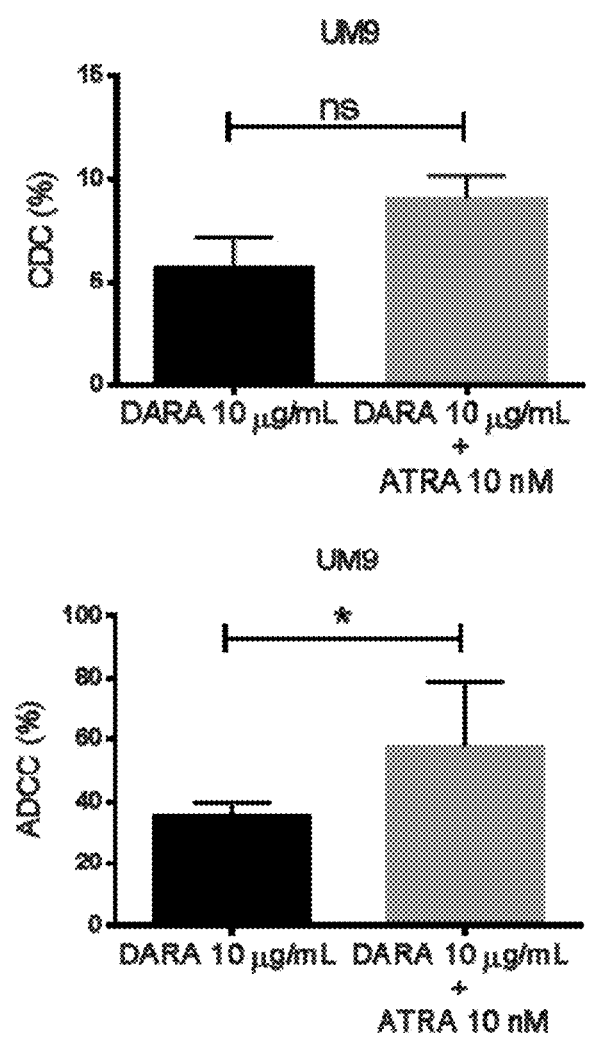
FIG. 3C shows daratumumab-induced CDC (top panel) and ADCC (bottom panel) in MM UM9 cell line pretreated with or without 10 nM ATRA for 48 hours prior to performing CDC or ADCC in the presence of 10 µg/ml daratumumab. The Y axis shows the percent (%) CDC or ADCC. Data show the mean and SEM of at least three experiments. P-values between the indicated groups were calculated using a paired student's t test. Dara: daratumumab; * p<0.05; ns: not significant.

FIG. 3A, FIG. 3B and FIG. 3C show the results of daratumumab-induced CDC and ADCC in the XG1, RPMI8226 and UM9 cell lines, respectively.

10 nM ATRA alone induced no MM cell lysis. Pretreatment of MM cell lines with 10 nM ATRA significantly increased daratumumab-mediated CDC in XG-1 cells (FIG. 3A), and ADCC in XG-1 (FIG. 3A) and UM9 (FIG. 3C) cells, compared with solvent control (FIG. 3A). In RPMI8226 cells there was no significant improvement in daratumumab-mediated ADCC and CDC. These differences in ATRA responsiveness may be partly explained by the fact that ATRA enhanced CD38 expression 2.9-fold in XG-1 and 4.4-fold in UM9, while the upregulation was only 1.9-fold in RPMI8226 cells (FIGS. 1A and 1B).

EXAMPLE 4

ATRA-mediated Upregulation of CD38 Enhances Both Daratumumab-mediated ADCC and CDC Against Primary MM Cells Primary MM cells were evaluated to further explore the effect of ATRA-mediated induction of CD38 expression on daratumumab sensitivity.

Figure 4A:
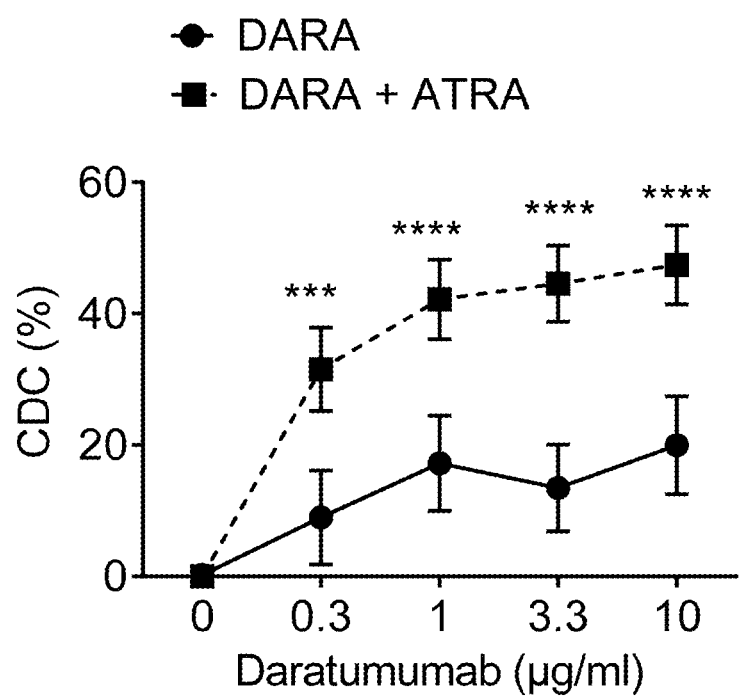
FIG. 4A shows that pretreatment of primary MM cells for 48 hours with 10 nM ATRA potentiates daratumumab-mediated CDC of the primary MM cells. MM cells were pretreated for 48 hours with or without 10 nM ATRA as indicated in the Figure at daratumumab concentrations ranging from 0-10 μg/ml. The graph shows pooled results of 16 patient samples. * p<0.001, ** p<0.0001. DARA: daratumumab.
Figure 4B:
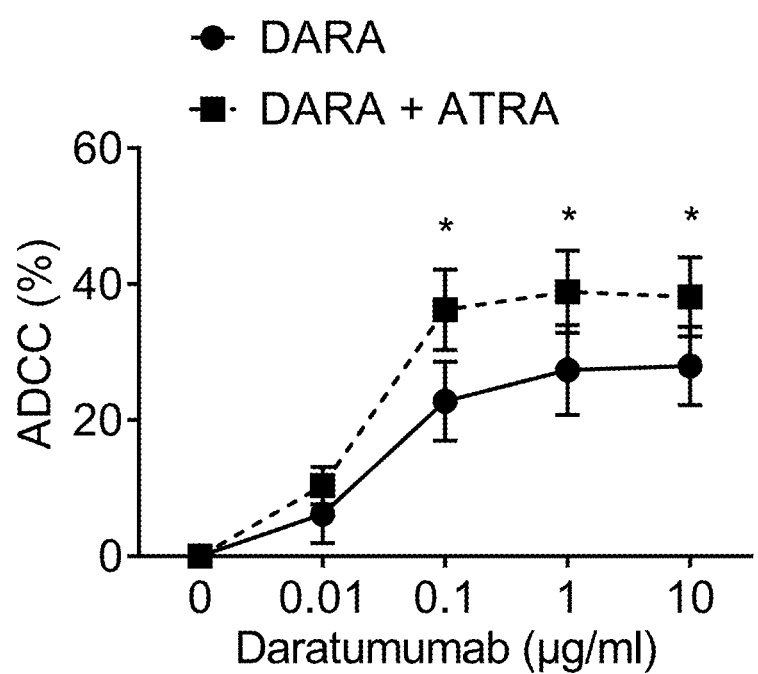
FIG. 4B shows that pretreatment of primary MM cells for 48 hours with 10 nM ATRA potentiates daratumumab-mediated ADCC of the primary MM cells. MM cells were pretreated for 48 hours with or without 10 nM ATRA as indicated in the Figure at daratumumab concentrations ranging from 0-10 μg/ml. The graph shows pooled results of 13 patient samples. * p<0.05. DARA: daratumumab.
Figure 5A:
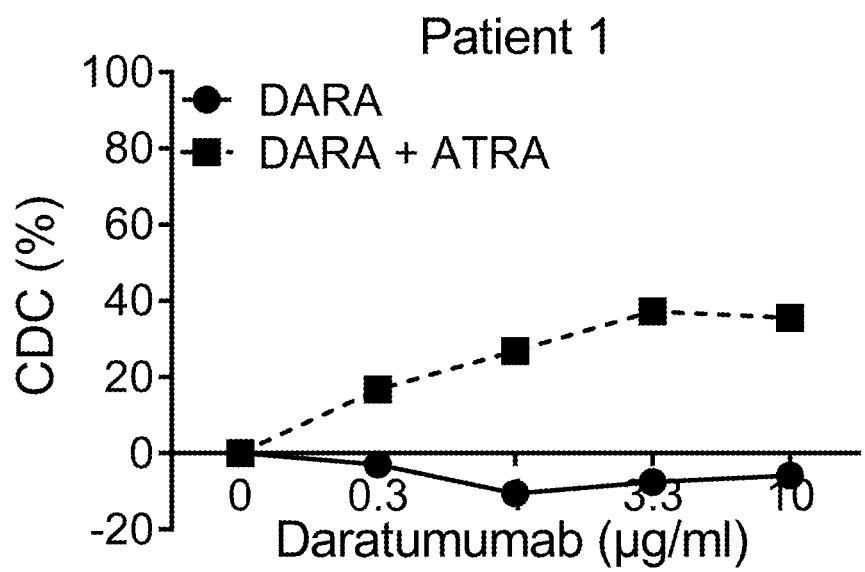
FIG. 5A shows the results of in vitro CDC of primary MM cells isolated from patient 1 and patient 2 pretreated for 48 hours with or without 10 nM ATRA as indicated in the Figure at daratumumab concentrations ranging from 1-10 μg/ml.
Figure 5A:
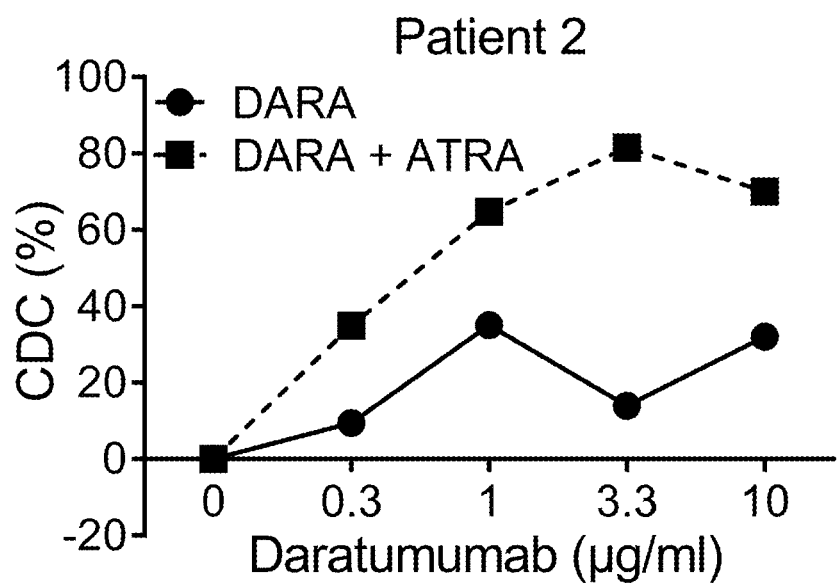
Figure 5B:
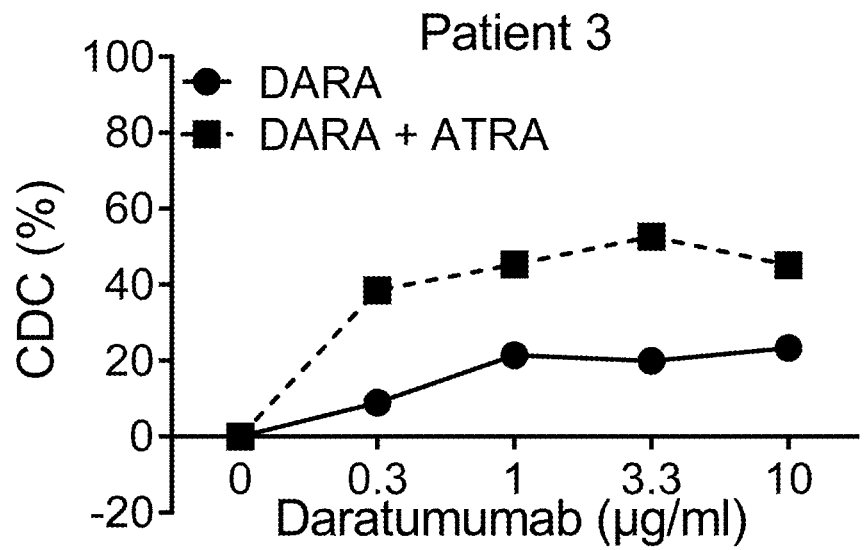
FIG. 5B shows the results of in vitro CDC of primary MM cells isolated from patient 3 and patient 4 pretreated for 48 hours with or without 10 nM ATRA as indicated in the Figure at daratumumab concentrations ranging from 1-10 μg/ml.
Figure 5B:
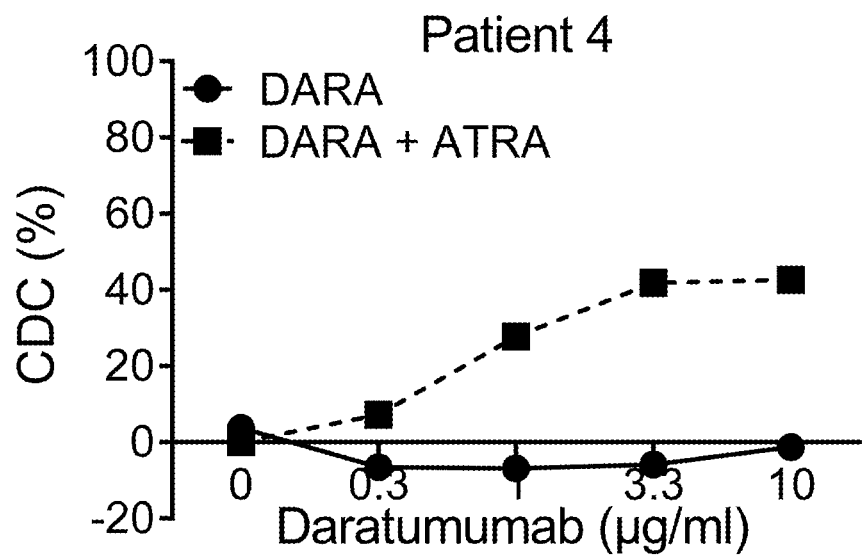
Figure 5C:
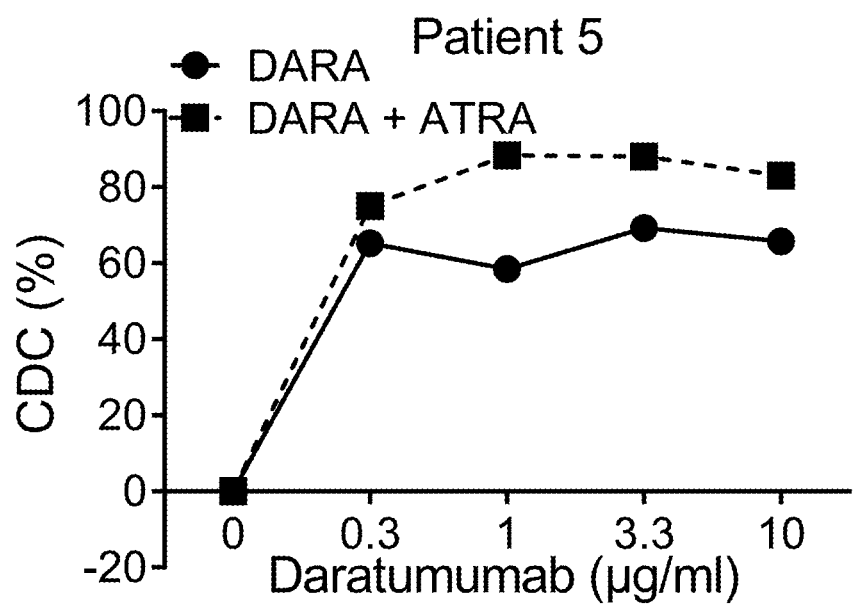
FIG. 5C shows the results of in vitro CDC of primary MM cells isolated from patient 5 and patient 6 pretreated for 48 hours with or without 10 nM ATRA as indicated in the Figure at daratumumab concentrations ranging from 1-10 μg/ml.
Figure 5C:
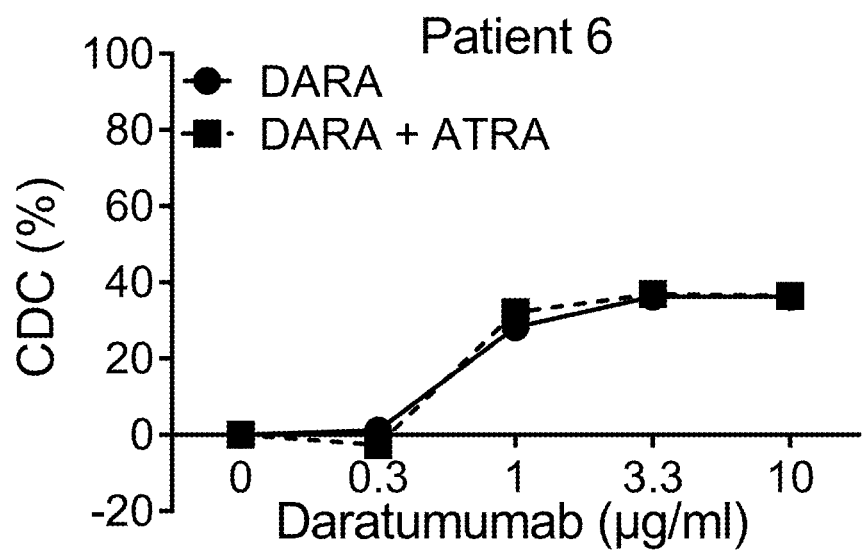
Figure 5D:
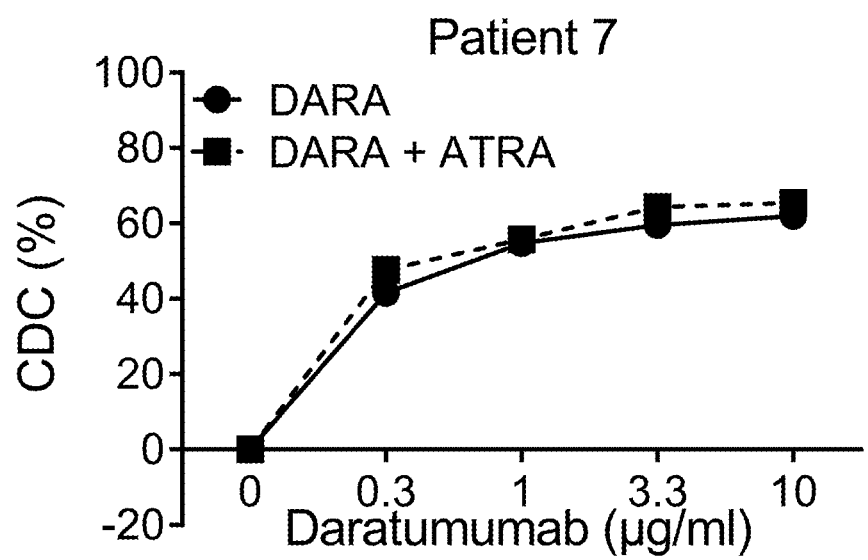
FIG. 5D shows the results of in vitro CDC of primary MM cells isolated from patient 7 and patient 8 pretreated for 48 hours with or without 10 nM ATRA as indicated in the Figure at daratumumab concentrations ranging from 1-10 μg/ml.
Figure 5D:
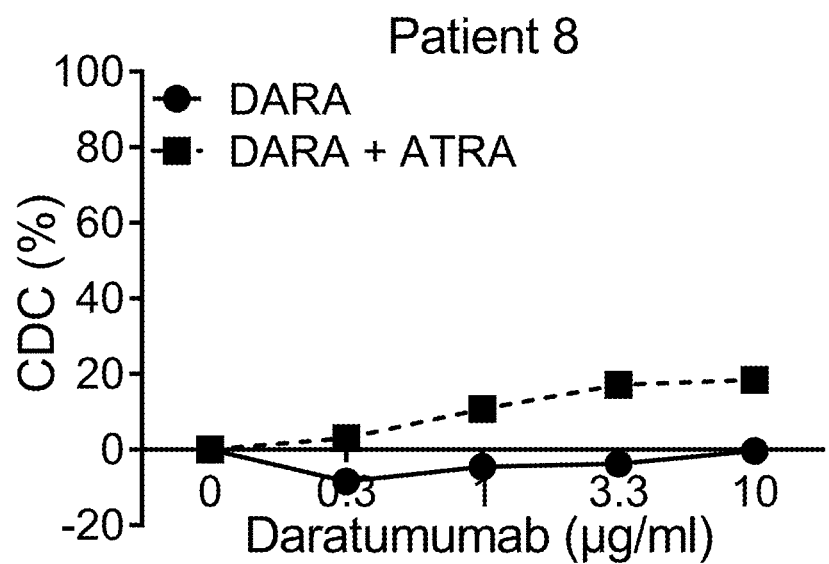
Figure 5E:
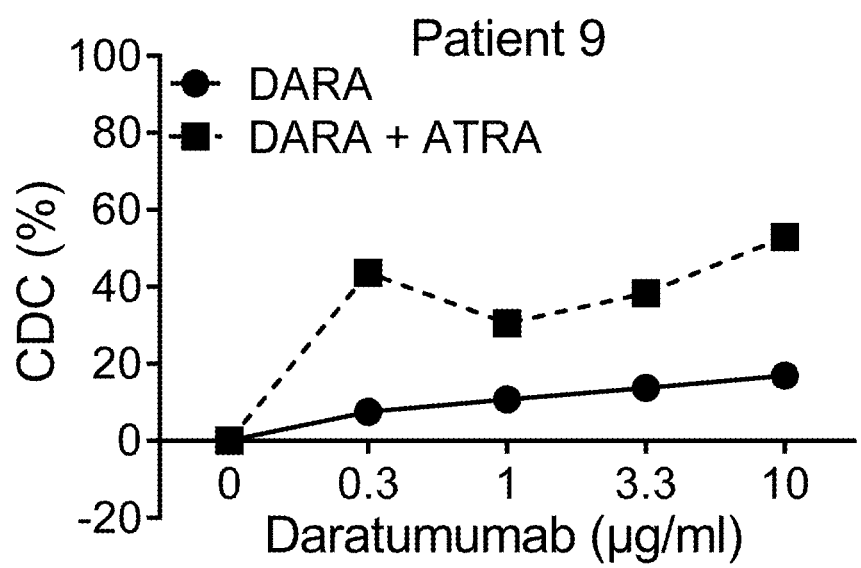
FIG. 5E shows the results of in vitro CDC of primary MM cells isolated from patient 9 and patient 10 pretreated for 48 hours with or without 10 nM ATRA as indicated in the Figure at daratumumab concentrations ranging from 1-10 μg/ml.
Figure 5E:
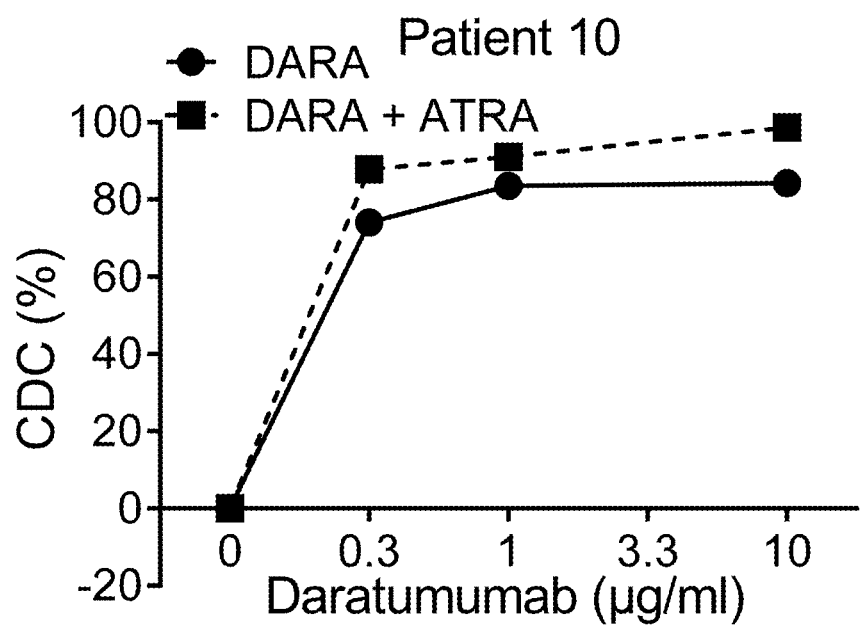
Figure 5F:
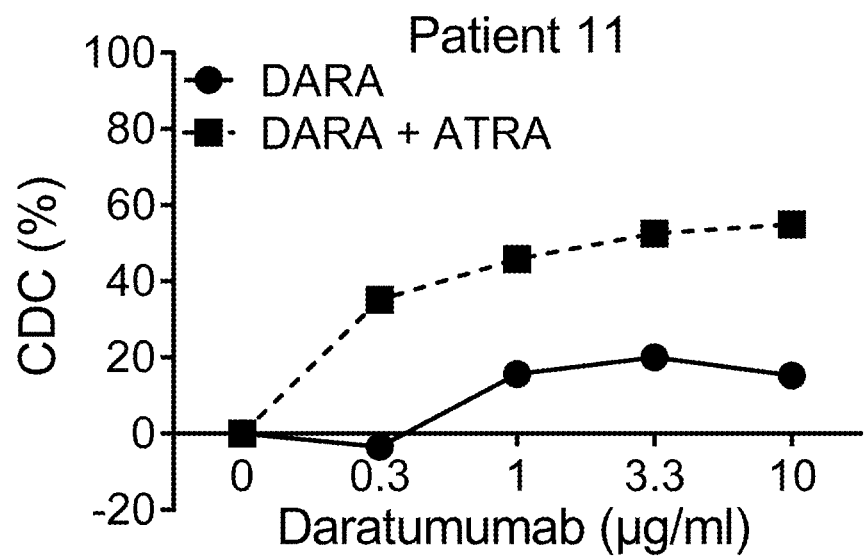
FIG. 5F shows the results of in vitro CDC of primary MM cells isolated from patient 11 and patient 12 pretreated for 48 hours with or without 10 nM ATRA as indicated in the Figure at daratumumab concentrations ranging from 1-10 μg/ml.
Figure 5F:
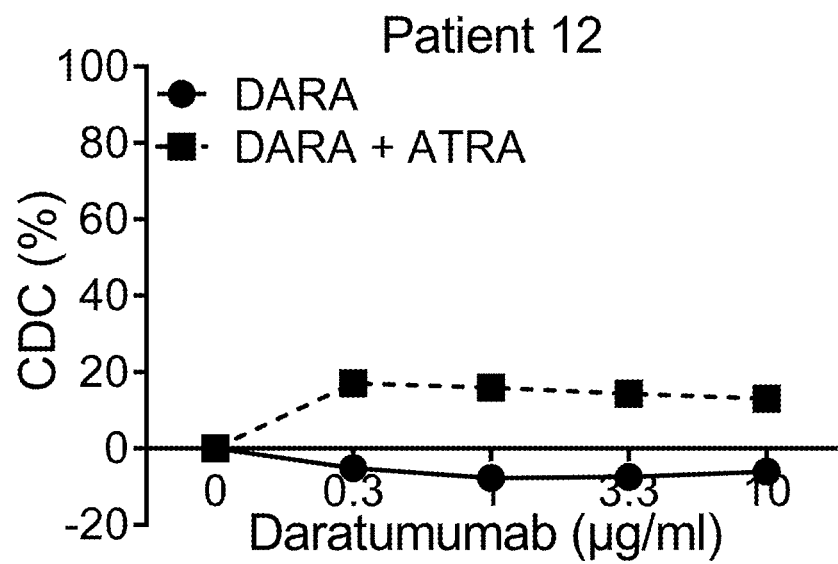
Figure 5G:
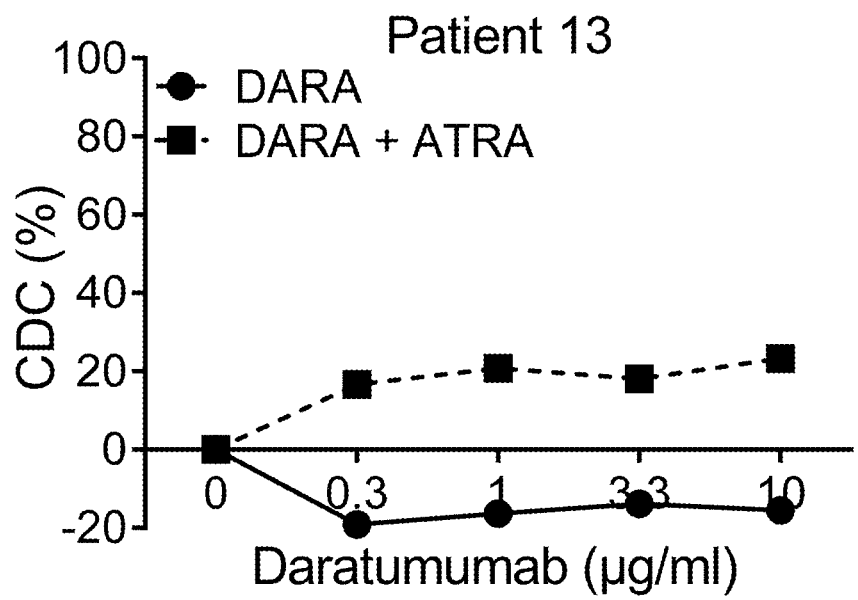
FIG. 5G shows the results of in vitro CDC of primary MM cells isolated from patient 13 and patient 14 pretreated for 48 hours with or without 10 nM ATRA as indicated in the Figure at daratumumab concentrations ranging from 1-10 μg/ml.
Figure 5G:
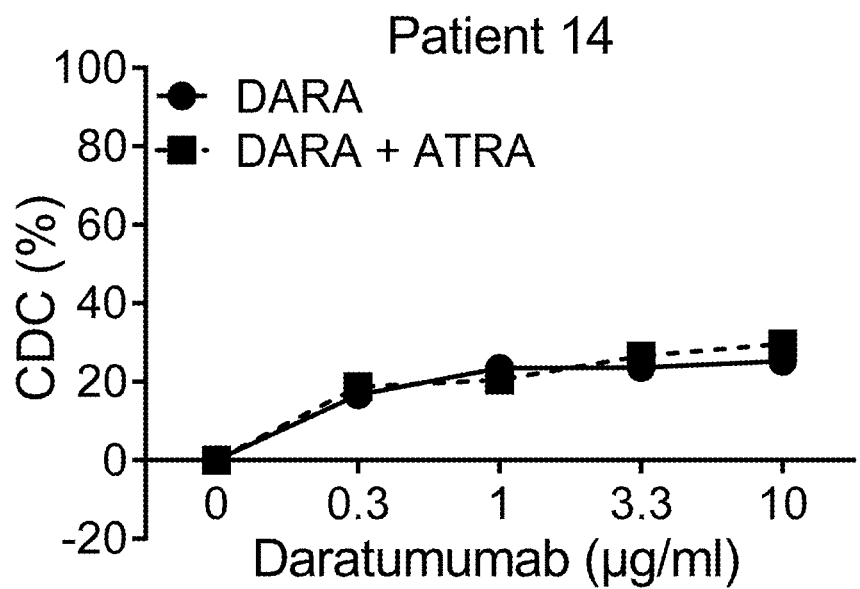
Figure 5H:
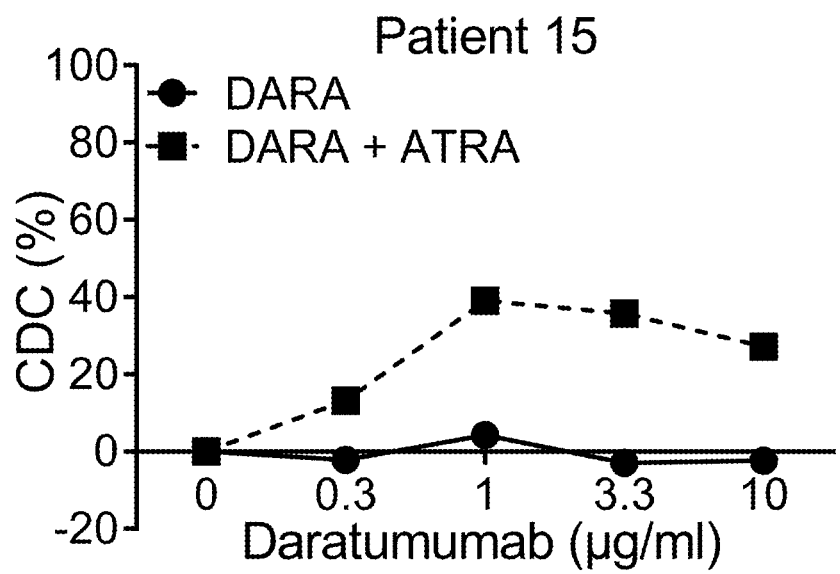
FIG. 5H shows the results of in vitro CDC of primary MM cells isolated from patient 15 and patient 16 pretreated for 48 hours with or without 10 nM ATRA as indicated in the Figure at daratumumab concentrations ranging from 1-10 μg/ml.
Figure 5H:
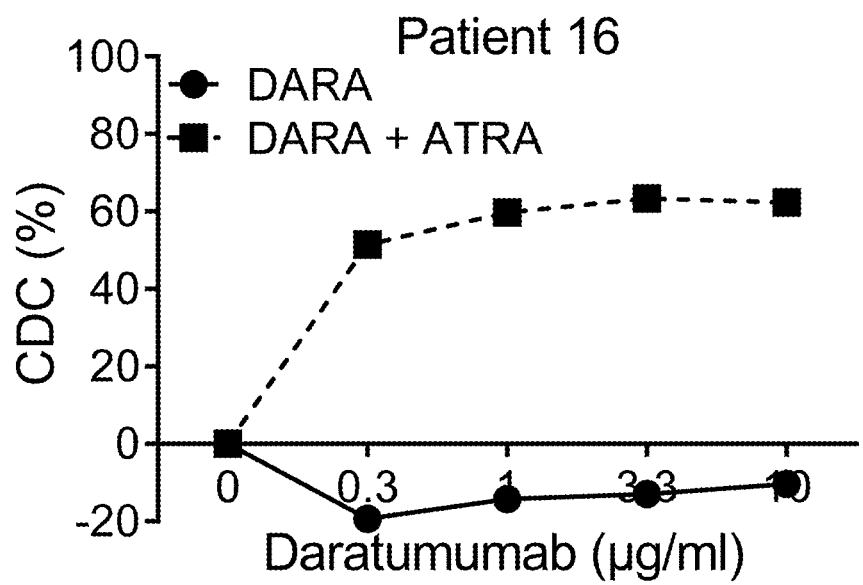
Figure 6A:
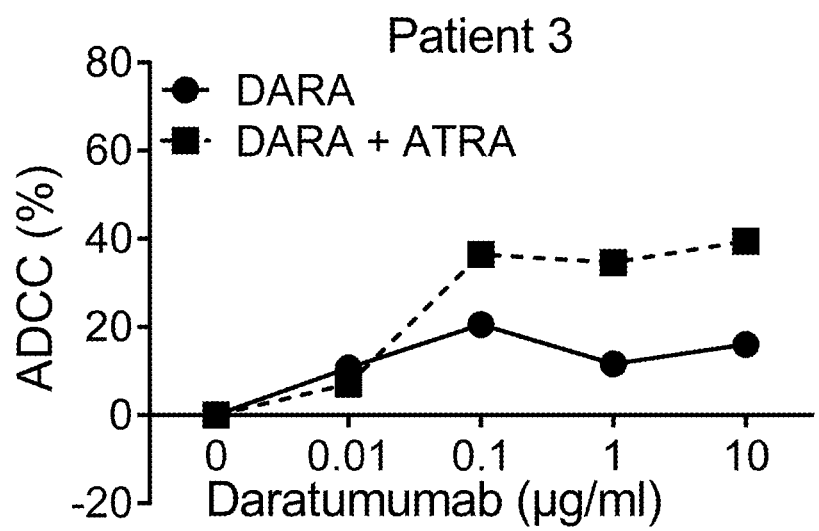
FIG. 6A shows the results of in vitro ADCC of primary MM cells isolated from patient 3 and patient 4 pretreated for 48 hours with or without 10 nM ATRA as indicated in the Figure at daratumumab concentrations ranging from 1-10 μg/ml.
Figure 6A:
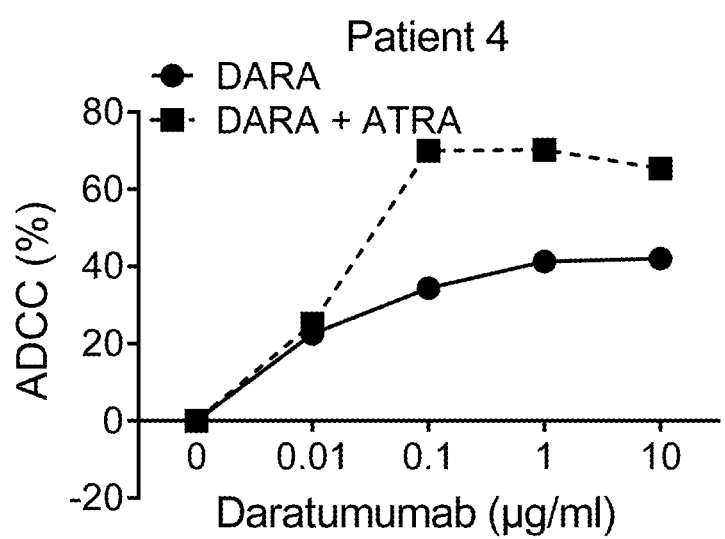
Figure 6B:
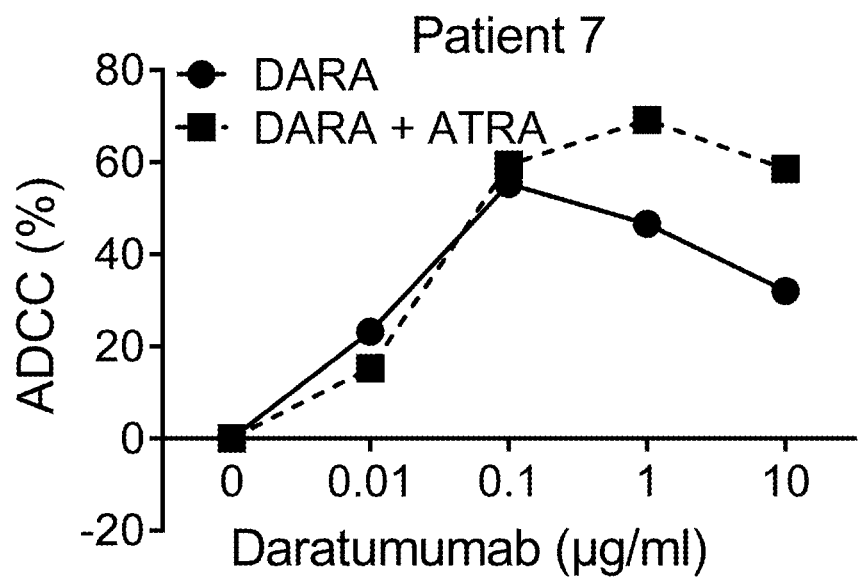
FIG. 6B shows the results of in vitro ADCC of primary MM cells isolated from patient 7 and patient 8 pretreated for 48 hours with or without 10 nM ATRA as indicated in the Figure at daratumumab concentrations ranging from 1-10 μg/ml.
Figure 6B:
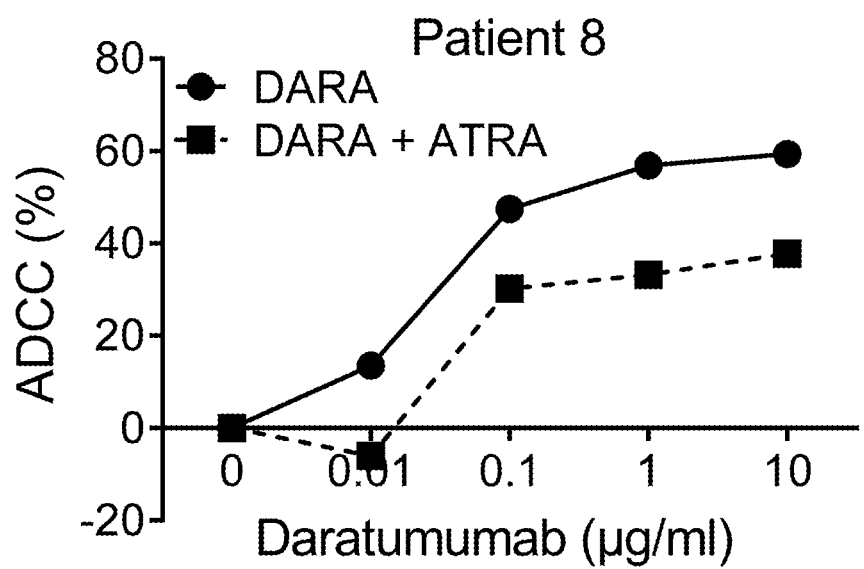
Figure 6C:
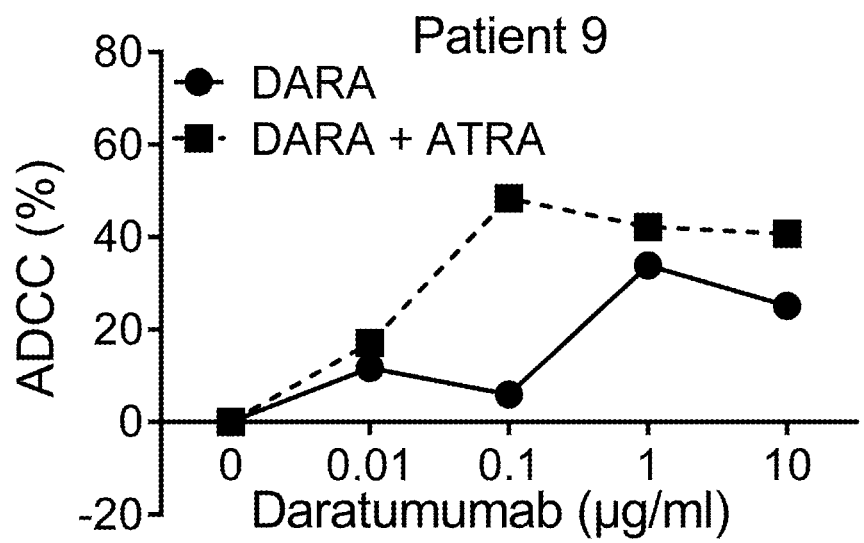
FIG. 6C shows the results of in vitro ADCC of primary MM cells isolated from patient 9 and patient 10 pretreated for 48 hours with or without 10 nM ATRA as indicated in the Figure at daratumumab concentrations ranging from 1-10 μg/ml.
Figure 6C:
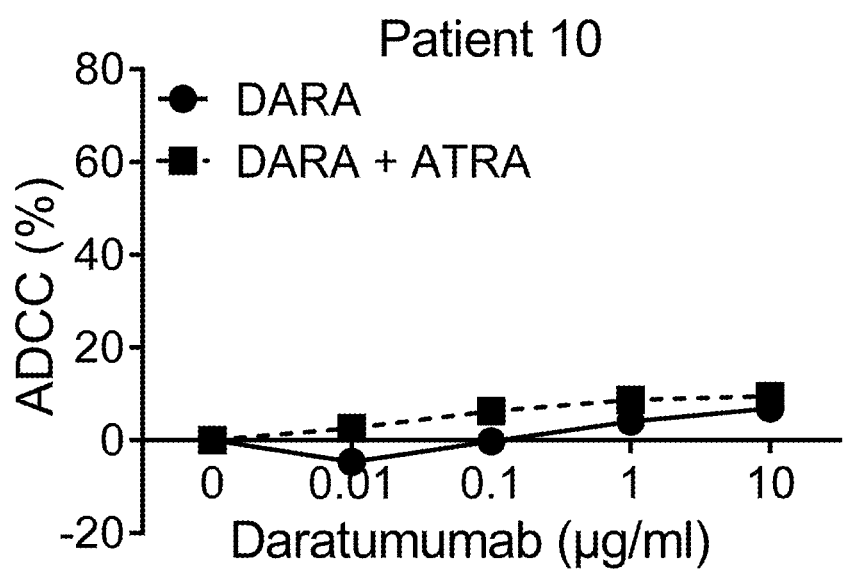
Figure 6D:
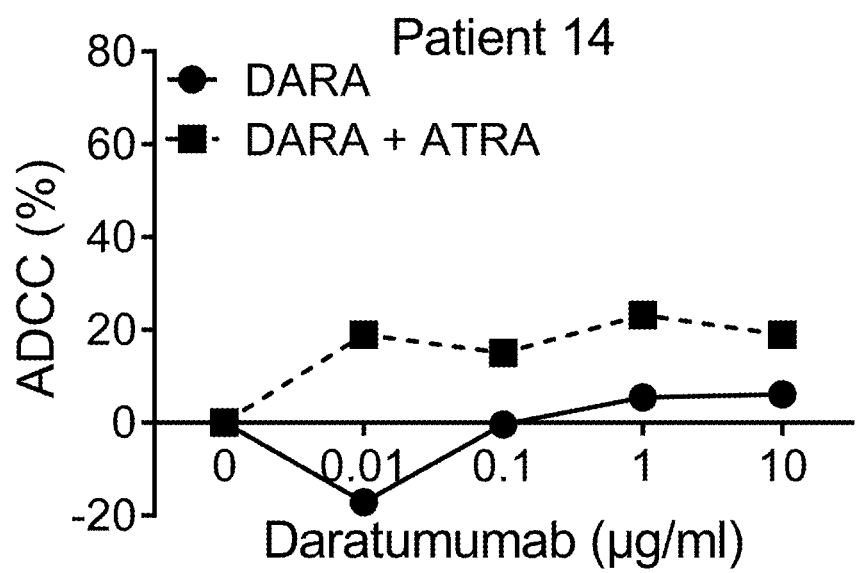
FIG. 6D shows the results of in vitro ADCC of primary MM cells isolated from patient 14 and patient 15 pretreated for 48 hours with or without 10 nM ATRA as indicated in the Figure at daratumumab concentrations ranging from 1-10 μg/ml.
Figure 6D:
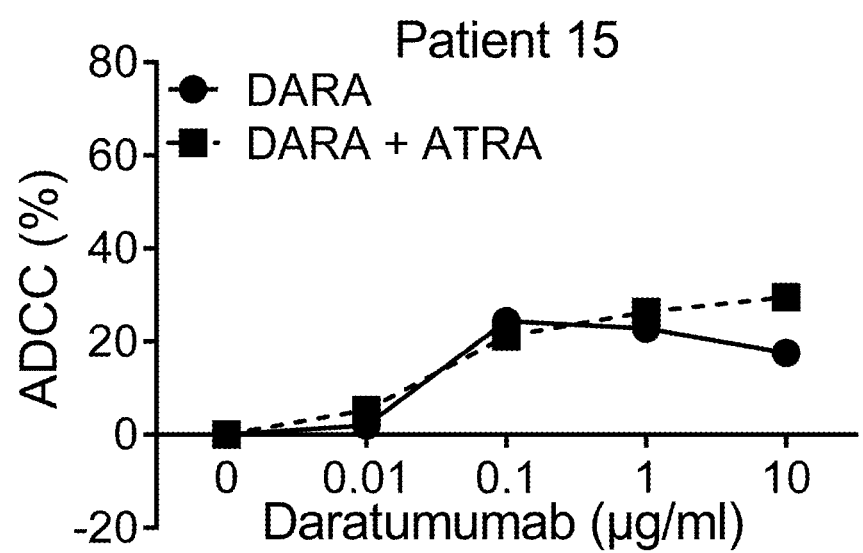
Figure 6E:
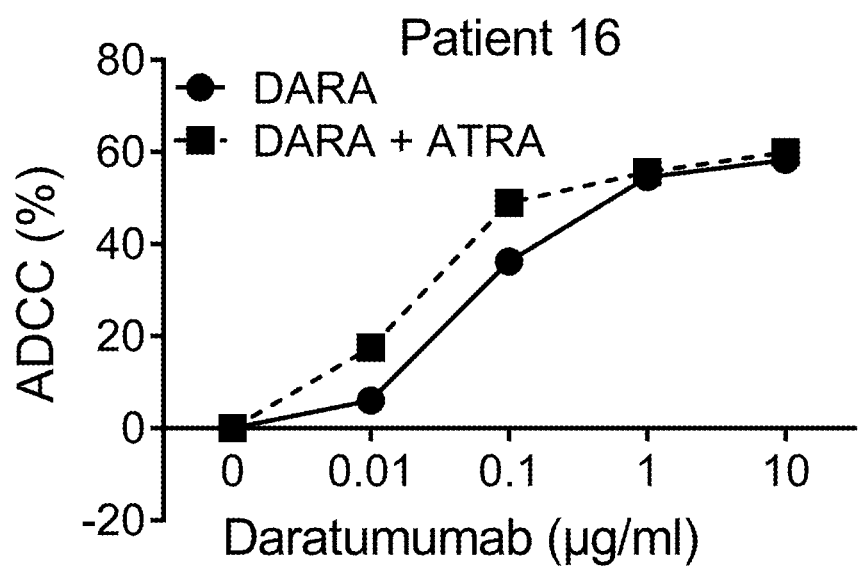
FIG. 6E shows the results of in vitro ADCC of primary MM cells isolated from patient 16 and patient 17 pretreated for 48 hours with or without 10 nM ATRA as indicated in the Figure at daratumumab concentrations ranging from 1-10 μg/ml.
Figure 6E:
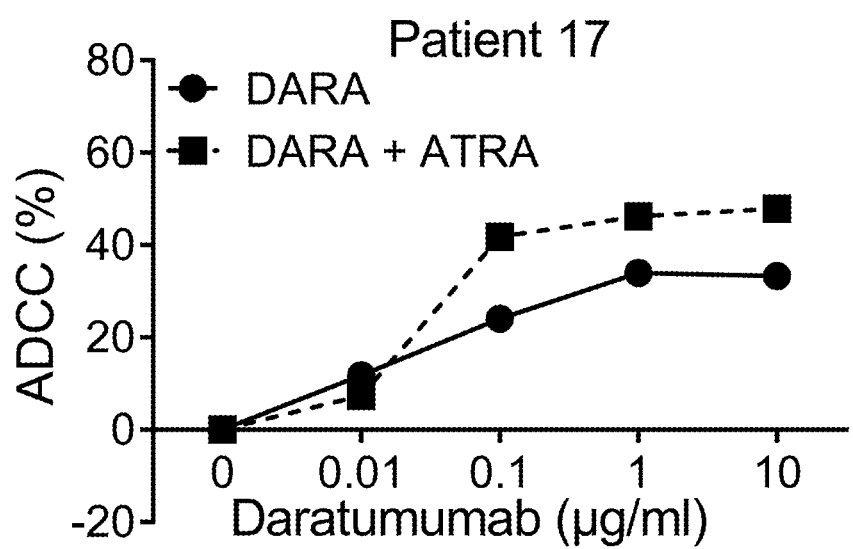
Figure 6F:
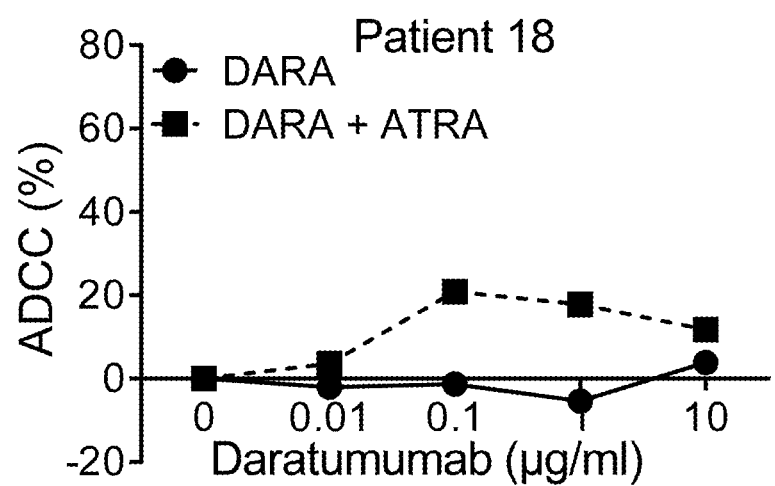
FIG. 6F shows the results of in vitro ADCC of primary MM cells isolated from patient 18 pretreated for 48 hours with or without 10 nM ATRA as indicated in the Figure at daratumumab concentrations ranging from 1-10 μg/ml.

FIG. 4A and FIG. 4B show results of daratumumab-induced CDC and ADCC, respectively, in primary MM cells pretreated for 48 hours with or without 10 nM ATRA. The graphs in FIG. 4A and FIG. 4B represent pooled results of 16 or 13 patient samples, respectively.

In primary MM cells, pretreatment with ATRA for 48 hours resulted in a significant increase in their susceptibility to daratumumab-mediated CDC in 13 out of 16 patients (data not shown) and ADCC in 8 out of 11 patients (data not shown). Pooled results of these patients show that ATRA improved CDC mediated by 10 µg/mL daratumumab median from 16.1% to 43.9% (P<0.0001) (FIG. 4A), and ADCC mediated by 10 µg/mL daratumumab improved median from 25.1% to 39.5% (P=0.0315) by ATRA (FIG. 4B).

FIG. 5 shows results of daratumumab-induced CDC in primary MM cells from each patient. FIG. 5A shows daratumumab-induced CDC in primary MM cells form patient 1 and patient 2. FIG. 5B shows daratumumab-induced CDC in primary MM cells form patient 3 and patient 4. FIG. 5C shows daratumumab-induced CDC in primary MM cells form patient 5 and patient 6. FIG. 5D shows daratumumab-induced CDC in primary MM cells form patient 7 and patient 8. FIG. 5E shows daratumumab-induced CDC in primary MM cells form patient 9 and patient 10. FIG. 5F shows daratumumab-induced CDC in primary MM cells form patient 11 and patient 12. FIG. 5G shows daratumumab-induced CDC in primary MM cells form patient 13 and patient 14. FIG. 5h shows daratumumab-induced CDC in primary MM cells form patient 15 and patient 16. ATRA induced daratumumab-mediated CDC in primary MM cells that were not responsive to daratumumab alone in vitro (for example patients 1, 4, 8, 12, 13, 15 and 16). These primary MM cells were isolated from patients with refractory or double refractory disease as indicated in Table 1. In some patient primary MM cell samples, ATRA had no additional effect enhancing daratumumab-mediated CDC (for example see patients 6, 7 and 14).

FIG. 6 shows results of daratumumab-induced ADCC in primary MM cells from each patient. FIG. 6A shows daratumumab-induced CDC in primary MM cells form patient 3 and patient 4. FIG. 6B shows daratumumab-induced CDC in primary MM cells form patient 7 and patient 8. FIG. 6C shows daratumumab-induced CDC in primary MM cells form patient 9 and patient 10. FIG. 6D shows daratumumab-induced CDC in primary MM cells form patient 14 and patient 15. FIG. 6E shows daratumumab-induced CDC in primary MM cells form patient 16 and patient 17. FIG. 6f shows daratumumab-induced CDC in primary MM cells form patient 18. ATRA induced daratumumab-mediated ADCC most primary MM cells tested. These primary MM cells were isolated from patients with refractory or double refractory disease as indicated in Table 1.

Figure 7:
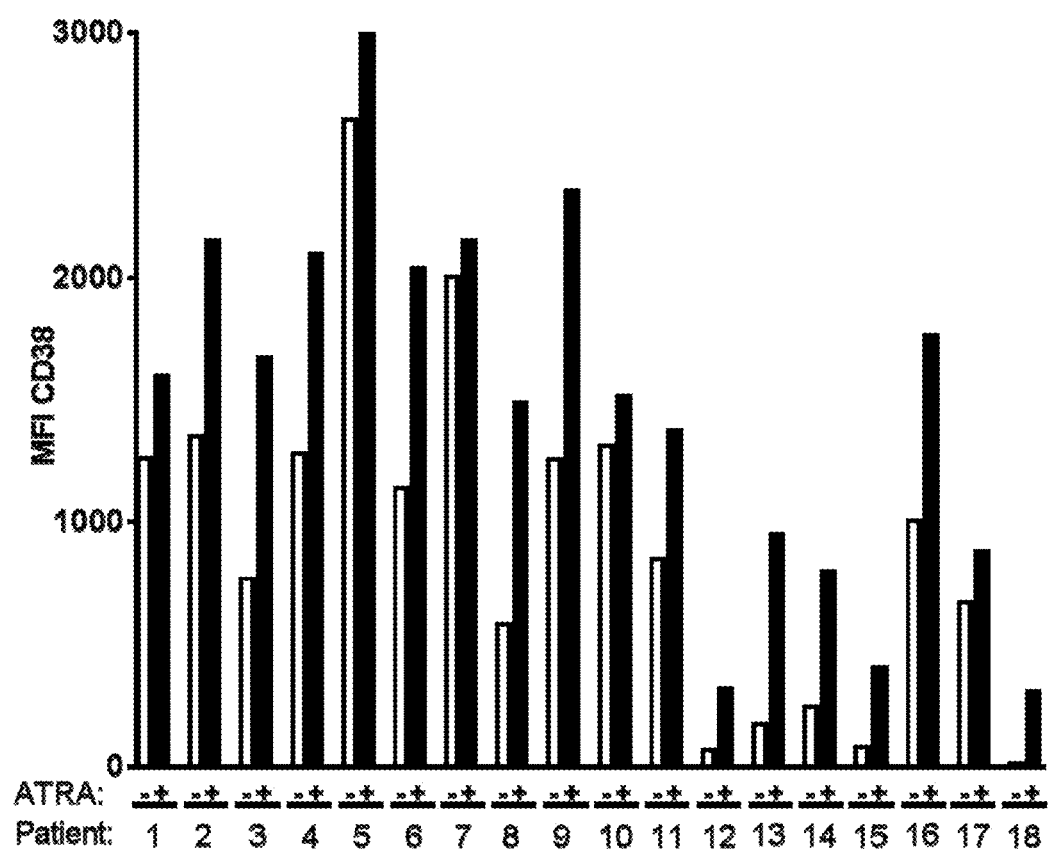
FIG. 7 shows CD38 expression levels in BM-MNCs isolated from MM patients before and after incubation of cells with (black bars) or without (white bars) in the presence of 10 nM ATRA. The same patient samples were used in ADCC and CDC assays as shown in FIGS. 4A, 4B, 5 and 6.

Surface expression of CD38 was also assessed in all these tested primary MM cells in BM-MNCs incubated with RPMI-1640 medium alone or with ATRA 10 nM for 48 hours (FIG. 7).

Overall the results suggest that ATRA is an attractive strategy to improve CD38 expression and daratumumab activity in MM cell lines and in primary MM cells, including MM cells that are refractory to daratumumab-mediated CDC and/or ADCC.

Table 1 shows the baseline characteristics of the BM-MNC of the tested 19 MM patients. In the table, * lenalidomide- and/or bortezomib-refractory disease is defined as progressive disease on lenalidomide- and bortezomib-therapy, no response (less than partial response) to lenalidomide- and bortezomib-therapy, or progressive disease within 60 days of stopping a lenalidomide- and bortezomib-containing regimen, according to the International Uniform Response Criteria for Multiple Myeloma.

TABLE 1

| Parameter: | Patient | | | | | |
|---|---|---|---|---|---|---|
| | 1 | 2 | 3 | 4 | 5 | 6 |
| Age (years) | 71 | 43 | 71 | 64 | 64 | 55 |
| Sex | M | M | F | M | M | F |
| Type of monoclonal heavy chain | IgG | — | — | IgD | — | IgG |
| Type of light chain | K | K | L | K | L | L |
| Previous therapy | | | | | | |
| Prior lines of therapy (number) | 10 | 4 | 4 | 6 | 3 | 0 |
| Prior stem cell transplantation | yes | yes | yes | yes | yes | no |
| Autologous | yes | yes | yes | yes | yes | no |
| Allogeneic | no | no | no | no | no | no |
| Prior lenalidomide treatment, | yes | yes | yes | yes | yes | no |
| lenalidomide refractory status* | yes | yes | yes | yes | yes | no |
| Prior bortezomib treatment | yes | yes | yes | yes | yes | no |
| bortezomib refractory status* | yes | yes | yes | yes | yes | no |
| CD38 expression on MM cells (MFI) | 1258 | 1346 | 764 | 1275 | 2642 | 1134 |
| CD46 expression on MM cells (MFI) | 1165 | 264 | 866 | 1346 | 661 | 1124 |
| CD55 expression on MM cells (MFI) | 610 | 119 | 552 | 227 | 1 | 594 |
| CD59 expression on MM cells (MFI) | 235 | 62 | 228 | 108 | 7 | 90 |

| Parameter: | Patient | | | | | |
|---|---|---|---|---|---|---|
| | 7 | 8 | 9 | 10 | 11 | 12 |
| Age (years) | 55 | 64 | 75 | 63 | 56 | 59 |
| Sex | F | M | M | F | M | M |
| Type of monoclonal heavy chain | IgA | — | — | IgA | IgA | — |
| Type of light chain | L | K | L | K | K | K |
| Previous therapy | | | | | | |
| Prior lines of therapy (number) | 2 | 2 | 5 | 6 | 2 | 4 |
| Prior stem cell transplantation | yes | yes | no | yes | yes | yes |
| Autologous | yes | yes | no | yes | yes | yes |
| Allogeneic | no | no | no | no | no | no |
| Prior lenalidomide treatment, | no | yes | yes | yes | yes | yes |
| lenalidomide refractory status* | no | yes | yes | yes | no | yes |
| Prior bortezomib treatment | yes | yes | yes | yes | no | yes |
| bortezomib refractory status* | yes | no | yes | yes | no | no |
| CD38 expression on MM cells (MFI) | 1999 | 578 | 1252 | 1310 | 843 | 64 |
| CD46 expression on MM cells (MFI) | 2288 | 4870 | 1700 | 196 | 368 | 264 |
| CD55 expression on MM cells (MFI) | 655 | 528 | 813 | 4 | 362 | 60 |
| CD59 expression on MM cells (MFI) | 92 | 151 | 241 | 7 | 74 | 47 |

| Parameter: | Patient | | | | | |
|---|---|---|---|---|---|---|
| | 13 | 14 | 15 | 16 | 17 | 18 |
| Age (years) | 71 | 72 | 67 | 64 | 63 | 53 |
| Sex | F | M | M | M | M | M |
| Type of monoclonal heavy chain | — | — | IgG | — | IgG | IgA |
| Type of light chain | L | K | K | K | L | K |
| Previous therapy | | | | | | |
| Prior lines of therapy (number) | 4 | 5 | 2 | 3 | 4 | 2 |
| Prior stem cell transplantation | yes | no | no | yes | yes | yes |
| Autologous | yes | no | no | yes | yes | yes |
| Allogeneic | no | no | no | no | no | no |
| Prior lenalidomide treatment, | yes | yes | yes | yes | no | yes |
| lenalidomide refractory status* | yes | yes | yes | yes | no | yes |
| Prior bortezomib treatment | yes | yes | yes | yes | yes | yes |
| bortezomib refractory status* | yes | yes | no | yes | no | yes |
| CD38 expression on MM cells (MFI) | 173 | 241 | 78 | 1000 | 667 | 11 |

TABLE 1-continued

| | | | | | | |
|---|---|---|---|---|---|---|
| CD46 expression on MM cells (MFI) | 300 | 492 | 362 | 491 | 538 | 557 |
| CD55 expression on MM cells (MFI) | 379 | 1275 | 59 | 176 | 231 | 519 |
| CD59 expression on MM cells (MFI) | 188 | 75 | 9 | 107 | 70 | 52 |

BM-MNCs; bone marrow mononuclear cells.
MM; multiple myeloma.
M; male.
F; female.
K; kappa.
L; lambda.

EXAMPLE 5

ATRA Downregulates CD55 and CD59 Expression in Primary MM Cells

The experiments conducted revealed that the pretreatment of MM cells with ATRA rendered these cells more susceptible to daratumumab-mediated ADCC and CDC. The improvement in CDC was more pronounced than the enhancement of ADCC. The molecular basis for the observation was assessed.

Figure 8A:
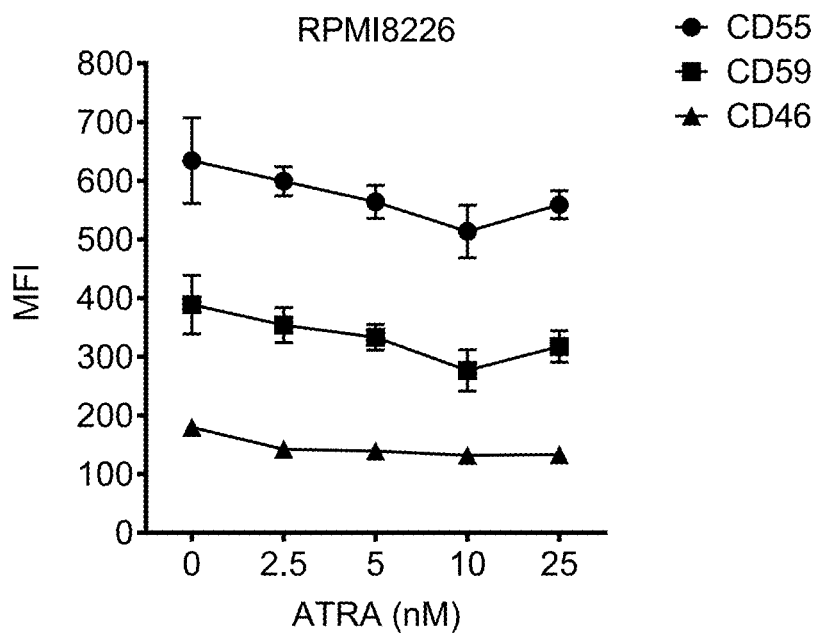
FIG. 8A shows ATRA-induced reduction of CD55, CD59 and CD46 expression on RPMI8226 cells after 48 hour incubation of cells with 0-25 nM ATRA. MFI; mean fluorescent intensity. Expression of CD55, CD59 and CD46 were assessed using flow cytometry. Top panel: MFI; bottom panel: MFI fold change when compared to control.
Figure 8A:
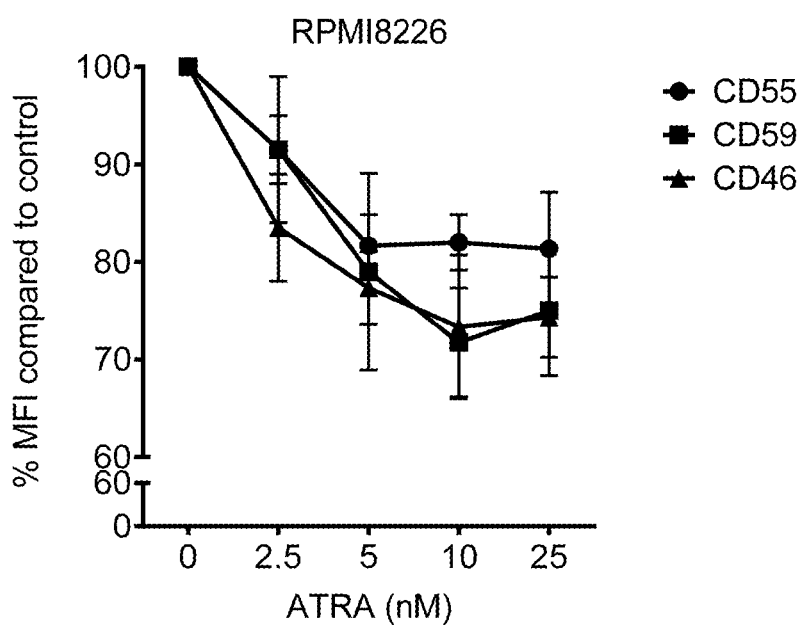
Figure 8B:
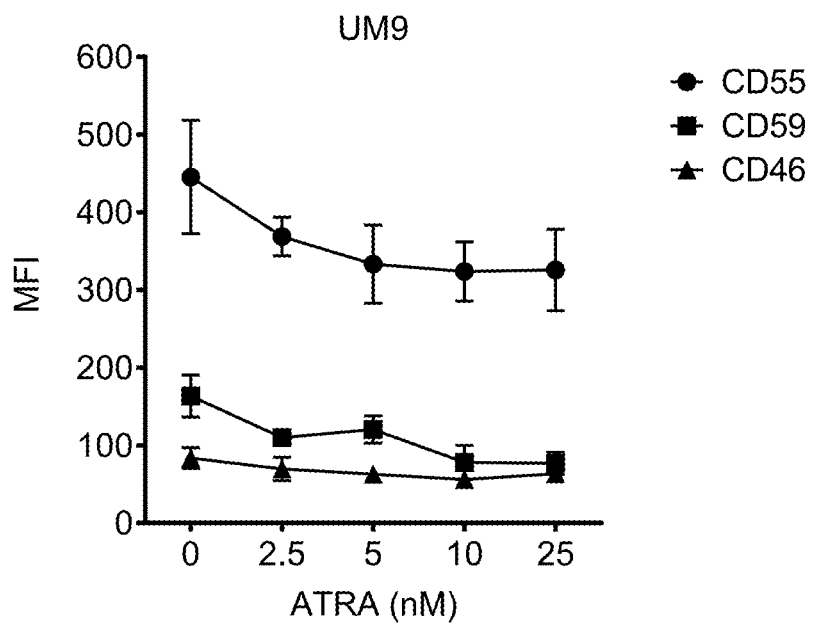
FIG. 8B shows ATRA-induced reduction of CD55, CD59 and CD46 expression on UM9 cells after 48 hour incubation of cells with 0-25 nM ATRA. MFI; mean fluorescent intensity. Expression of CD55, CD59 and CD46 were assessed using flow cytometry. Top panel: MFI; bottom panel: MFI fold change when compared to control.
Figure 8B:
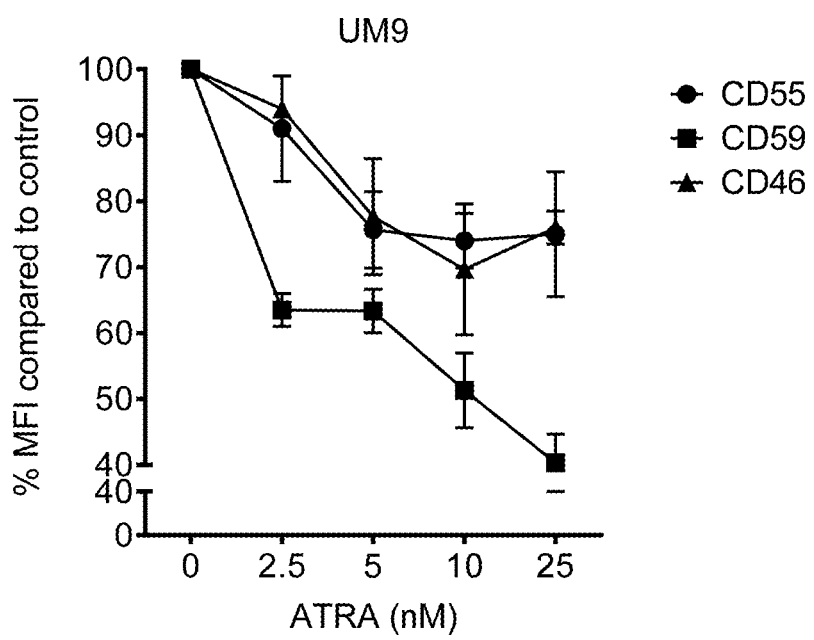
Figure 8C:
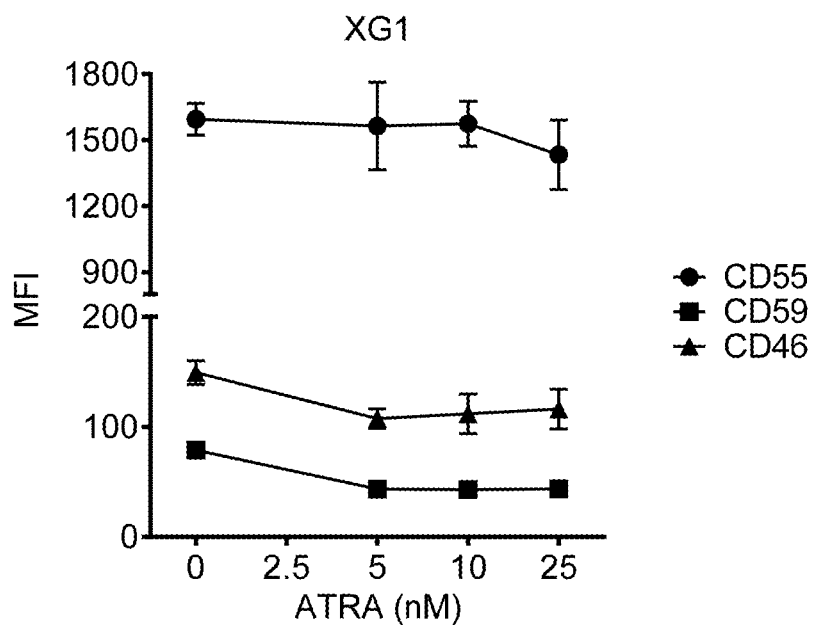
FIG. 8C shows ATRA-induced reduction of CD55, CD59 and CD46 expression on XG1 cells after 48 hour incubation of cells with 0-25 nM ATRA. MFI; mean fluorescent intensity. Expression of CD55, CD59 and CD46 were assessed using flow cytometry. Top panel: MFI; bottom panel: MFI fold change when compared to control.
Figure 8C:
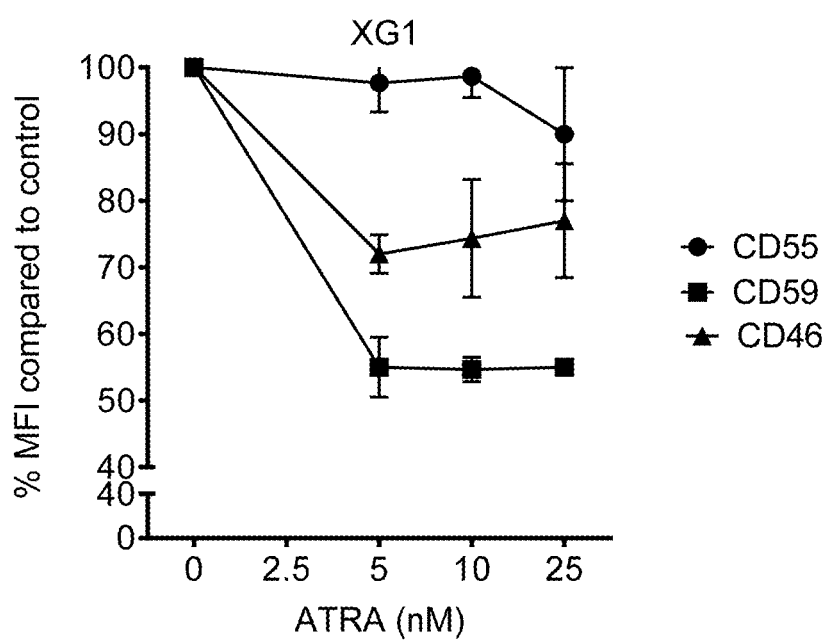
Figure 9A:
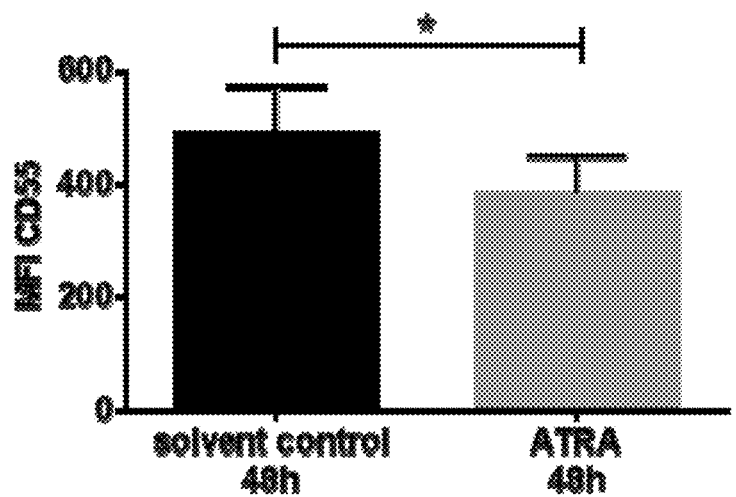
FIG. 9A shows ATRA-induced reduction of CD55 expression on primary MM cells after 48 hour incubation of cells with (grey bars) or without (black bars) in 10 nM ATRA as indicated. * p=0.019.
Figure 9B:
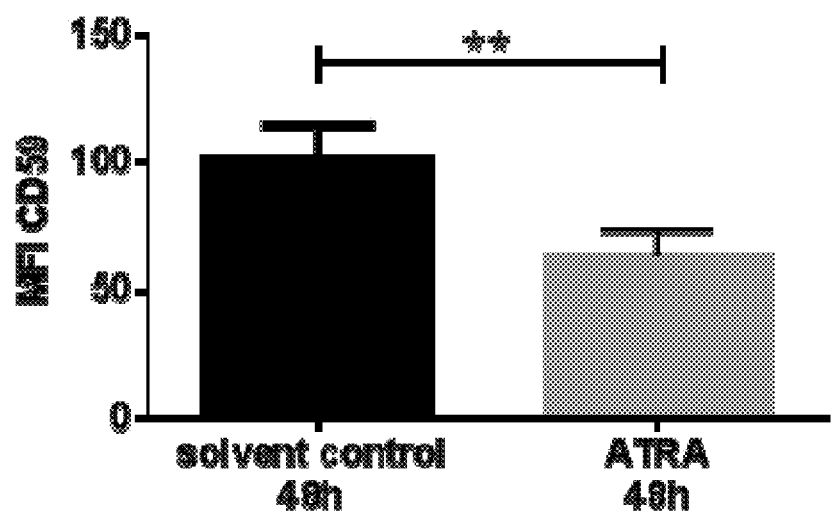
FIG. 9B shows ATRA-induced reduction of CD59 expression on primary MM cells after 48 hour incubation of cells with (grey bars) or without (black bars) in 10 nM ATRA as indicated. ** p=0.0047.
Figure 9C:
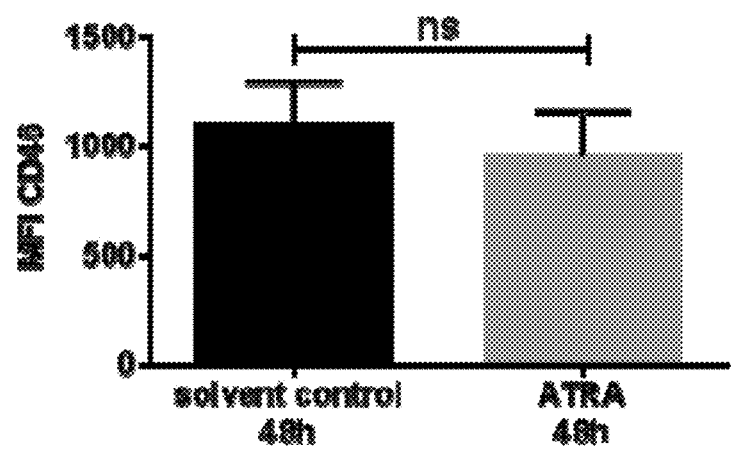
FIG. 9C shows effect of ATRA on CD46 expression on primary MM cells after 48 hour incubation of cells with (grey bars) or without (black bars) in 10 nM ATRA as indicated. ns: not significant.
Figure 10A:
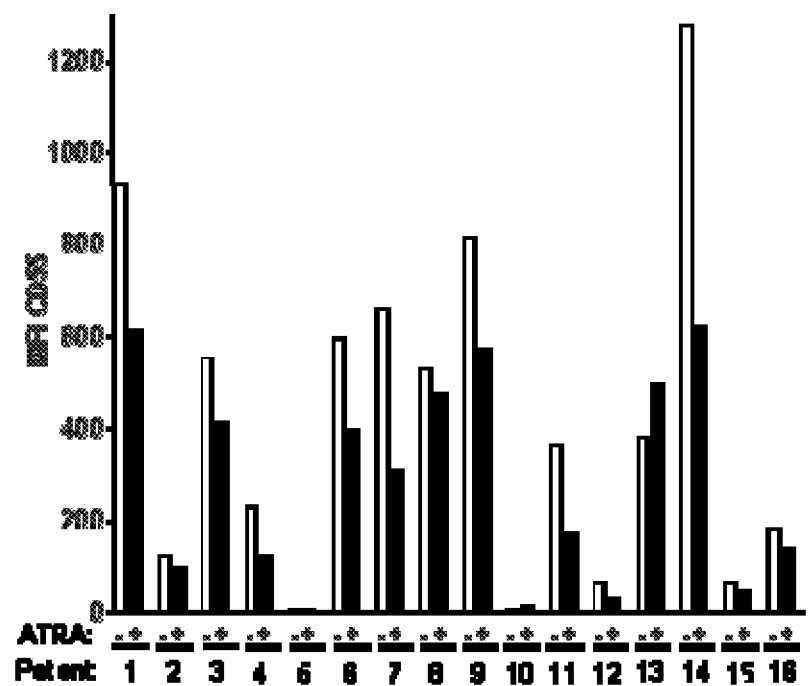
FIG. 10A shows CD55 expression on primary MM cells isolated from 16 MM patients after 48 hour incubation of cells with (black bars) or without (white bars) 10 nM ATRA. The same patient samples were used in CDC assays as shown in FIG. 5.
Figure 10B:
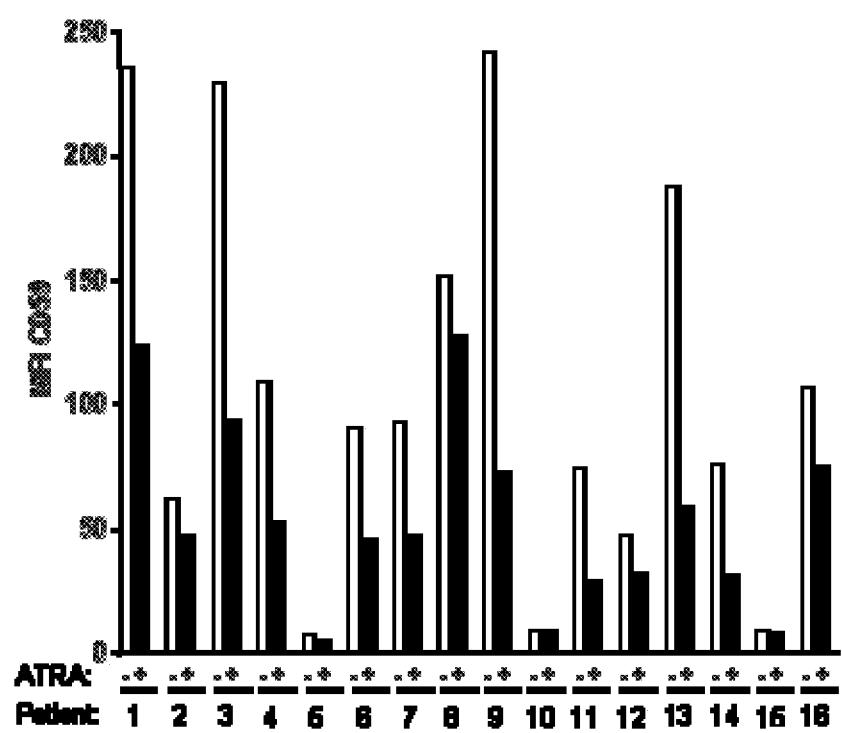
FIG. 10B shows CD59 expression on primary MM cells isolated from 16 MM patients after 48 hour incubation of cells with (black bars) or without (white bars) 10 nM ATRA. The same patient samples were used in CDC assays as shown in FIG. 5.
Figure 10C:
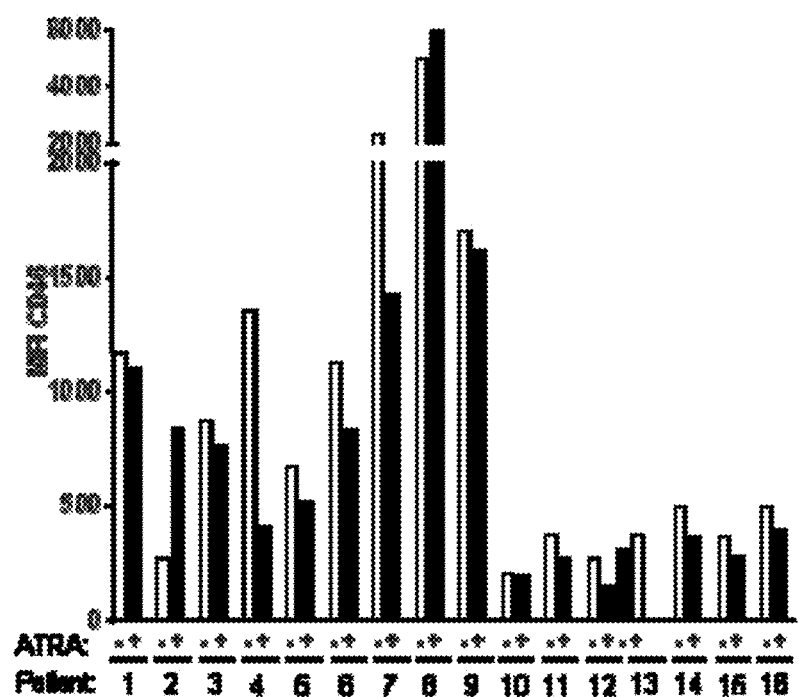
FIG. 10C shows CD46 expression on primary MM cells isolated from 16 MM patients after 48 hour incubation of cells with (black bars) or without (white bars) 10 nM ATRA. The same patient samples were used in CDC assays as shown in FIG. 5.

The effect of ATRA on effector cells was evaluated. ATRA had no effect or minimal effect on the ability of PBMCs from healthy donors to induce ADCC on human MM cell lines L363-CD38, LME-1, RPMI8226 and UM9 (data not shown). On the contrary, ATRA reduced expression levels of complement-inhibitory proteins CD55, CD59 and CD46 on MM cell lines and primary MM cells. In RPMI8226 (FIG. 8A), L363 (FIG. 8B) and XG-1 (FIG. 8C) cells, ATRA reduced expression levels of CD55, CD59, and CD46. In primary MM cells derived from 16 patients, ATRA significantly reduced the expression of CD55 (mean reduction 21.3%, P=0.019) (FIG. 9A) and CD59 (mean reduction 37.5%, P=0.0047) (FIG. 9B), while ATRA did not significantly affect CD46 expression levels (data not shown). The CD46, CD55 and CD59 expression levels from the tested 16 patients' samples are shown in FIGS. 10A (CD55), FIG. 10B (CD59) and FIG. 10C (CD46). In the experiments, cells were cultured at 37° C. with RPMI-1640 medium with or without 10 nM ATRA 10 nM for 48 h. Cells were then incubated at 4° C. for 20 min with the appropriate conjugated antibodies panel. Flow cytometric analyses were performed using a FACS-Calibur device (Becton Dickinson); the data were analyzed using the CellQuest software.

EXAMPLE 6

In Vivo Efficacy of the Combination of ATRA and Daratumumab Against MM Tumors Growing in a Humanized Microenvironment Hybrid scaffolds consisting of three 2-3 mm biphasic calcium phosphate particles were coated in vitro with human mesenchymal stromal cells (MSCs; $2\times10^5$ cells/scaffold). After a week of in vitro culture in a osteogenic medium, humanized scaffolds were implanted subcutaneously into $RAG2^{-/-}\gamma c^{-/-}$ mice, as described previously (Groen et al., Blood. 19; 120:e9-e16, 2012; de Haart et al., Clin. Cancer Res. 19:5591-5601, 2013).

Eight weeks after implantation, mice received a sublethal irradiation dose (3 Gy, 200 kV, 4 mA) and luciferase-transduced XG1 cells were injected directly into the scaffold ($1\times10^6$ cells/scaffold). Three weeks after inoculation, when there was visible tumor growth in the scaffolds by bioluminescent imaging (BLI), different groups of mice were treated with 1) vehicle, 2) ATRA plus T-cell depleted PBMC as effector cells (PBMC-T), 3) daratumumab plus PBMC-T, and 4) daratumumab plus ATRA plus PBMC-T. Daratumumab (8 mg/kg) was given intraperitoneally on days 23, 30, and 37; PBMC-T ($8\times10^6$ cells/mouse) were given intravenously on days 24, 31, and 38; and ATRA (10 mg/kg) was given via intraperitoneal injection on days 21-24, 28-31, and 35-38. PBMC-T were prepared by Ficoll-Hypaque density-gradient centrifugation of buffy coats, and subsequent depletion of T cells by CD3-beads using the Easy Sep™-technology (STEMCELL Technologies). Tumor growth was monitored by weekly BLI measurements as described previously (Groen et al., Blood. 19; 120:e9-e16, 2012). All animal experiments were conducted after acquiring permission from the local ethical committee for animal experimentation and were in compliance with the Dutch Animal Experimentation Act. The statistical differences between the different treatment groups in the mice experiments were calculated using a Mann-Whitney test. P-values below 0.05 were considered significant.

Figure 11:
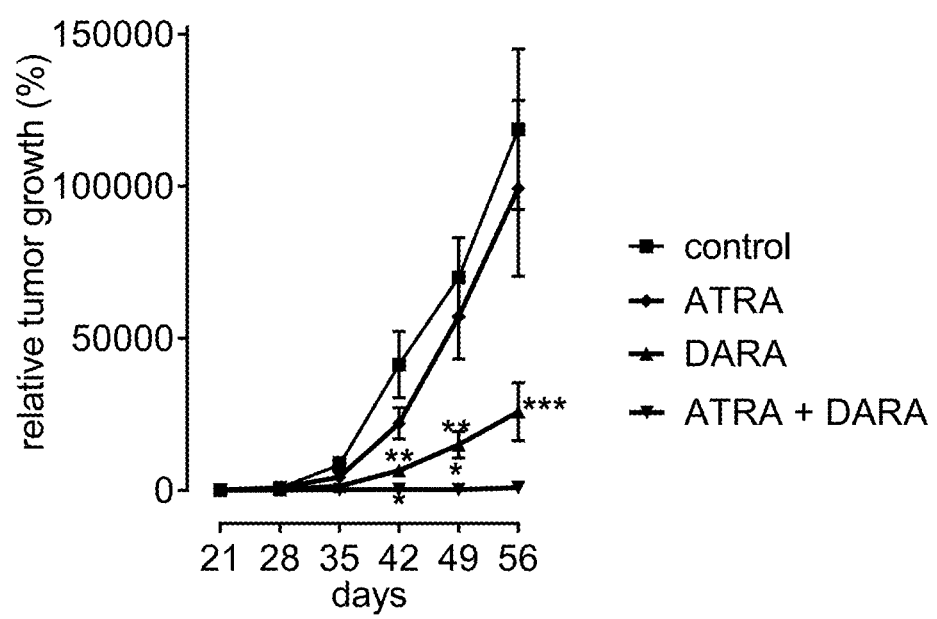
FIG. 11 shows that ATRA improves response to daratumumab in a humanized multiple myeloma mouse model. $Rag2^{-/-}\gamma_c^{-/-}$ mice carrying mesenchymal stem cell (MSC)-coated scaffolds were inoculated with luciferase-transduced XG1 cells. Mice were treated with control, ATRA plus T-cell depleted PBMCs as effector cells (PBMC-T), daratumumab plus PBMC-T, or daratumumab plus ATRA plus PBMC-T, and monitored weekly by bioluminescent imaging (BLI) for growth of the transduced XG1 cells. The Figure shows tumor load per treatment group with 4 mice per group and each mouse with 4 scaffolds. Statistical differences between mice treated with daratumumab and mice treated with daratumumab plus ATRA were calculated using the Mann-Whitney U-test. * $P<0.05$,  $P<0.01$, * $P<0.001$; ns: not significant.

Luciferase-transduced XG1 multiple myeloma cells developed into aggressive tumors in immunodeficient $RAG2^{-/-}\gamma_c^{-/-}$ mice in a humanized bone marrow microenvironment generated by subcutaneous implantation of MSC-coated ceramic scaffolds. To optimally evaluate the effects of daratumumab and ATRA, mice were co-injected with NK cell-enriched (T cell-depleted) PBMCs of a healthy donor in combination with daratumumab and/or ATRA, as $RAG2^{-/-}\gamma_c^{-/-}$ mice are devoid of NK cells. To follow the outgrowth of the tumor, BLI was performed weekly for 5 weeks. As shown in FIG. 11, daratumumab markedly slowed tumor progression, whereas ATRA as single agent had no effect. ATRA also significantly enhanced the anti-MM effect of daratumumab in this model.

The invention claimed is:

1. A method of treating a subject having a refractory or resistant CD38-positive multiple myeloma (MM), comprising administering to the subject in need thereof an anti-CD38 antibody in combination with all-trans retinoic acid (ATRA), wherein the anti-CD38 antibody comprises the heavy chain complementarity determining regions (HCDR) 1 (HCDR1), 2 (HCDR2) and 3 (HCDR3) sequences of SEQ ID NOs: 6, 7 and 8, respectively, and the light chain complementarity determining regions (LCDR) 1(LCDR1), 2 (LCDR2) and 3 (LCDR3) sequences of SEQ ID NOs: 9, 10 and 11, respectively, and wherein the subject is resistant to or has acquired resistance to treatment with the anti-CD38 antibody or a combination of at least one chemotherapeutic agent and the anti-CD38 antibody.

2. The method of claim 1, wherein the anti-CD38 antibody induces killing of CD38-expressing cells in vitro by antibody-dependent cell-mediated cytotoxicity (ADCC) or complement dependent cytotoxicity (CDC).

3. The method of claim 2, wherein the anti-CD38 antibody induces killing of the CD38-expressing cells by CDC in vitro.

4. The method of claim 2, wherein the anti-CD38 antibody induces killing of the CD38-expressing cells by ADCC in vitro.

5. The method of claim 1, wherein the at least one chemotherapeutic agent is lenalidomide, bortezomib, melphalan, dexamethasone or thalidomide.

6. The method of claim 5, wherein the at least one chemotherapeutic agent is lenalidomide or bortezomib.

7. The method of claim 1, wherein the anti-CD38 antibody is of IgG1, IgG2, IgG3 or IgG4 isotype.

8. The method of claim 7, wherein the anti-CD38 antibody is of IgG1 isotype.

9. The method of claim 1, wherein the anti-CD38 antibody binds to the region SKRNIQFSCKNIYR (SEQ ID NO: 2) and the region EKVQTLEAWVIHGG (SEQ ID NO: 3) of human CD38 (SEQ ID NO: 1).

10. The method of claim 1, wherein the anti-CD38 antibody comprises the heavy chain variable region (VH) of SEQ ID NO: 4 and the light chain variable region (VL) of SEQ ID NO: 5.

11. The method of claim 1, wherein the anti-CD38 antibody comprises a heavy chain comprising an amino acid sequence that is 95%, 96%, 97%, 98% or 99% identical to that of SEQ ID NO: 12 and a light chain comprising an amino acid sequence that is 95%, 96%, 97%, 98% or 99% identical to that of SEQ ID NO: 13.

12. The method of claim 1, wherein the anti-CD38 antibody comprises the heavy chain of SEQ ID NO: 12 and the light chain of SEQ ID NO: 13.

13. The method of claim 1, wherein administering to the subject the anti-CD38 antibody in combination with the ATRA results in inducing the complement-dependent cytotoxicity or antibody-dependent cell-mediated cytotoxicity of the anti-CD38 antibody.

14. The method of claim 1, wherein administering to the subject the anti-CD38 antibody in combination with the ATRA results in augmented anti-CD38 antibody-induced complement-dependent cytotoxicity of the anti-CD38 antibody.

15. The method of claim 1, wherein administering to the subject the anti-CD38 antibody in combination with the ATRA results in slowing of tumor growth in the subject.

16. A method of augmenting anti-CD38 antibody-induced complement-dependent cytotoxicity in a subject having a refractory or resistant CD38-positive multiple myeloma, comprising:
    administering to the subject in need thereof the anti-CD38 antibody in combination with all-trans retinoic acid,
    wherein the anti-CD38 antibody comprises the heavy chain complementarity determining regions (HCDR) 1 (HCDR1), 2 (HCDR2) and 3 (HCDR3) sequences of SEQ ID NOs: 6, 7 and 8, respectively, and the light chain complementarity determining regions (LCDR) 1 (LCDR1), 2 (LCDR2) and 3 (LCDR3) sequences of SEQ ID NOs: 9, 10 and 11, respectively, and
    wherein the subject is resistant to or has acquired resistance to treatment with at least one chemotherapeutic agent, the anti-CD38 antibody, or a combination of at least one chemotherapeutic agent and the anti-CD38 antibody.

17. A method of inducing anti-CD38 antibody-mediated cytotoxicity in a subject having a refractory or resistant CD38-positive multiple myeloma, comprising:
    administering to the subject in need thereof the anti-CD38 antibody in combination with all-trans retinoic acid,
    wherein the anti-CD38 antibody comprises the heavy chain complementarity determining regions (HCDR) 1 (HCDR1), 2 (HCDR2) and 3 (HCDR3) sequences of SEQ ID NOs: 6, 7 and 8, respectively, and the light chain complementarity determining regions (LCDR) 1 (LCDR1), 2 (LCDR2) and 3 (LCDR3) sequences of SEQ ID NOs: 9, 10 and 11, respectively,
    and wherein the subject is resistant to or has acquired resistance to treatment with at least one chemotherapeutic agent, the anti-CD38 antibody, or a combination of at least one chemotherapeutic agent and the anti-CD38 antibody,
    and further wherein the cytotoxicity is complement-dependent cytotoxicity or antibody-dependent cell-mediated cytotoxicity.

18. The method of claim 17, wherein the cytotoxicity is complement-dependent cytotoxicity.

* * * * *

SEQUENCE LISTING

<160> NUMBER OF SEQ ID NOS: 22

<210> SEQ ID NO 1
<211> LENGTH: 300
<212> TYPE: PRT
<213> ORGANISM: Homo sapiens

<400> SEQUENCE: 1

Met Ala Asn Cys Glu Phe Ser Pro Val Ser Gly Asp Lys Pro Cys Cys
1               5                   10                  15

Arg Leu Ser Arg Arg Ala Gln Leu Cys Leu Gly Val Ser Ile Leu Val
            20                  25                  30

Leu Ile Leu Val Val Leu Ala Val Val Pro Arg Trp Arg Gln
        35                  40                  45

Gln Trp Ser Gly Pro Gly Thr Thr Lys Arg Phe Pro Glu Thr Val Leu
    50                  55                  60

Ala Arg Cys Val Lys Tyr Thr Glu Ile His Pro Glu Met Arg His Val
65              70                  75                  80

Asp Cys Gln Ser Val Trp Asp Ala Phe Lys Gly Ala Phe Ile Ser Lys
                85                  90                  95

His Pro Cys Asn Ile Thr Glu Glu Asp Tyr Gln Pro Leu Met Lys Leu
            100                 105                 110

Gly Thr Gln Thr Val Pro Cys Asn Lys Ile Leu Leu Trp Ser Arg Ile
        115                 120                 125

Lys Asp Leu Ala His Gln Phe Thr Gln Val Gln Arg Asp Met Phe Thr
130                 135                 140

Leu Glu Asp Thr Leu Leu Gly Tyr Leu Ala Asp Asp Leu Thr Trp Cys
145                 150                 155                 160

Gly Glu Phe Asn Thr Ser Lys Ile Asn Tyr Gln Ser Cys Pro Asp Trp
                165                 170                 175

Arg Lys Asp Cys Ser Asn Asn Pro Val Ser Val Phe Trp Lys Thr Val
            180                 185                 190

Ser Arg Arg Phe Ala Glu Ala Ala Cys Asp Val Val His Val Met Leu
        195                 200                 205

Asn Gly Ser Arg Ser Lys Ile Phe Asp Lys Asn Ser Thr Phe Gly Ser
210                 215                 220

Val Glu Val His Asn Leu Gln Pro Glu Lys Val Gln Thr Leu Glu Ala
225                 230                 235                 240

Trp Val Ile His Gly Gly Arg Glu Asp Ser Arg Asp Leu Cys Gln Asp
                245                 250                 255

Pro Thr Ile Lys Glu Leu Glu Ser Ile Ser Lys Arg Asn Ile Gln
            260                 265                 270

Phe Ser Cys Lys Asn Ile Tyr Arg Pro Asp Lys Phe Leu Gln Cys Val
        275                 280                 285

Lys Asn Pro Glu Asp Ser Ser Cys Thr Ser Glu Ile
290                 295                 300

<210> SEQ ID NO 2
<211> LENGTH: 14
<212> TYPE: PRT
<213> ORGANISM: Homo sapiens

<400> SEQUENCE: 2

Ser Lys Arg Asn Ile Gln Phe Ser Cys Lys Asn Ile Tyr Arg
1               5                   10

<210> SEQ ID NO 3
<211> LENGTH: 14
<212> TYPE: PRT
<213> ORGANISM: Homo sapiens

<400> SEQUENCE: 3

Glu Lys Val Gln Thr Leu Glu Ala Trp Val Ile His Gly Gly

<210> SEQ ID NO 4
<211> LENGTH: 122
<212> TYPE: PRT
<213> ORGANISM: Artificial Sequence
<220> FEATURE:
<223> OTHER INFORMATION: VH of anti-CD38 antibody

<400> SEQUENCE: 4

```
Glu Val Gln Leu Leu Glu Ser Gly Gly Gly Leu Val Gln Pro Gly Gly
1               5                   10                  15

Ser Leu Arg Leu Ser Cys Ala Val Ser Gly Phe Thr Phe Asn Ser Phe
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Lys Asp Lys Ile Leu Trp Phe Gly Glu Pro Val Phe Asp Tyr Trp
            100                 105                 110

Gly Gln Gly Thr Leu Val Thr Val Ser Ser
        115                 120
```

<210> SEQ ID NO 5
<211> LENGTH: 107
<212> TYPE: PRT
<213> ORGANISM: Artificial Sequence
<220> FEATURE:
<223> OTHER INFORMATION: VL of anti-CD38 antibody

<400> SEQUENCE: 5

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Thr Phe Gly Gln Gly Thr Lys Val Glu Ile Lys
            100                 105
```

<210> SEQ ID NO 6
<211> LENGTH: 5
<212> TYPE: PRT
<213> ORGANISM: Artificial Sequence
<220> FEATURE:
<223> OTHER INFORMATION: HCDR1 of anti-CD38 antibody

<400> SEQUENCE: 6

```
Ser Phe Ala Met Ser
1               5
```

<210> SEQ ID NO 7
<211> LENGTH: 17
<212> TYPE: PRT
<213> ORGANISM: Artificial Sequence
<220> FEATURE:
<223> OTHER INFORMATION: HCDR2 of anti-CD38 antibody

<400> SEQUENCE: 7

Ala Ile Ser Gly Ser Gly Gly Thr Tyr Tyr Ala Asp Ser Val Lys
1               5                   10                  15
Gly

<210> SEQ ID NO 8
<211> LENGTH: 13
<212> TYPE: PRT
<213> ORGANISM: Artificial Sequence
<220> FEATURE:
<223> OTHER INFORMATION: HCDR3 of anti-CD38 antibody

<400> SEQUENCE: 8

Asp Lys Ile Leu Trp Phe Gly Glu Pro Val Phe Asp Tyr
1               5                   10

<210> SEQ ID NO 9
<211> LENGTH: 11
<212> TYPE: PRT
<213> ORGANISM: Artificial Sequence
<220> FEATURE:
<223> OTHER INFORMATION: LCDR1 of anti-CD38 antibody

<400> SEQUENCE: 9

Arg Ala Ser Gln Ser Val Ser Ser Tyr Leu Ala
1               5                   10

<210> SEQ ID NO 10
<211> LENGTH: 7
<212> TYPE: PRT
<213> ORGANISM: Artificial Sequence
<220> FEATURE:
<223> OTHER INFORMATION: LCDR2 of anti-CD38 antibody

<400> SEQUENCE: 10

Asp Ala Ser Asn Arg Ala Thr
1               5

<210> SEQ ID NO 11
<211> LENGTH: 10
<212> TYPE: PRT
<213> ORGANISM: Artificial Sequence
<220> FEATURE:
<223> OTHER INFORMATION: LCDR3 of anti-CD38 antibody

<400> SEQUENCE: 11

Gln Gln Arg Ser Asn Trp Pro Pro Thr Phe
1               5                   10

<210> SEQ ID NO 12
<211> LENGTH: 452
<212> TYPE: PRT
<213> ORGANISM: Artificial Sequence
<220> FEATURE:
<223> OTHER INFORMATION: heavy chain of anti-CD38 antibody

<400> SEQUENCE: 12

Glu Val Gln Leu Leu Glu Ser Gly Gly Gly Leu Val Gln Pro Gly Gly

```
1               5                   10                  15
Ser Leu Arg Leu Ser Cys Ala Val Ser Gly Phe Thr Phe Asn Ser Phe
                20                  25                  30

Ala Met Ser Trp Val Arg Gln Ala Pro Gly Lys Gly Leu Glu Trp Val
                35                  40                  45

Ser Ala Ile Ser Gly Ser Gly Gly Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Phe Cys
                85                  90                  95

Ala Lys Asp Lys Ile Leu Trp Phe Gly Glu Pro Val Phe Asp Tyr Trp
                100                 105                 110

Gly Gln Gly Thr Leu Val Thr Val Ser Ser Ala Ser Thr Lys Gly Pro
                115                 120                 125

Ser Val Phe Pro Leu Ala Pro Ser Ser Lys Ser Thr Ser Gly Gly Thr
                130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
                180                 185                 190

Val Pro Ser Ser Ser Leu Gly Thr Gln Thr Tyr Ile Cys Asn Val Asn
                195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
                260                 265                 270

His Glu Asp Pro Glu Val Lys Phe Asn Trp Tyr Val Asp Gly Val Glu
                275                 280                 285

Val His Asn Ala Lys Thr Lys Pro Arg Glu Glu Gln Tyr Asn Ser Thr
                290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
                340                 345                 350

Val Tyr Thr Leu Pro Pro Ser Arg Glu Glu Met Thr Lys Asn Gln Val
                355                 360                 365

Ser Leu Thr Cys Leu Val Lys Gly Phe Tyr Pro Ser Asp Ile Ala Val
                370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
                420                 425                 430
```

Met His Glu Ala Leu His Asn His Tyr Thr Gln Lys Ser Leu Ser Leu
            435                 440                 445

Ser Pro Gly Lys
    450

<210> SEQ ID NO 13
<211> LENGTH: 214
<212> TYPE: PRT
<213> ORGANISM: Artificial Sequence
<220> FEATURE:
<223> OTHER INFORMATION: light chain of anti-CD38 antibody

<400> SEQUENCE: 13

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 14
<211> LENGTH: 120
<212> TYPE: PRT
<213> ORGANISM: Artificial Sequence
<220> FEATURE:
<223> OTHER INFORMATION: VH of anti-CD38 antibody

<400> SEQUENCE: 14

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Phe Ser Trp Val Arg Gln Ala Pro Gly Gln Gly Leu Glu Trp Met
        35                  40                  45

Gly Arg Val Ile Pro Phe Leu Gly Ile Ala Asn Ser Ala Gln Lys Phe

```
                    50                  55                  60
Gln Gly Arg Val Thr Ile Thr Ala Asp Lys Ser Thr Ser Thr Ala Tyr
 65                  70                  75                  80

Met Asp Leu Ser Ser Leu Arg Ser Glu Asp Thr Ala Val Tyr Tyr Cys
                 85                  90                  95

Ala Arg Asp Asp Ile Ala Ala Leu Gly Pro Phe Asp Tyr Trp Gly Gln
                100                 105                 110

Gly Thr Leu Val Thr Val Ser Ser
            115                 120

<210> SEQ ID NO 15
<211> LENGTH: 107
<212> TYPE: PRT
<213> ORGANISM: Artificial Sequence
<220> FEATURE:
<223> OTHER INFORMATION: VL of anti-CD38 antibody

<400> SEQUENCE: 15

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Ser Ser Trp
                 20                  25                  30

Leu Ala Trp Tyr Gln Gln Lys Pro Glu Lys Ala Pro Lys Ser Leu Ile
             35                  40                  45

Tyr Ala Ala Ser Ser Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser Tyr Pro Arg
                 85                  90                  95

Thr Phe Gly Gln Gly Thr Lys Val Glu Ile Lys
            100                 105

<210> SEQ ID NO 16
<211> LENGTH: 122
<212> TYPE: PRT
<213> ORGANISM: Artificial Sequence
<220> FEATURE:
<223> OTHER INFORMATION: VH of anti-CD38 antibody

<400> SEQUENCE: 16

Glu Val Gln Leu Val Gln Ser Gly Ala Glu Val Lys Lys Pro Gly Glu
  1               5                  10                  15

Ser Leu Lys Ile Ser Cys Lys Gly Ser Gly Tyr Ser Phe Ser Asn Tyr
                 20                  25                  30

Trp Ile Gly Trp Val Arg Gln Met Pro Gly Lys Gly Leu Glu Trp Met
             35                  40                  45

Gly Ile Ile Tyr Pro His Asp Ser Asp Ala Arg Tyr Ser Pro Ser Phe
         50                  55                  60

Gln Gly Gln Val Thr Phe Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg His Val Gly Trp Gly Ser Arg Tyr Trp Tyr Phe Asp Leu Trp
                100                 105                 110

Gly Arg Gly Thr Leu Val Thr Val Ser Ser
            115                 120
```

<210> SEQ ID NO 17
<211> LENGTH: 107
<212> TYPE: PRT
<213> ORGANISM: Artificial Sequence
<220> FEATURE:
<223> OTHER INFORMATION: VL of anti-CD38 antibody

<400> SEQUENCE: 17

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Thr Phe Gly Gln Gly Thr Lys Val Glu Ile Lys
            100                 105
```

<210> SEQ ID NO 18
<211> LENGTH: 120
<212> TYPE: PRT
<213> ORGANISM: Artificial Sequence
<220> FEATURE:
<223> OTHER INFORMATION: VH of anti-CD38 antibody

<400> SEQUENCE: 18

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Tyr Met Asn Trp Val Arg Gln Ala Pro Gly Lys Gly Leu Glu Trp Val
        35                  40                  45

Ser Gly Ile Ser Gly Asp Pro Ser Asn Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Pro Leu Val Tyr Thr Gly Phe Ala Tyr Trp Gly Gln
            100                 105                 110

Gly Thr Leu Val Thr Val Ser Ser
        115                 120
```

<210> SEQ ID NO 19
<211> LENGTH: 109
<212> TYPE: PRT
<213> ORGANISM: Artificial Sequence
<220> FEATURE:
<223> OTHER INFORMATION: VL of anti-CD38 antibody

<400> SEQUENCE: 19

```
Asp Ile Glu Leu Thr Gln Pro Pro Ser Val Ser Val Ala Pro Gly Gln
1               5                   10                  15

Thr Ala Arg Ile Ser Cys Ser Gly Asp Asn Leu Arg His Tyr Tyr Val
```

```
                    20                  25                  30
Tyr Trp Tyr Gln Gln Lys Pro Gly Gln Ala Pro Val Leu Val Ile Tyr
            35                  40                  45

Gly Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Thr Tyr Thr Gly Gly Ala Ser Leu
                85                  90                  95

Val Phe Gly Gly Gly Thr Lys Leu Thr Val Leu Gly Gln
            100                 105

<210> SEQ ID NO 20
<211> LENGTH: 120
<212> TYPE: PRT
<213> ORGANISM: Artificial Sequence
<220> FEATURE:
<223> OTHER INFORMATION: VH of anti-CD38 antibody

<400> SEQUENCE: 20

Gln Val Gln Leu Val Gln Ser Gly Ala Glu Val Ala Lys Pro Gly Thr
1               5                   10                  15

Ser Val Lys Leu Ser Cys Lys Ala Ser Gly Tyr Thr Phe Thr Asp Tyr
            20                  25                  30

Trp Met Gln Trp Val Lys Gln Arg Pro Gly Gln Gly Leu Glu Trp Ile
        35                  40                  45

Gly Thr Ile Tyr Pro Gly Asp Gly Asp Thr Gly Tyr Ala Gln Lys Phe
    50                  55                  60

Gln Gly Lys Ala Thr Leu Thr Ala Asp Lys Ser Ser Lys Thr Val Tyr
65                  70                  75                  80

Met His Leu Ser Ser Leu Ala Ser Glu Asp Ser Ala Val Tyr Tyr Cys
                85                  90                  95

Ala Arg Gly Asp Tyr Tyr Gly Ser Asn Ser Leu Asp Tyr Trp Gly Gln
            100                 105                 110

Gly Thr Ser Val Thr Val Ser Ser
        115                 120

<210> SEQ ID NO 21
<211> LENGTH: 107
<212> TYPE: PRT
<213> ORGANISM: Artificial Sequence
<220> FEATURE:
<223> OTHER INFORMATION: VL of anti-CD38 antibody

<400> SEQUENCE: 21

Asp Ile Val Met Thr Gln Ser His Leu Ser Met Ser Thr Ser Leu Gly
1               5                   10                  15

Asp Pro Val Ser Ile Thr Cys Lys Ala Ser Gln Asp Val Ser Thr Val
            20                  25                  30

Val Ala Trp Tyr Gln Gln Lys Pro Gly Gln Ser Pro Arg Arg Leu Ile
        35                  40                  45

Tyr Ser Ala Ser Tyr Arg Tyr Ile Gly Val Pro Asp Arg Phe Thr Gly
    50                  55                  60

Ser Gly Ala Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Pro Pro Tyr
                85                  90                  95
```

```
Thr Phe Gly Gly Gly Thr Lys Leu Glu Ile Lys
            100                 105

<210> SEQ ID NO 22
<211> LENGTH: 4
<212> TYPE: PRT
<213> ORGANISM: Homo sapiens

<400> SEQUENCE: 22

Val Gln Leu Thr
1
```